(12) United States Patent
Wang et al.

(10) Patent No.: US 11,046,703 B2
(45) Date of Patent: Jun. 29, 2021

(54) SMALL MOLECULE MDM2 PROTEIN DEGRADERS

(71) Applicant: THE REGENTS OF THE UNIVERSITY OF MICHIGAN, Ann Arbor, MI (US)

(72) Inventors: Shaomeng Wang, Superior Township, MI (US); Angelo Aguilar, Ann Arbor, MI (US); Yangbing Li, Ann Arbor, MI (US); Jiuling Yang, Ypsilanti, MI (US); Donna McEachern, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 16/594,344

(22) Filed: Oct. 7, 2019

(65) Prior Publication Data

US 2020/0109149 A1 Apr. 9, 2020

Related U.S. Application Data

(60) Provisional application No. 62/742,627, filed on Oct. 8, 2018.

(51) Int. Cl.
C07D 487/10 (2006.01)

(52) U.S. Cl.
CPC .................. C07D 487/10 (2013.01)

(58) Field of Classification Search
None
See application file for complete search history.

(56) References Cited

U.S. PATENT DOCUMENTS

| | | | |
|---|---|---|---|
| 4,582,788 A | 4/1986 | Erlich | |
| 4,683,194 A | 7/1987 | Saiki et al. | |
| 4,683,202 A | 7/1987 | Mullis | |
| 6,617,346 B1 | 9/2003 | Kong et al. | |
| 6,734,302 B2 | 5/2004 | Kong et al. | |
| 6,916,833 B2 | 7/2005 | Kim et al. | |
| 7,060,713 B2 | 6/2006 | Kim et al. | |
| 7,083,983 B2 | 8/2006 | Lane et al. | |
| 7,132,421 B2 | 11/2006 | Fotouhi et al. | |
| 7,425,638 B2 | 9/2008 | Haley et al. | |
| 7,495,007 B2 | 2/2009 | Chen et al. | |
| 7,553,833 B2 | 6/2009 | Liu et al. | |
| 7,576,082 B2 | 8/2009 | Luk et al. | |
| 7,579,368 B2 | 8/2009 | Fotouhi et al. | |
| 7,625,895 B2 | 12/2009 | Dominique et al. | |
| 7,638,548 B2 | 12/2009 | Liu et al. | |
| 7,737,174 B2 | 6/2010 | Wang et al. | |
| 7,759,383 B2 | 7/2010 | Wang et al. | |
| 8,518,984 B2 | 8/2013 | Wang et al. | |
| 8,629,141 B2 | 1/2014 | Wang et al. | |
| 8,680,132 B2 | 3/2014 | Wang et al. | |
| 2002/0132977 A1 | 9/2002 | Yuan et al. | |
| 2005/0137137 A1 | 6/2005 | Lane et al. | |
| 2005/0227932 A1 | 10/2005 | Lu et al. | |
| 2005/0288287 A1 | 12/2005 | Fotouhi et al. | |
| 2006/0211718 A1 | 9/2006 | Weissman et al. | |
| 2006/0211757 A1 | 9/2006 | Wang et al. | |
| 2008/0171723 A1 | 7/2008 | Khan | |
| 2008/0261917 A1 | 10/2008 | Willems et al. | |
| 2009/0030181 A1 | 1/2009 | Han et al. | |
| 2009/0143364 A1 | 6/2009 | Fotouhi et al. | |
| 2009/0227542 A1 | 9/2009 | Khan | |

(Continued)

FOREIGN PATENT DOCUMENTS

| | | |
|---|---|---|
| EP | 50424 A1 | 4/1982 |
| EP | 84796 A2 | 8/1983 |

(Continued)

OTHER PUBLICATIONS

U.S. Appl. No. 16/091,541, filed Oct. 5, (Year: 2018).*
Konstantinov, Permanent magnets motor with disc armature—increases active surface, WPI World Patent Information Derwent, vol. 1985, No. 5, Jun. 11, 2014.
International Application No. PCT/US2019/054913, International Search Report and Written Opinion, dated Feb. 24, 2020.
Bingham et al., Over one hundred solvates of sulfathiazole, Chem. Commun., 603-4 (2001).
Bondeson et al., Catalytic in vivo protein knockdown by small-molecule PROTACs, Nat. Chem. Biol., 11(8):611-7 (Aug. 2015).
Buckley et al., Small-molecule inhibitors of the interaction between the E3 ligase VHL and HIF1α, Angew Chem Int Ed Engl., 51(46):11463-7 (Nov. 2012).
Buckley et al., Targeting the von Hippel-Lindau E3 ubiquitin ligase using small molecules to disrupt the VHL/HIF-1a interaction, J. Am. Chem. Soc., 134(10):4465-8 (Mar. 2012).

(Continued)

Primary Examiner — Zinna Northington Davis
(74) Attorney, Agent, or Firm — Marshall, Gerstein & Borun LLP

(57) ABSTRACT

The present disclosure provides compounds represented by Formula I:

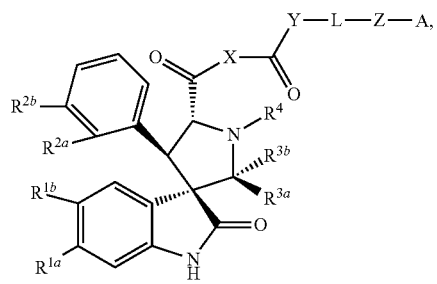

Figure 1:
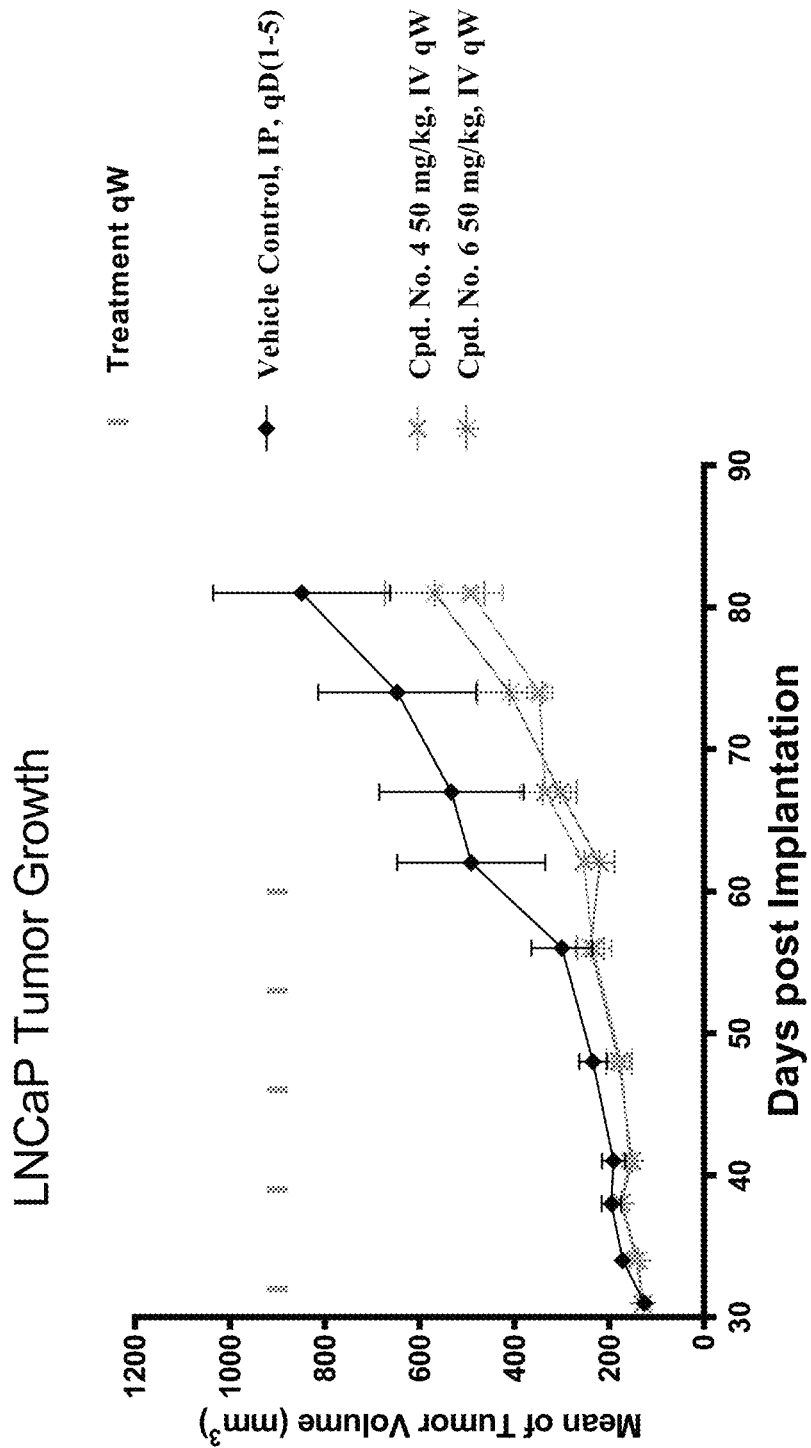

wherein $R^{1a}$, $R^{1b}$, $R^{2a}$, $R^{2b}$, $R^{3a}$, $R^{3b}$, $R^4$, A, L, X, Y, and Z are as defined as set forth in the specification. The present disclosure also provides compounds of Formula I for use to treat cancer or any other disease, condition, or disorder that is responsive to degradation of MDM2 protein.

18 Claims, 7 Drawing Sheets

(56) References Cited

U.S. PATENT DOCUMENTS

2009/0312310 A1    12/2009    Kawato et al.
2010/0048593 A1    2/2010    Weissman et al.

FOREIGN PATENT DOCUMENTS

| | | |
|---|---|---|
| EP | 201184 A2 | 11/1986 |
| EP | 237362 A1 | 9/1987 |
| EP | 258017 A2 | 3/1988 |
| WO | WO-2011/134925 A1 | 11/2011 |
| WO | WO-2017/176957 A1 | 10/2017 |

OTHER PUBLICATIONS

Caira et al., Preparation and crystal characterization of a polymorph, a monohydrate, and an ethyl acetate solvate of the antifungal fluconazole, J. Pharm. Sci., 93(3):601-11 (2004).

Chene et al., Inhibiting the p53-MDM2 interaction: an important target for cancer therapy, Nat. Rev. Cancer, 3(2):102-9 (Feb. 2003).

Ito et al., Identification of a primary target of thalidomide teratogenicity, Science, 327(5971):1345-50 (Mar. 2010).

Kamel et al., Exploitation of Gene Expression and Cancer Biomarkers in Paving the Path to Era of Personalized Medicine, Genomics Proteomics Bioinformatics, 15(4):220-35 (Aug. 2017).

Lipkowitz et al., RINGs of good and evil: RING finger ubiquitin ligases at the crossroads of tumour suppression and oncogenesis, Nat. Rev. Cancer, 11(9):629-43 (Aug. 2011).

Moll et al., The MDM2-p53 interaction, Mol. Cancer Res., 1(14):1001-8 (Dec. 2003).

Montalbetti et al., Amide bond formation and peptide coupling, Tetrahedron, 61(46):10827-52 (Nov. 2005).

Moss, Basic terminology of stereochemistry (IUPAC Recommendations 1996), Pure & Appl. Chem., 68(12): 2193 (Dec. 1996).

Mullis et al., Specific Enzymatic Amplification of DNA In Vitro: The Polymerase Chain Reaction, Cold Spring Harbor Symp. Quant. Biol., 51:263-73 (1986).

Slagle et al., Expression of ras, c-myc, and p53 proteins in cervical intraepithelial neoplasia., Cancer, 83(7):1401-8 (Oct. 1998).

Van Hagen et al., RNF4 and VHL regulate the proteasomal degradation of SUMO-conjugated Hypoxia-Inducible Factor-2alpha, Nucleic Acids Res., 38(6):1922-31 (Apr. 2010).

Vantonder et al., Preparation and physicochemical characterization of 5 niclosamide solvates and 1 hemisolvate, AAPS PharmSciTech., 5(1):E12 (2004).

Vassilev et al., In vivo activation of the p53 pathway by small-molecule antagonists of MDM2, Science, 303(5659):844-8 (Feb. 2004).

Winter et al., Drug Development. Phthalimide conjugation as a strategy for in vivo target protein degradation, Science, 348(6241):1376-81 (Jun. 2015).

Wu et al., The p53-mdm-2 autoregulatory feedback loop, Genes Dev., 7(7A):1126-32 (Jul. 1993).

Zengerle et al., Selective Small Molecule Induced Degradation of the BET Bromodomain Protein BRD4, ACS Chem. Biol., 10(8):1770-7 (Aug. 2015).

\* cited by examiner

SMALL MOLECULE MDM2 PROTEIN DEGRADERS

CROSS-REFERENCE TO RELATED APPLICATION

This application claims the benefit of U.S. Provisional Patent application No. 62/742,627, filed Oct. 8, 2018, incorporated herein by reference in its entirety.

STATEMENT OF GOVERNMENT INTEREST

This invention was made with government support under CA219345 awarded by the National Institutes of Health. The government has certain rights in the invention.

BACKGROUND OF THE INVENTION

Field of the Invention

The present disclosure provides MDM2 protein degraders and therapeutic methods of treating conditions and diseases wherein degradation of MDM2 provides a benefit

Background

The p53 tumor suppressor is a principal mediator of growth arrest, senescence, and apoptosis in response to a broad array of cellular damage. Rapid induction of high p53 protein levels by various stress types prevents inappropriate propagation of cells carrying potentially mutagenic, damaged DNA. p53 can kill cells via a dual transcription-dependent and -independent function in the nucleus and at the mitochondria. It has been demonstrated that cellular p53 protein levels are the single most important determinant of its function. In normal unstressed cells, p53 is a very unstable protein with a half-life ranging from 5 to 30 min, which is present at very low cellular levels owing to continuous degradation largely mediated by MDM2. Conversely, a hallmark of many cellular stress pathways such as DNA damage, hypoxia, telomere shortening, and oncogene activation is the rapid stabilization of p53 via a block of its degradation. MDM2 has emerged as the principal cellular antagonist of p53 by limiting the p53 tumor suppressor function. Moll and Petrenko, *Molecular Cancer Research* 1:1001-1008 (2003).

MDM2 is transcriptionally activated by p53 and MDM2, in turn, inhibits p53 activity by at least three mechanisms. Wu et al., *Genes Dev.* 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Small-molecule inhibitors that target the p53-MDM2 interaction have therapeutic potential for treating cancer and other diseases. Chene, *Nat. Rev. Cancer* 3:102 (2003) and Vassilev et al., *Science* 303:844 (2004). Antagonists of the p53-MDM2 interaction are described in U.S. Pat. Nos. 7,759,383; 7,737,174; 8,518,984; 8,680,132; 8,629,141; 6,617,346; 6,734,302; 7,132,421; 7,425,638; 7,579,368; 7,060,713; 7,553,833; 6,916,833; 7,495,007; 7,638,548; 7,576,082; 7,625,895; and 7,083,983; and U.S. Patent Application Publication Nos. 2005/0288287; 2009/0143364; 2009/0312310; 2006/0211718; 2010/0048593; 2005/0227932; 2008/0261917; 2009/0227542; 2008/0171723; 2006/0211757; 2005/0137137; 2002/0132977; and 2009/0030181.

Phthalimide-based drugs, e.g., thalidomide or lenalidomide, bind to protein-degradation machinery, e.g., cereblon (CRBN; part of an ubiquitin E3 ligase complex). This may promote the recruitment of two transcription factors (IKZF1 and IKZF3) that are essential to disease progression, resulting in drug-induced ubiquitylation and degradation by the proteasome. See, e.g., Ito et al., *Science* 327:1345-1350 (2010) and Winter et al., *Science* 348:1376-1381 (2015).

A high-affinity VHL ligand, see Bondeson et al., *Nat. Chem. Biol.* 11:611-617 (2015), may recruit a target protein to an E3 ubiquitin ligase, resulting in drug induced ubiquitination and degradation. See, e.g., van Hagen et al., *Nucleic Acids Research* 38: 1922-1931 (2010); Buckley et al., *J. Am. Chem. Soc.* 134:4465-4468 (2012); Buckley et al., *Angew. Chem. Int. Ed. Engl.* 51:11463-11467 (2012); Lipkowitz and Weissman, *Nat Rev Cancer* 11:629-643 (2011); and Zengerle et al., *ACS Chem. Biol.* 10:1770-1777 (2015).

There is an ongoing need for new agents, e.g., small molecules, for treating cancer and other diseases responsive to the disruption or prevention of the MDM2-p53 interaction.

BRIEF SUMMARY OF THE INVENTION

In one aspect, the present disclosure provides heterobifunctional compounds represented by Formula I or Formula II, below, and the pharmaceutically acceptable salts and solvates thereof, collectively referred to as "Compounds of the Disclosure." Compounds of the Disclosure are MDM2 protein degraders and thus are useful in treating diseases or conditions wherein inhibition and/or degradation of MDM2 provides a benefit.

In another aspect, the present disclosure provides methods of treating a condition or disease by administering a therapeutically effective amount of a Compound of the Disclosure to a subject, e.g., a human, in need thereof. The disease or condition of interest is treatable by degradation of MDM2 proteins, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of degrading MDM2 proteins in a subject, comprising administering to the subject an effective amount of at least one Compound of the Disclosure.

In another embodiment, the present disclosure provides a method of reducing MDM2 protein within a cell of a subject, e.g., a human patient in need thereof, the method comprising administering a Compound of the Disclosure to the subject.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein degradation of MDM2 proteins provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides a method of treating a subject having a hematological cancer, the method comprising:

(a) determining whether an overexpression of MDM2 is present or absent in a biological sample taken from the subject; and (b) administering a therapeutically effective amount of a compound of a Compound of the Disclosure to the subject if an overexpression of MDM2 is present in the biological sample.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF DRAWINGS

FIG. 1 is a line graph showing in vivo antitumor activity of Cpd. No. 4 and Cpd. No. 6 in the LNCaP prostate cancer xenograft model in SCID mice. Drug was administered I.V., once per week at 50 mg/kg for 5 weeks. Each group had seven mice with each mouse bearing one tumor.

Figure 2:
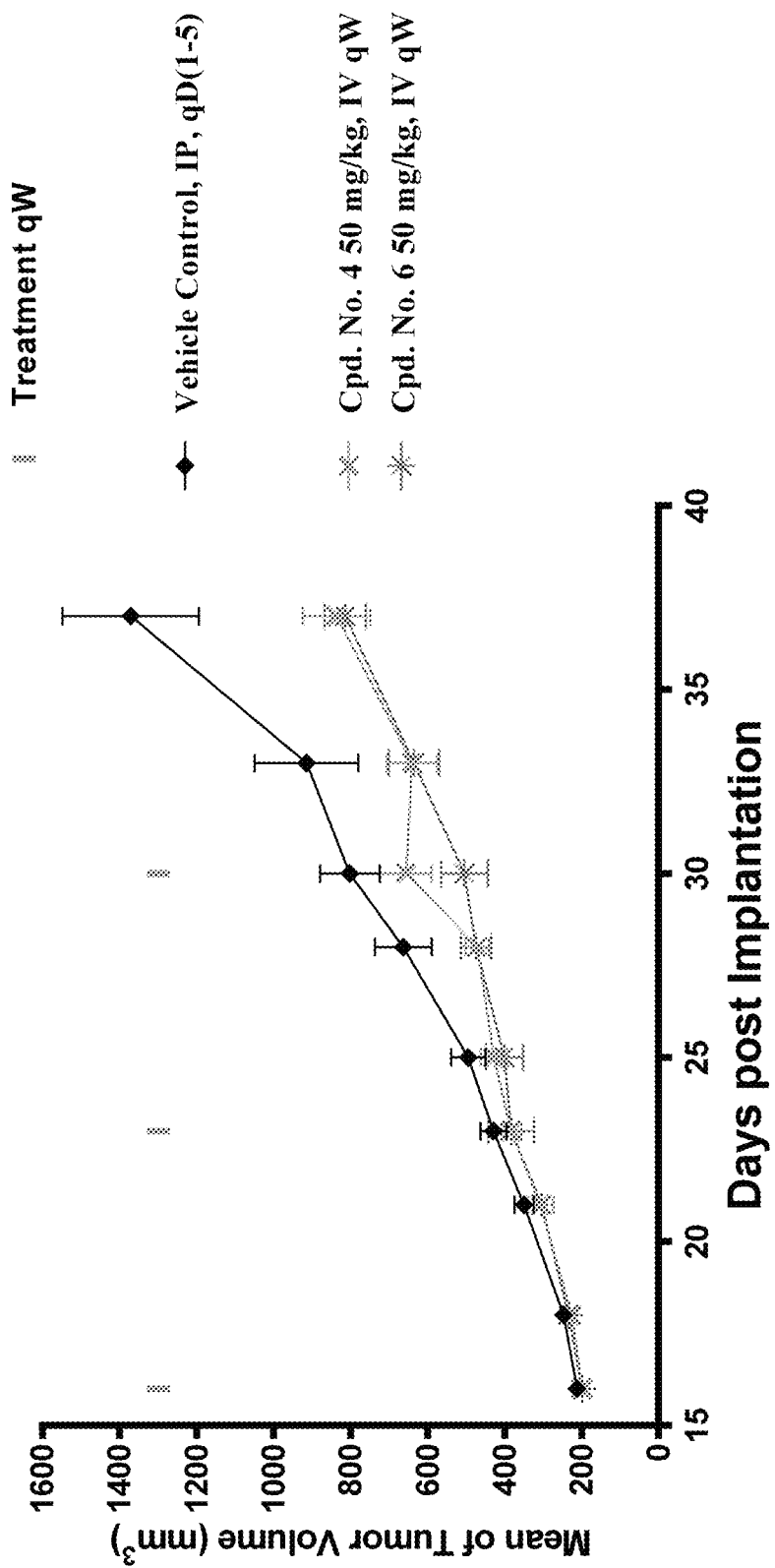

FIG. 2 is a line graph showing in vivo antitumor activity of Cpd. No. 4 and Cpd. No. 6 in the 22rv1 prostate cancer xenograft model in SCID mice. Drug was administered I.V., once per week at 50 mg/kg for 3 weeks. Each group had seven mice and each mouse bearing one tumor.

Figure 3:
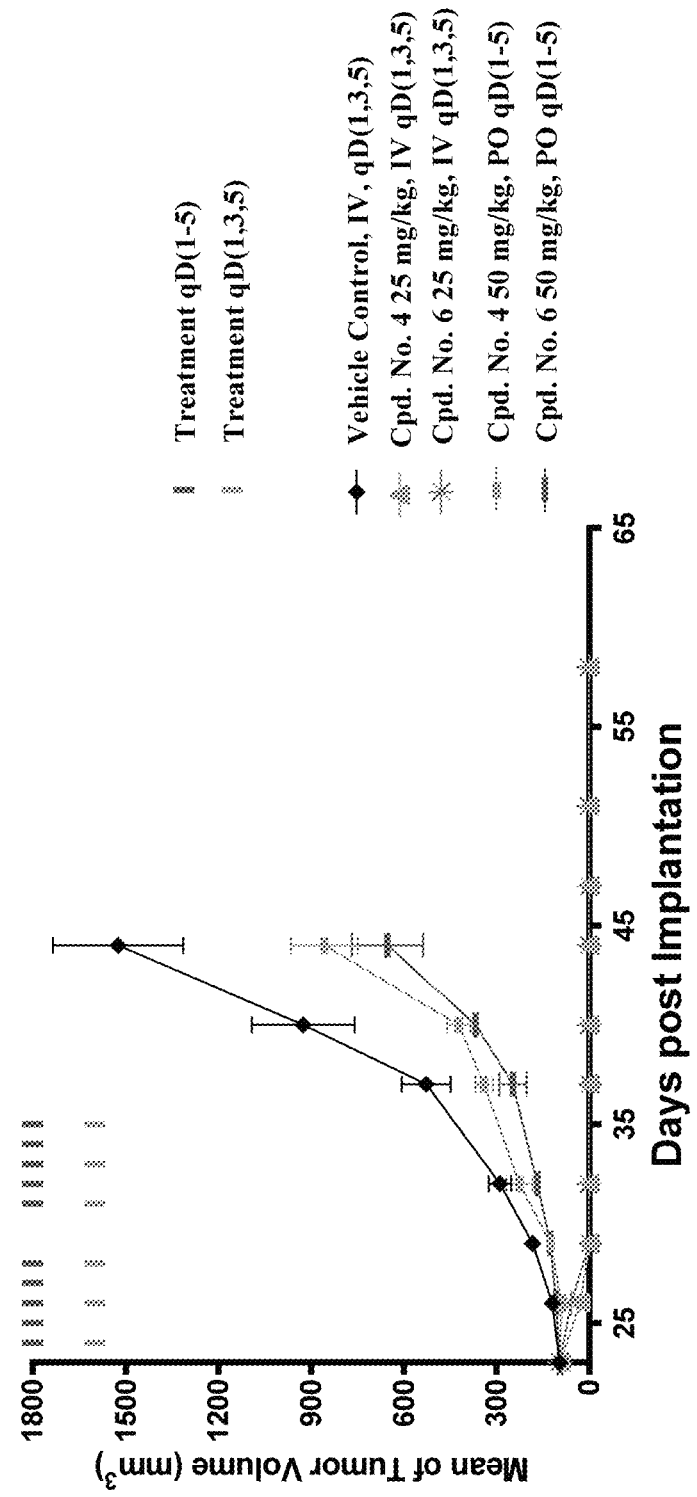

FIG. 3 is a line graph showing in vivo antitumor activity of Cpd. No. 4 and Cpd. No. 6 in the RS4;11 ALL cancer xenograft model in SCID mice. Drug was administered I.V., three times per week at 25 mg/kg for 2 weeks or via oral gavage, five times per week at 50 mg/kg for 2 weeks. Each group had five mice with each mouse bearing one tumor.

Figure 4:
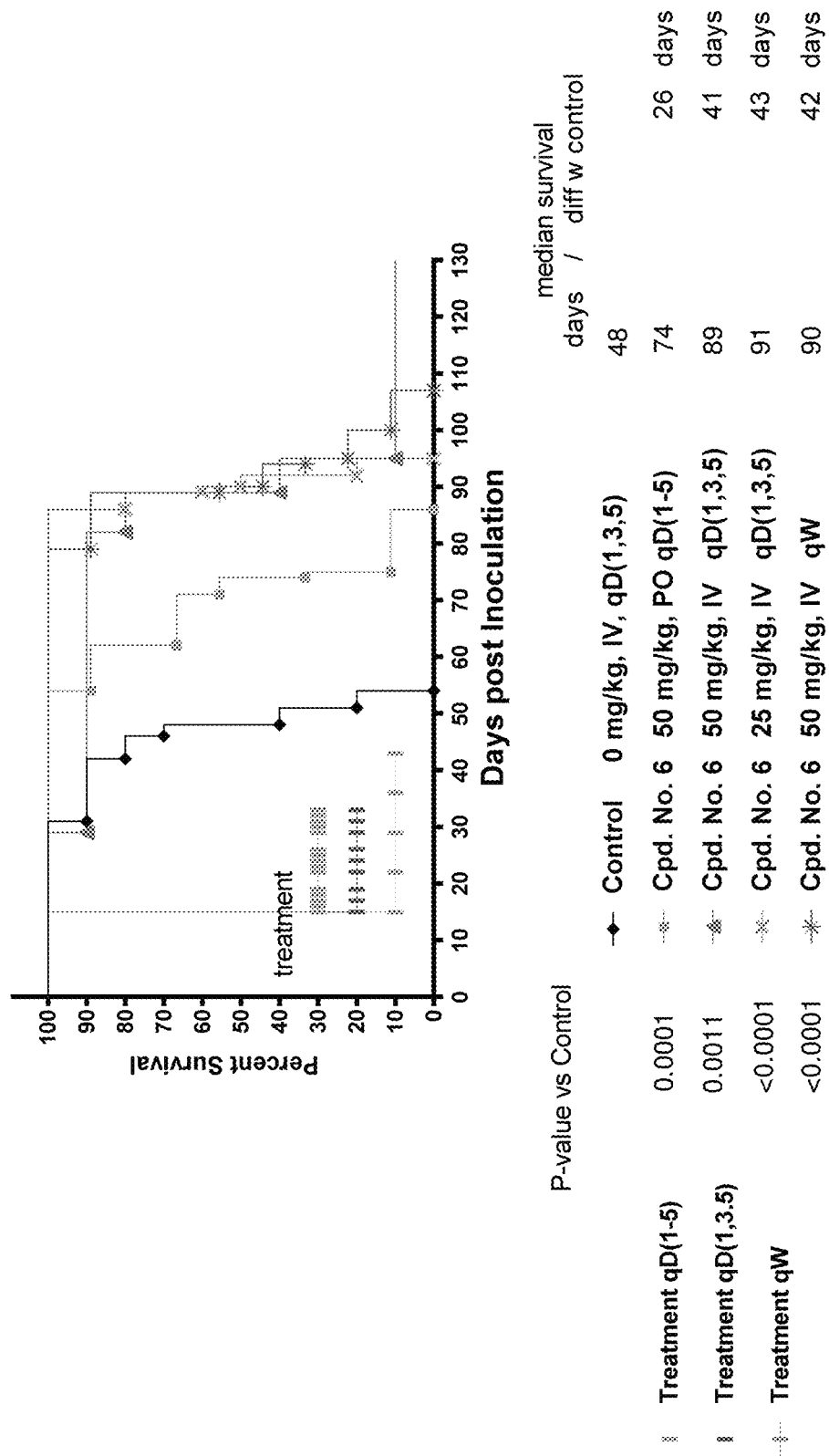

FIG. 4 is a Kaplan-Meier survival graph showing in vivo antitumor activity of Cpd. No. 6 in the RS4;11 bone marrow engraftment model in NOD-SCID mice. Drug was administered at route and schedule indicated. Each group had 9-10 mice. P-values were determined using Mantel-Cox Log-rank test.

Figure 5:
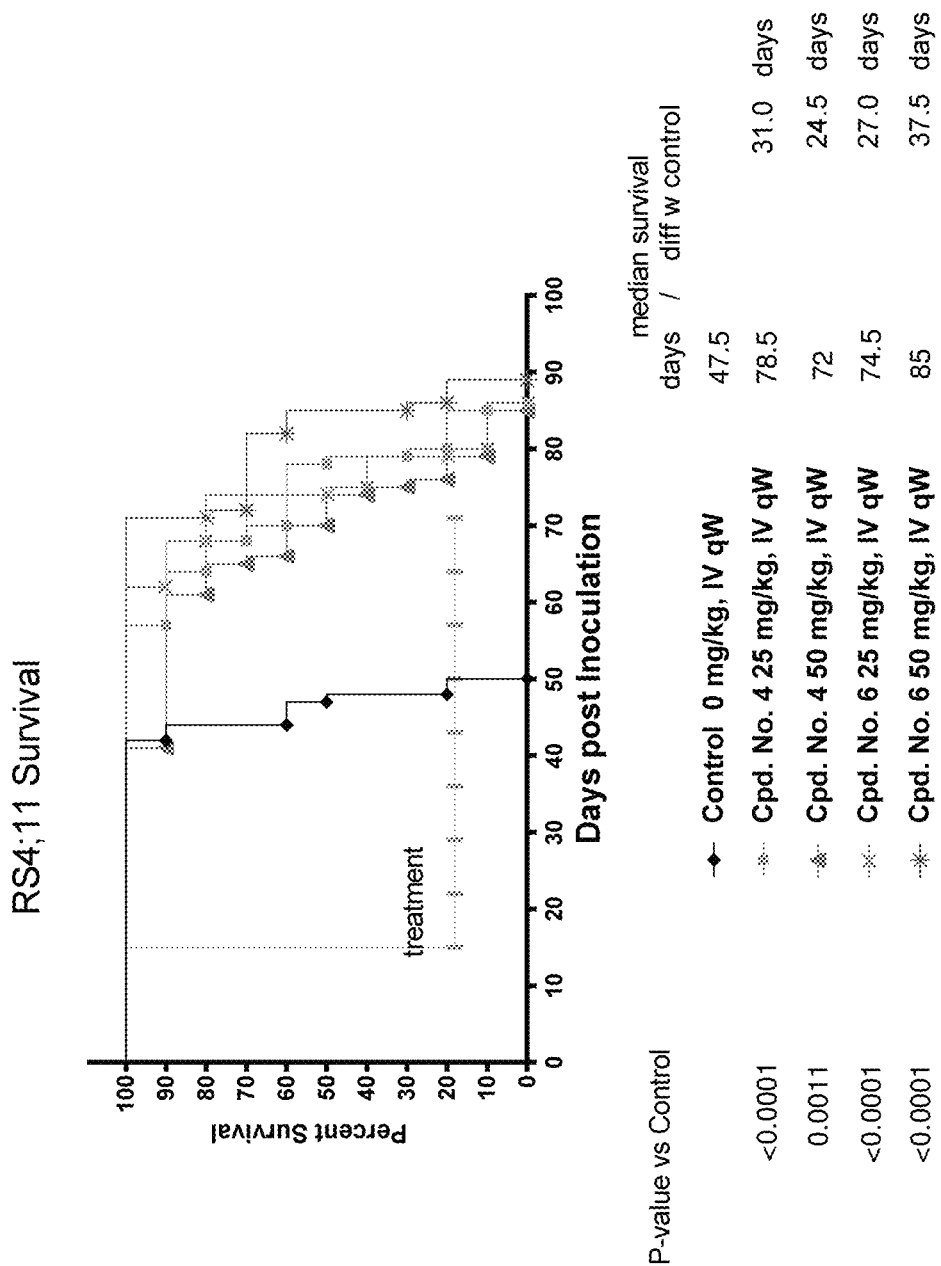

FIG. 5 is a Kaplan-Meier survival graph showing in vivo antitumor activity of Cpd. No. 4 and Cpd. No. 6 in the RS4;11 bone marrow engraftment model in NOD-SCID mice. Drug was administered at route and schedule indicated. Each group had 9 or 10 mice. P-values were determined using Mantel-Cox Log-rank test.

Figure 6:
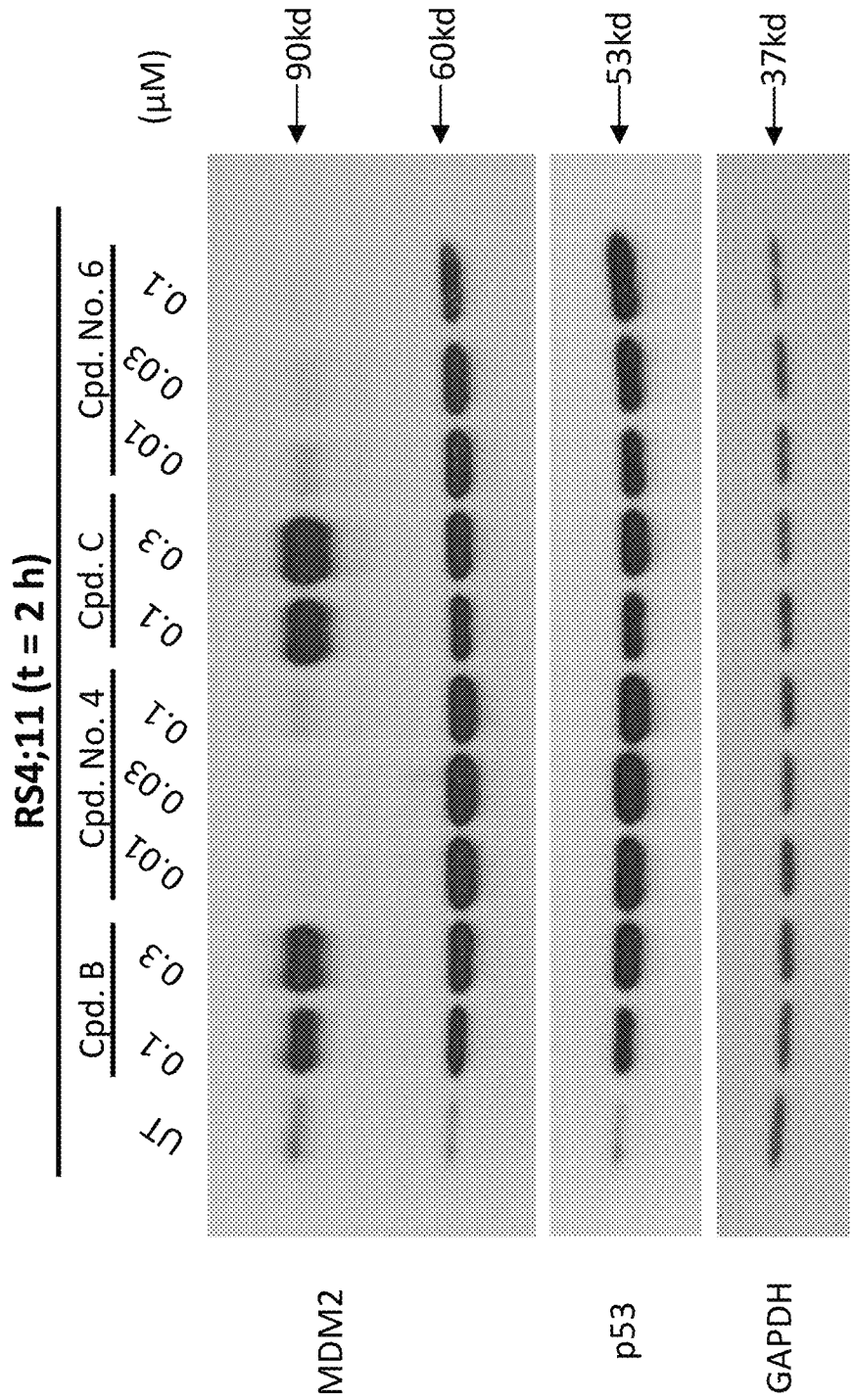

FIG. 6 is an illustration of a Western blot showing the MDM2, p53, and GAPDH protein levels in RS4;11 cells after treatment with Cpd. B, Cpd. C, Cpd. No. 4, and Cpd. No. 6 for 2 hours.

Figure 7:
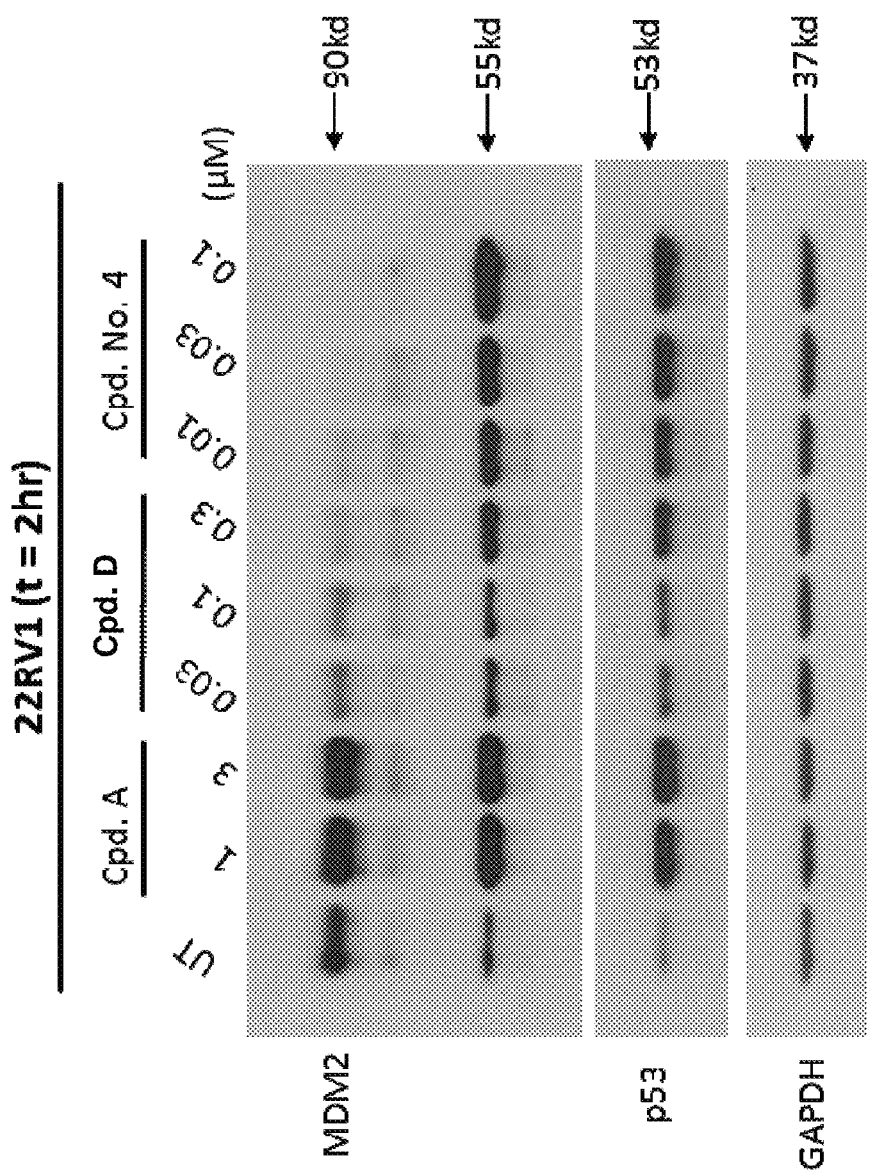

FIG. 7 is an illustration of a Western blot showing the MDM2, p53, and GAPDH protein levels in 22RV1 cells after treatment with Cpd. A, Cpd. No. 4, and Cpd. D for two hours.

DETAILED DESCRIPTION OF THE INVENTION

I. Compounds of the Disclosure

Compounds of the Disclosure are heterobifunctional compounds that promote MDM2 degradation. In one embodiment, Compounds of the Disclosure are compounds represented by Formula I:

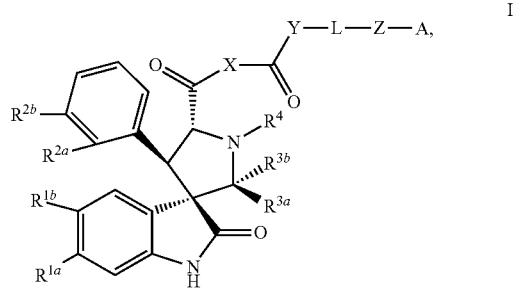

wherein:

$R^{1a}$ and $R^{1b}$ are independently selected from the group consisting of hydrogen, fluoro, and chloro;

$R^{2a}$ and $R^{2b}$ are independently selected from the group consisting of hydrogen, fluoro, and chloro;

$R^{3a}$ is —CH$_2$C(CH$_3$)$_3$;

$R^{3b}$ is hydrogen; or $R^{3a}$ and $R^{3b}$ taken together with the carbon atom to which they are attached form a cyclobutyl, cyclopentyl, or cyclohexyl group that is unsubstituted or substituted with one or two methyl groups;

$R^4$ is selected from the group consisting of hydrogen, methyl, and ethyl;

X is selected from the group consisting of:

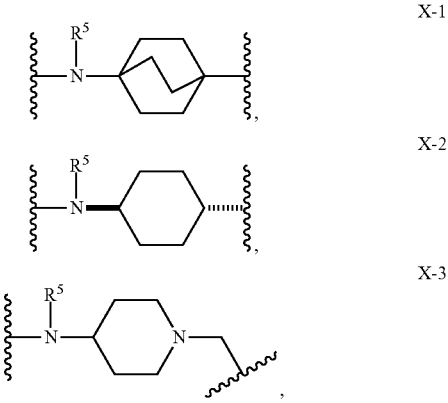

-continued

X-4

[chemical structure: piperazine with CH2 linker]

X-5

[chemical structure: N(R5) with bicyclopentane]

X-6

[chemical structure: N(R5) with cyclobutane, stereochemistry]

X-7

[chemical structure: piperidine]

X-8

[chemical structure: N(R5)-phenyl-R6]

X-9

[chemical structure: piperidine with CH2]

X-10

[chemical structure: N(R5) with cyclohexane] and

X-11

[chemical structure: N(R5) with cyclobutane];

wherein the bond projecting to the right is attached to —C(=O)—Y—L-Z-A;

each $R^5$ is independently selected from the group consisting of hydrogen and methyl;

$R^6$ is selected from the group consisting of hydrogen, fluoro, chloro, methyl, and methoxy;

Y is selected from the group consisting of:

—N(H)—,

Y-2

[chemical structure: piperidine with R7]  and

Y-3

[chemical structure: azetidine with R7];

wherein the bond projecting to the right is attached to -L-Z-A;

$R^7$ is selected from the group consisting of hydrogen, hydroxy, and methyl;

L is selected from the group consisting of —(CH$_2$)$_m$— and —(CH$_2$CH$_2$O)$_n$— m is 0, 1, 2, 3, 4, 5, 6, 7, 8, 9, or 10;

n is 2, 3, 4, 5, or 6;

Z is selected from the group consisting of —C≡C—, —NH—, —O—, and

[chemical structure: piperidine-NH linker]

or

Z is absent;

A is selected from the group consisting of

A-1

[chemical structure: lenalidomide/pomalidomide-type moiety with isoindolinone-glutarimide]

A-2

[chemical structure: VHL ligand with hydroxyproline, tert-leucine, and methylthiazole phenyl group]

A-3

[chemical structure: VHL ligand variant with additional NH linker and acetyl group]

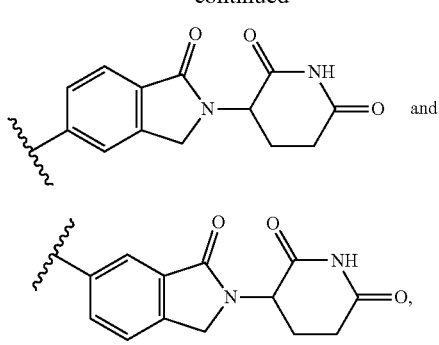

A-4 and

A-5 or a pharmaceutically acceptable salt or solvate thereof.

In another embodiment, Compounds of the Disclosure are compounds represented by Formula I, wherein $R^{3a}$ is —$CH_2C(CH_3)_3$ and $R^{3b}$ is hydrogen, or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form an cyclohexyl group that is unsubstituted, or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a cyclohexyl group that is unsubstituted or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a cyclobutyl group that is unsubstituted or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a 3,3-dimethylcyclobutyl group or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a cyclopentyl group that is unsubstituted or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a cyclohexyl group that is substituted with one or two methyl groups, or a pharmaceutically acceptable salt or solvate thereof.

In another embodiment, Compounds of the Disclosure are compounds represented by Formula I, wherein $R^{3a}$ and $R^{3b}$ taken together with the carbon atom to which they are attached form a 4,4-dimethylcyclohexyl group or a pharmaceutically acceptable salt or solvate thereof.

In another embodiment, Compounds of the Disclosure are compounds represented by Formula I, wherein Y is —N(H)—, or a pharmaceutically acceptable salt or solvate thereof.

In another embodiment, Compounds of the Disclosure are compounds represented by Formula I, wherein Y is Y-2, or a pharmaceutically acceptable salt or solvate thereof. In another embodiment, $R^7$ is hydrogen. In another embodiment $R^7$ is methyl.

In another embodiment, Compounds of the Disclosure are compounds represented by Formula I, wherein Y is Y-3, or a pharmaceutically acceptable salt or solvate thereof.

In another embodiment, Compounds of the Disclosure are compounds represented by Formula I, wherein L is —$(CH_2)_m$—, or a pharmaceutically acceptable salt or solvate thereof. In another embodiment, m is 0, 1, 2, or 3. In another embodiment, m is 0.

In another embodiment, Compounds of the Disclosure are compounds represented by Formula I, wherein L is —$(CH_2CH_2O)_m$—, or a pharmaceutically acceptable salt or solvate thereof.

In another embodiment, Compounds of the Disclosure are compounds represented by Formula I, wherein Z is —C≡C—, or a pharmaceutically acceptable salt or solvate thereof.

In another embodiment, Compounds of the Disclosure are compounds represented by Formula I, wherein Z is

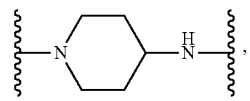

or a pharmaceutically acceptable salt or solvate thereof.

In another embodiment, Compounds of the Disclosure are compounds represented by Formula I, wherein Z is —NH—, or a pharmaceutically acceptable salt or solvate thereof.

In another embodiment, Compounds of the Disclosure are compounds represented by Formula I, wherein Z is —O—, or a pharmaceutically acceptable salt or solvate thereof.

In another embodiment, Compounds of the Disclosure are compounds represented by Formula I, wherein Z is absent, or a pharmaceutically acceptable salt or solvate thereof.

In another embodiment, Compounds of the Disclosure are compounds represented by Formula I, wherein A is A-1, or a pharmaceutically acceptable salt or solvate thereof.

In another embodiment, Compounds of the Disclosure are compounds represented by Formula I, wherein A is A-2, or a pharmaceutically acceptable salt or solvate thereof.

In another embodiment, Compounds of the Disclosure are compounds represented by Formula I, wherein A is A-3, or a pharmaceutically acceptable salt or solvate thereof.

In another embodiment, Compounds of the Disclosure are compounds represented by Formula I, wherein A is A-4, or a pharmaceutically acceptable salt or solvate thereof.

In another embodiment, Compounds of the Disclosure are compounds represented by Formula I, wherein A is A-5, or a pharmaceutically acceptable salt or solvate thereof.

In another embodiment, Compounds of the Disclosure are compounds represented by Formula II:

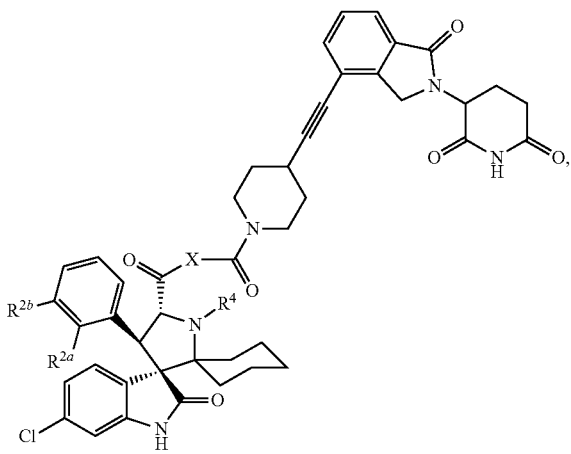

or a pharmaceutically acceptable salt or solvate thereof, wherein $R^{2a}$, $R^{2b}$, $R^4$, and X are as defined in connection with Formula I.

In another embodiment, Compounds of the Disclosure are compounds represented by Formulae I or II, wherein $R^{2a}$ is selected from the group consisting of fluoro and chloro, or a pharmaceutically acceptable salt or solvate thereof.

In another embodiment, Compounds of the Disclosure are compounds represented by Formulae I or II, wherein $R^{2b}$ is selected from the group consisting of fluoro and chloro, or a pharmaceutically acceptable salt or solvate thereof.

In another embodiment, Compounds of the Disclosure are compounds represented by Formulae I or II, wherein $R^4$ is hydrogen.

In another embodiment, Compounds of the Disclosure are compounds represented by Formulae I or II, wherein $R^4$ is methyl.

In another embodiment, Compounds of the Disclosure are compounds represented by Formulae I or II, wherein X is X-1, or a pharmaceutically acceptable salt or solvate thereof.

In another embodiment, Compounds of the Disclosure are compounds represented by Formulae I or II, wherein X is X-2, or a pharmaceutically acceptable salt or solvate thereof.

In another embodiment, Compounds of the Disclosure are compounds represented by Formulae I or II, wherein X is X-3, or a pharmaceutically acceptable salt or solvate thereof.

In another embodiment, Compounds of the Disclosure are compounds represented by Formulae I or II, wherein X is X-4, or a pharmaceutically acceptable salt or solvate thereof.

In another embodiment, Compounds of the Disclosure are compounds represented by Formulae I or II, wherein X is X-5, or a pharmaceutically acceptable salt or solvate thereof.

In another embodiment, Compounds of the Disclosure are compounds represented by Formulae I or II, wherein X is X-6, or a pharmaceutically acceptable salt or solvate thereof.

In another embodiment, Compounds of the Disclosure are compounds represented by Formulae I or II, wherein X is X-7, or a pharmaceutically acceptable salt or solvate thereof.

In another embodiment, Compounds of the Disclosure are compounds represented by Formulae I or II, wherein X is X-8, or a pharmaceutically acceptable salt or solvate thereof.

In another embodiment, Compounds of the Disclosure are compounds represented by Formulae I or II, wherein X is X-9, or a pharmaceutically acceptable salt or solvate thereof.

In another embodiment, Compounds of the Disclosure are compounds represented by Formulae I or II, wherein X is X-10, or a pharmaceutically acceptable salt or solvate thereof.

In another embodiment, Compounds of the Disclosure are compounds represented by Formulae I or II, wherein X is X-11, or a pharmaceutically acceptable salt or solvate thereof.

In another embodiment, Compounds of the Disclosure are compounds represented by Formulae I or II, wherein $R^5$ is hydrogen, or a pharmaceutically acceptable salt or solvate thereof.

In another embodiment, Compounds of the Disclosure are compounds represented by Formulae I or II, wherein $R^5$ is methyl, or a pharmaceutically acceptable salt or solvate thereof.

In another embodiment, Compounds of the Disclosure are any one or more of the compounds of Table 1, and the pharmaceutically acceptable salts and solvates thereof.

In another embodiment, Compounds of the Disclosure are any one or both of the compounds of Table 1A, and the pharmaceutically acceptable salts and solvates thereof.

Table 1B provides the chemical names of the compounds of Tables 1 and 1A generated by Chemdraw® Professional version 17.0.0.206. In the event of any ambiguity between their chemical structure and chemical name, Compounds of the Disclosure are defined by their chemical structure.

TABLE 1

| Cpd. No. | Structure |
|---|---|
| 1 | 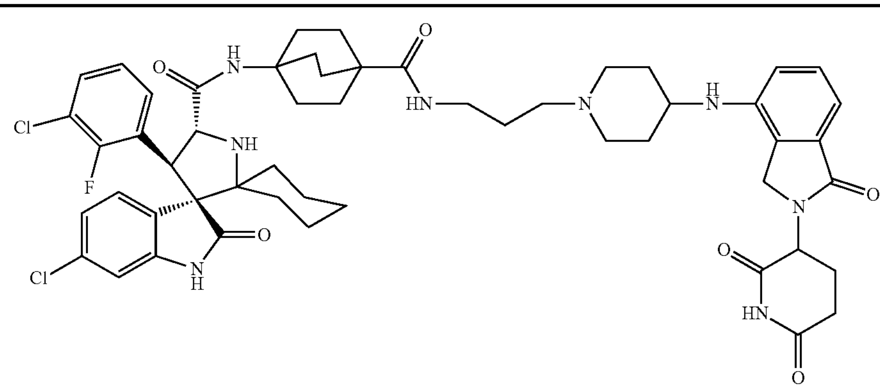 |

TABLE 1-continued

| Cpd. No. | Structure |
|---|---|
| 2 | 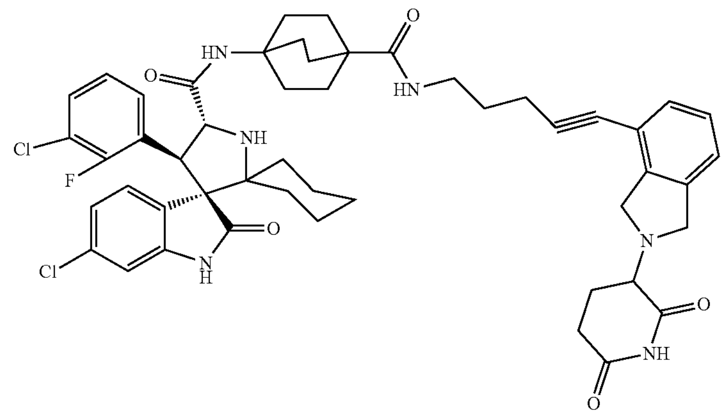 [SMILES: O=C1CCC(N2Cc3cccc(C#CCCCNC(=O)C45CCC(NC(=O)[C@@H]6NC7(CCCCC7)[C@@]7(C(=O)Nc8cc(Cl)ccc87)[C@H]6c6cccc(Cl)c6F)(CC4)CC5)c3C2)C(=O)N1] |
| 3 | 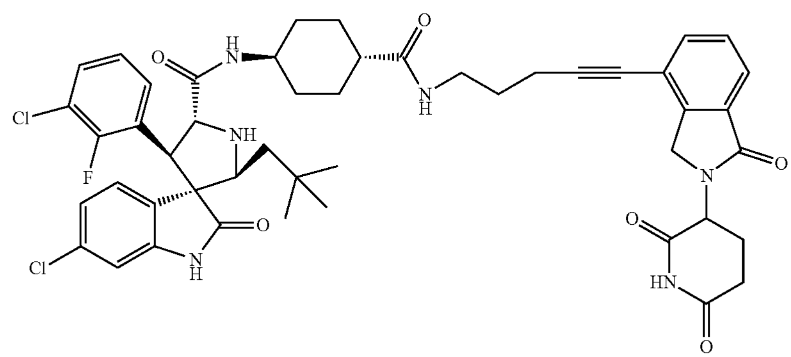 [SMILES: CC(C)(C)C[C@@H]1N[C@@H](C(=O)N[C@H]2CC[C@H](C(=O)NCCCC#Cc3cccc4c3CN(C3CCC(=O)NC3=O)C4=O)CC2)[C@H](c2cccc(Cl)c2F)[C@]12C(=O)Nc1cc(Cl)ccc12] |
| 4 | 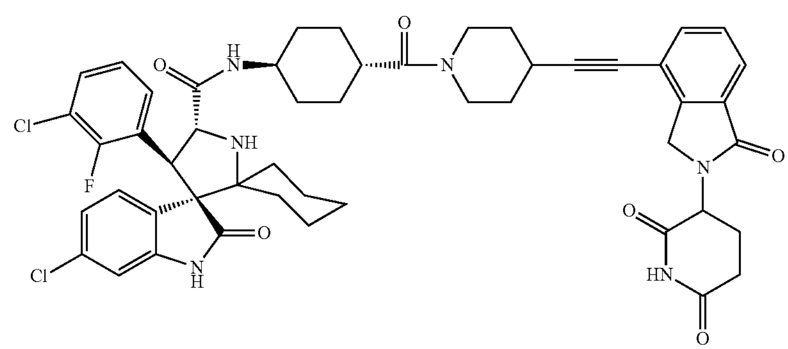 [SMILES: O=C1CCC(N2Cc3c(C#CC4CCN(C(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| 5 | 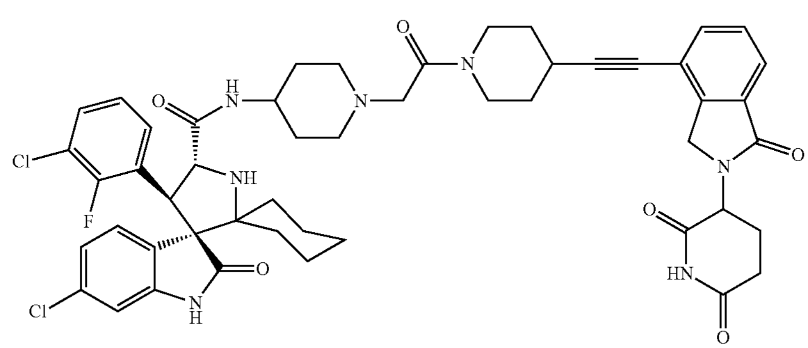 [SMILES: O=C1CCC(N2Cc3c(C#CC4CCN(C(=O)CN5CCC(NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |

TABLE 1-continued
| Cpd. No. | Structure |
|---|---|
| 6 | 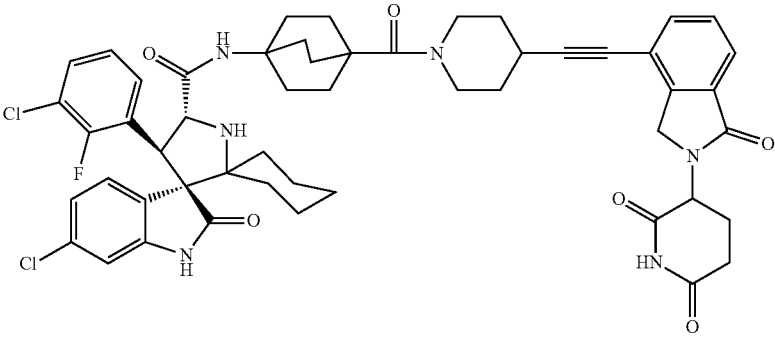 [SMILES: O=C1CCC(N2Cc3c(C#CC4CCN(C(=O)C56CCC(NC(=O)[C@@H]7NC8(CCCCC8)[C@@]8(C(=O)Nc9cc(Cl)ccc98)[C@H]7c7cccc(Cl)c7F)(CC5)CC6)CC4)cccc3C2=O)C(=O)N1] |
| 7 | 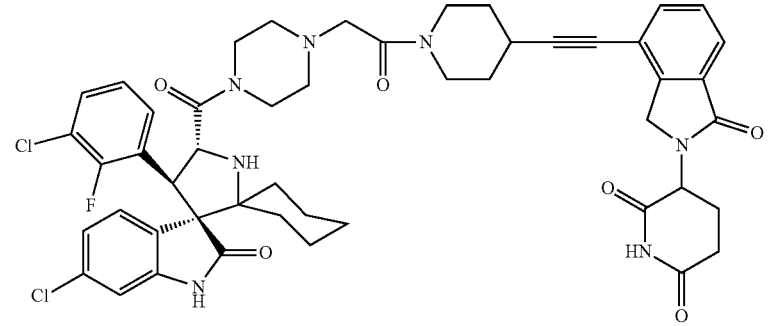 [SMILES: O=C1CCC(N2Cc3c(C#CC4CCN(C(=O)CN5CCN(C(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| 8 | 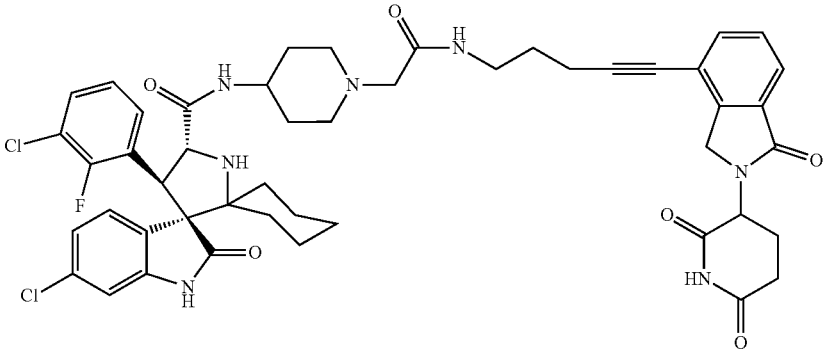 [SMILES: O=C(CN1CCC(NC(=O)[C@@H]2NC3(CCCCC3)[C@@]3(C(=O)Nc4cc(Cl)ccc43)[C@H]2c2cccc(Cl)c2F)CC1)NCCCC#Cc1cccc2c1CN(C1CCC(=O)NC1=O)C2=O] |
| 9 | 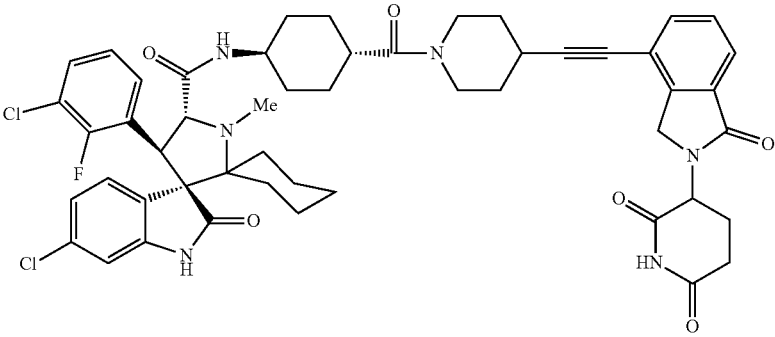 [SMILES: CN1[C@@H](C(=O)N[C@H]2CC[C@H](C(=O)N3CCC(C#Cc4cccc5c4CN(C4CCC(=O)NC4=O)C5=O)CC3)CC2)[C@H](c2cccc(Cl)c2F)[C@]2(C(=O)Nc3cc(Cl)ccc32)C12CCCCC2] |

TABLE 1-continued
| Cpd. No. | Structure |
|---|---|
| 10 | 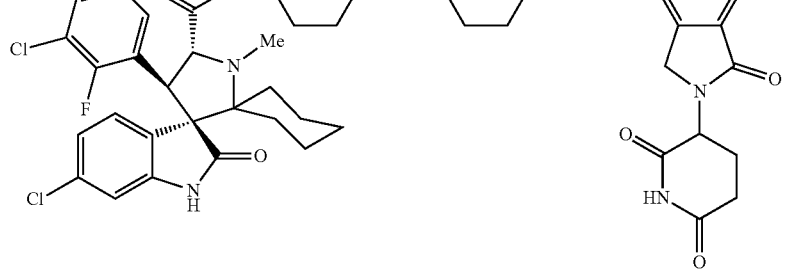 |
| 11 | 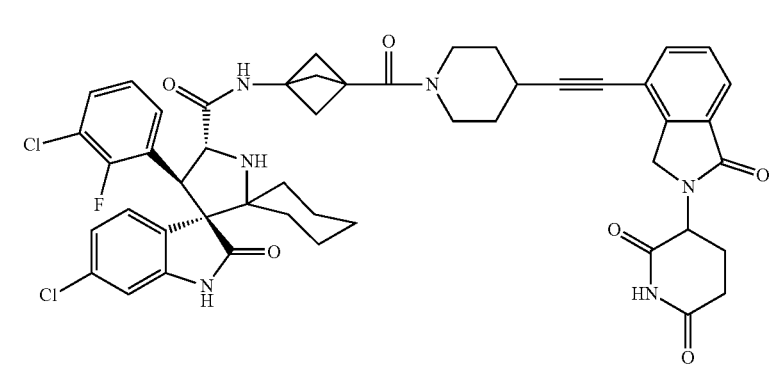 [SMILES: O=C1CCC(N2Cc3c(C#CC4CCN(C(=O)C56CC(NC(=O)[C@@H]7NC8(CCCCC8)[C@@]8(C(=O)Nc9cc(Cl)ccc98)[C@H]7c7cccc(Cl)c7F)(C5)C6)CC4)cccc3C2=O)C(=O)N1] |
| 12 | 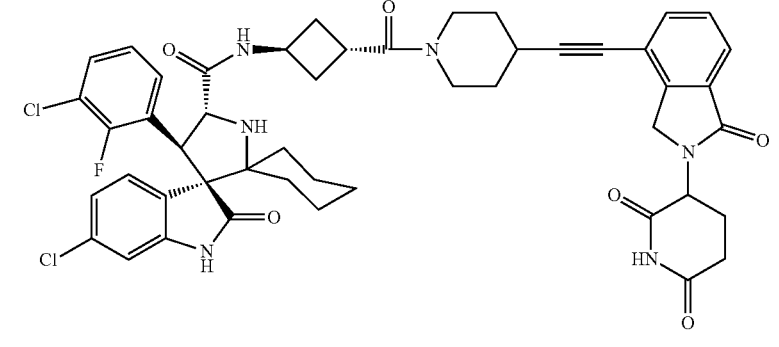 [SMILES: O=C1CCC(N2Cc3c(C#CC4CCN(C(=O)[C@H]5C[C@H](NC(=O)[C@@H]6NC7(CCCCC7)[C@@]7(C(=O)Nc8cc(Cl)ccc87)[C@H]6c6cccc(Cl)c6F)C5)CC4)cccc3C2=O)C(=O)N1] |
| 13 | 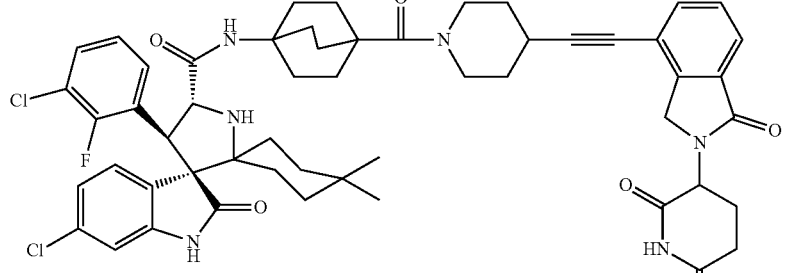 |

TABLE 1-continued
| Cpd. No. | Structure |
|---|---|
| 14 | 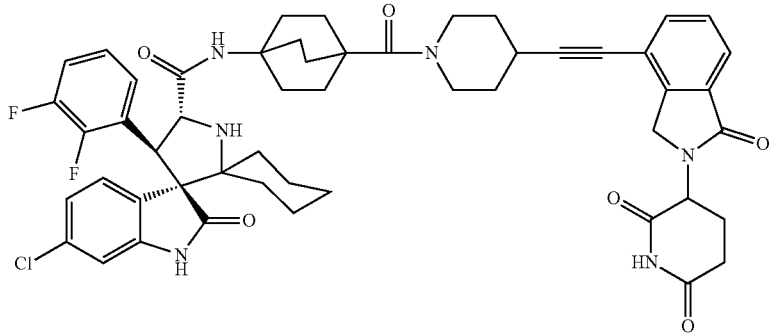 [SMILES: O=C1CCC(N2Cc3c(C#CC4CCN(C(=O)C56CCC(NC(=O)[C@@H]7NC8(CCCCC8)[C@@]8(C(=O)Nc9cc(Cl)ccc98)[C@H]7c7cccc(F)c7F)(CC5)CC6)CC4)cccc3C2=O)C(=O)N1] |
| 15 | 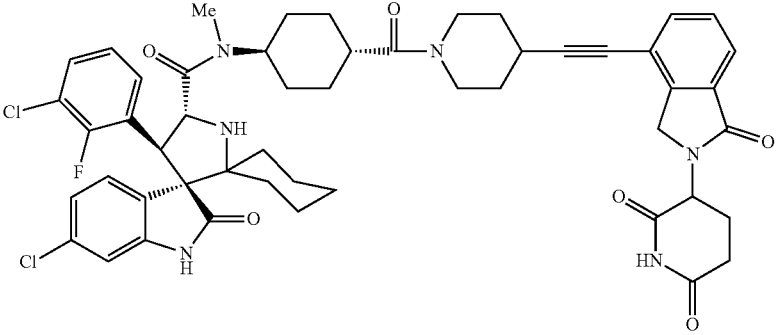 [SMILES: CN(C(=O)[C@@H]1NC2(CCCCC2)[C@@]2(C(=O)Nc3cc(Cl)ccc32)[C@H]1c1cccc(Cl)c1F)[C@H]1CC[C@H](C(=O)N2CCC(C#Cc3cccc4c3CN(C3CCC(=O)NC3=O)C4=O)CC2)CC1] |
| 16 | 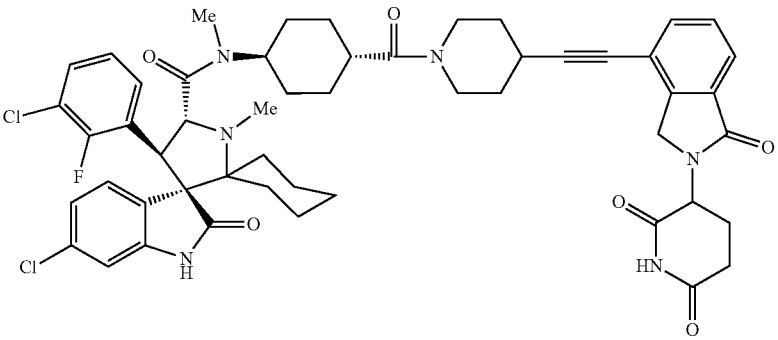 [SMILES: CN1[C@@H](C(=O)N(C)[C@H]2CC[C@H](C(=O)N3CCC(C#Cc4cccc5c4CN(C4CCC(=O)NC4=O)C5=O)CC3)CC2)[C@H](c2cccc(Cl)c2F)[C@]2(C(=O)Nc3cc(Cl)ccc32)C12CCCCC2] |
| 17 | 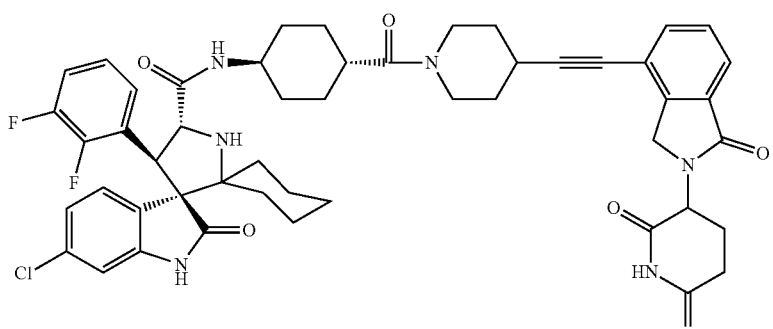 |

TABLE 1-continued
| Cpd. No. | Structure |
|---|---|
| 18 | 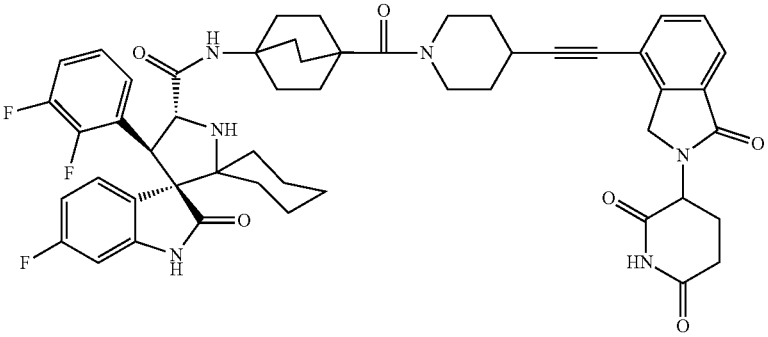 |
| 19 | 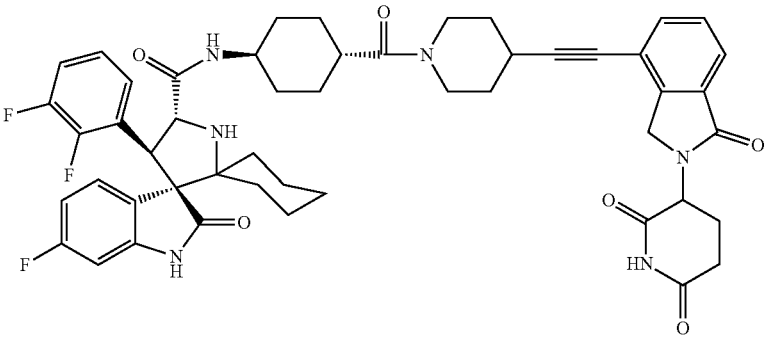 [SMILES: O=C1CCC(N2Cc3c(C#CC4CCN(C(=O)[C@H]5CC[C@H](NC(=O)[C@@H]6NC7(CCCCC7)[C@@]7(C(=O)Nc8cc(F)ccc87)[C@H]6c6cccc(F)c6F)CC5)CC4)cccc3C2=O)C(=O)N1] |
| 20 | 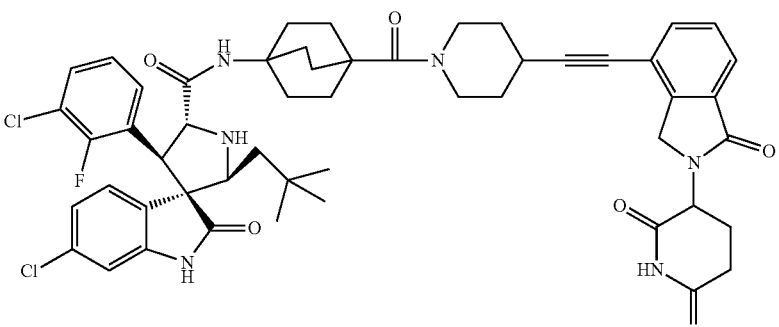 |
| 21 | 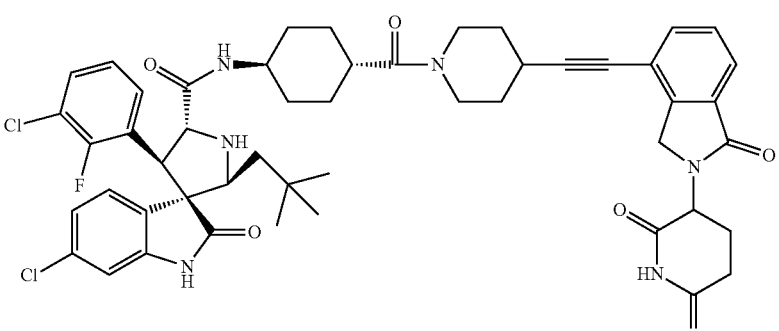 |

TABLE 1-continued
| Cpd. No. | Structure |
|---|---|
| 22 | 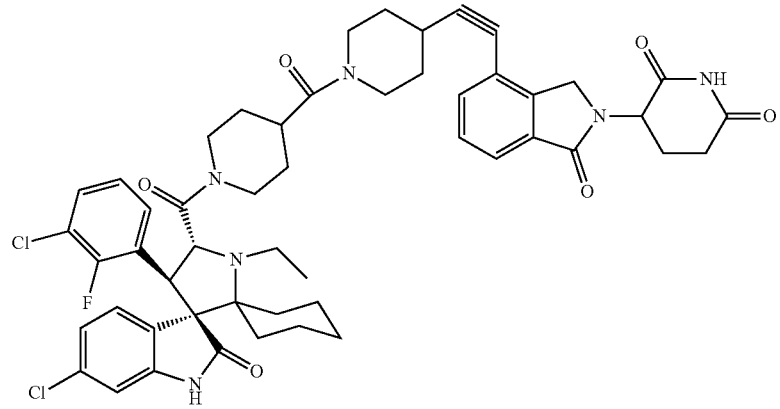 [SMILES: CCN1[C@@H](C(=O)N2CCC(C(=O)N3CCC(C#Cc4cccc5c4CN(C4CCC(=O)NC4=O)C5=O)CC3)CC2)[C@H](c2cccc(Cl)c2F)[C@]2(C(=O)Nc3cc(Cl)ccc32)C12CCCCC2] |
| 23 | 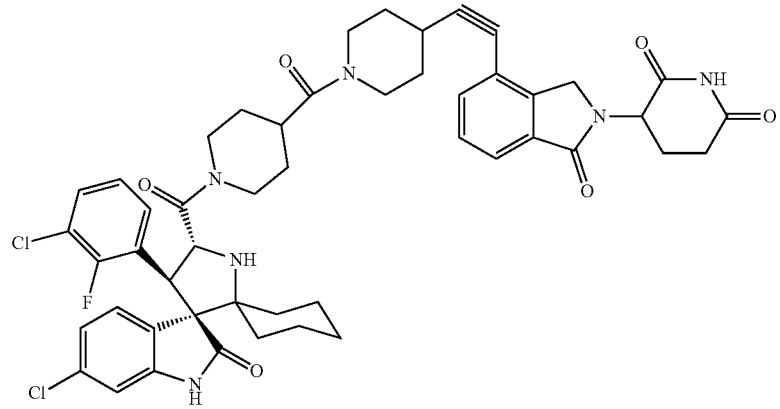 [SMILES: O=C1CCC(N2Cc3c(C#CC4CCN(C(=O)C5CCN(C(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| 24 | 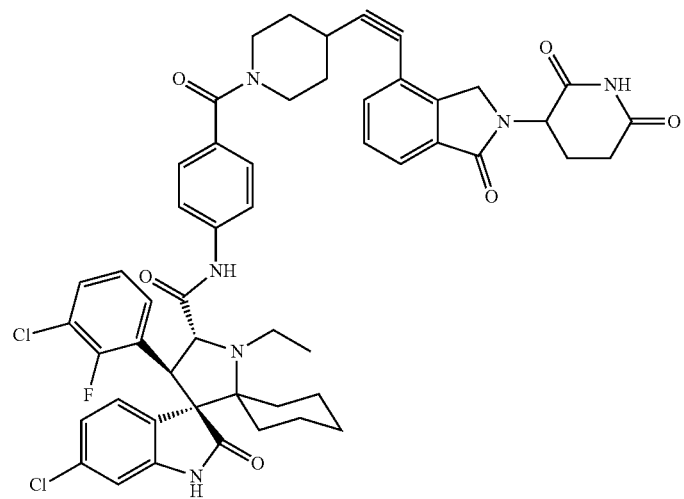 [SMILES: CCN1[C@@H](C(=O)Nc2ccc(C(=O)N3CCC(C#Cc4cccc5c4CN(C4CCC(=O)NC4=O)C5=O)CC3)cc2)[C@H](c2cccc(Cl)c2F)[C@]2(C(=O)Nc3cc(Cl)ccc32)C12CCCCC2] |

TABLE 1-continued
| Cpd. No. | Structure |
|---|---|
| 25 | 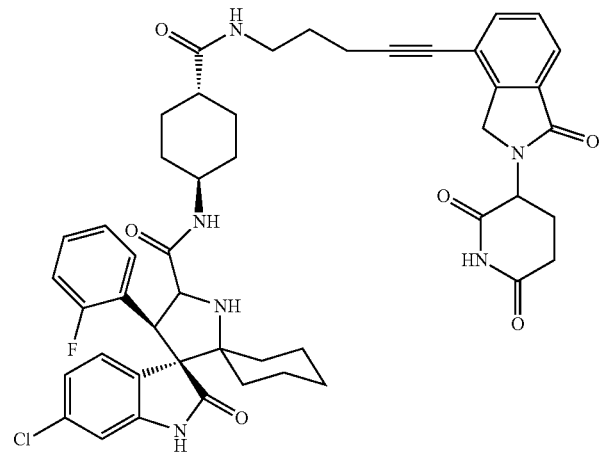 [SMILES: O=C1CCC(N2Cc3c(C#CCCCNC(=O)[C@H]4CC[C@H](NC(=O)C5NC6(CCCCC6)[C@@]6(C(=O)Nc7cc(Cl)ccc76)[C@H]5c5ccccc5F)CC4)cccc3C2=O)C(=O)N1] |
| 26 | 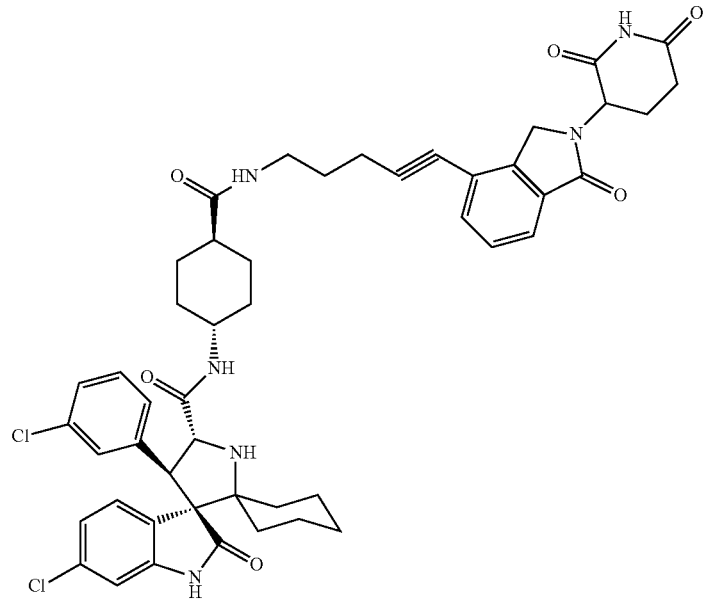 [SMILES: O=C1CCC(N2Cc3c(C#CCCCNC(=O)[C@H]4CC[C@H](NC(=O)[C@@H]5NC6(CCCCC6)[C@@]6(C(=O)Nc7cc(Cl)ccc76)[C@H]5c5cccc(Cl)c5)CC4)cccc3C2=O)C(=O)N1] |

TABLE 1-continued

| Cpd. No. | Structure |
|---|---|
| 27 | 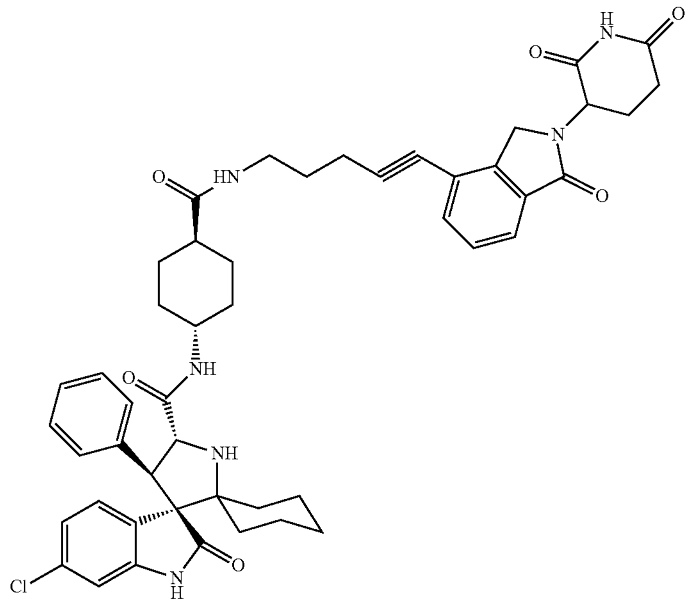 [SMILES: O=C1CCC(N2Cc3c(C#CCCCNC(=O)[C@H]4CC[C@H](NC(=O)[C@@H]5NC6(CCCCC6)[C@@]6(C(=O)Nc7cc(Cl)ccc76)[C@H]5c5ccccc5)CC4)cccc3C2=O)C(=O)N1] |
| 28 | 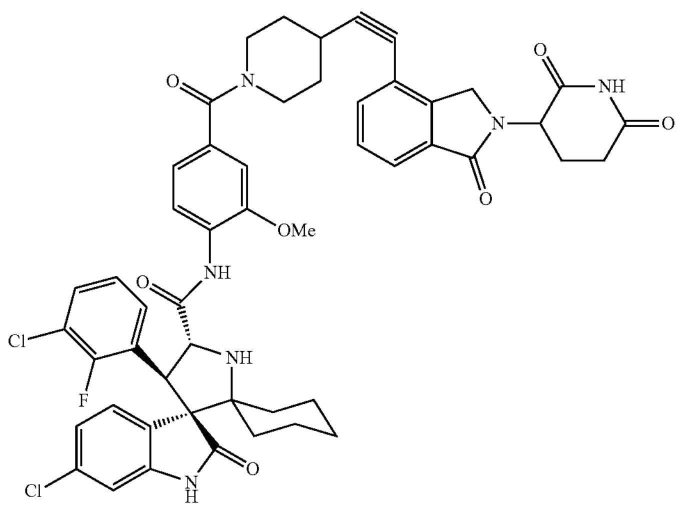 [SMILES: COc1cc(C(=O)N2CCC(C#Cc3cccc4c3CN(C3CCC(=O)NC3=O)C4=O)CC2)ccc1NC(=O)[C@@H]1NC2(CCCCC2)[C@@]2(C(=O)Nc3cc(Cl)ccc32)[C@H]1c1cccc(Cl)c1F] |
| 29 | 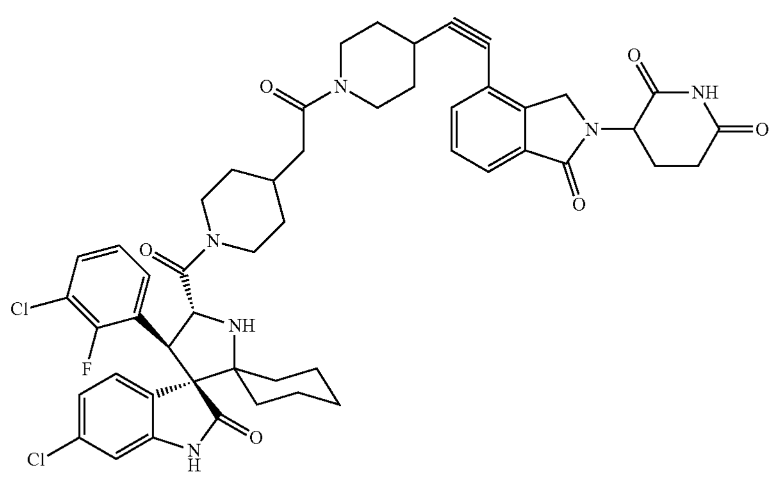 [SMILES: O=C1CCC(N2Cc3c(C#CC4CCN(C(=O)CC5CCN(C(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |

TABLE 1-continued
| Cpd. No. | Structure |
|---|---|
| 30 | 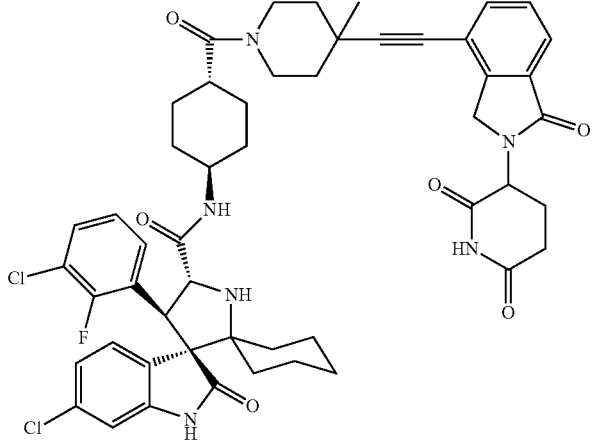 [SMILES: CC1(C#Cc2cccc3c2CN(C2CCC(=O)NC2=O)C3=O)CCN(C(=O)[C@H]2CC[C@H](NC(=O)[C@@H]3NC4(CCCCC4)[C@@]4(C(=O)Nc5cc(Cl)ccc54)[C@H]3c3cccc(Cl)c3F)CC2)CC1] |
| 31 | 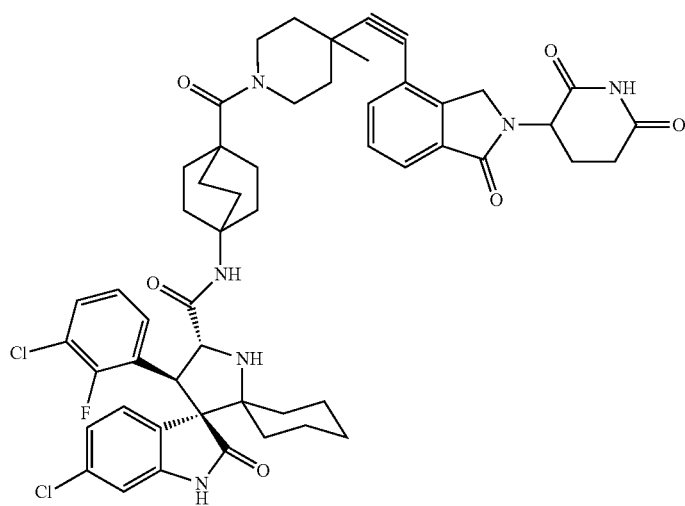 [SMILES: CC1(C#Cc2cccc3c2CN(C2CCC(=O)NC2=O)C3=O)CCN(C(=O)C23CCC(NC(=O)[C@@H]4NC5(CCCCC5)[C@@]5(C(=O)Nc6cc(Cl)ccc65)[C@H]4c4cccc(Cl)c4F)(CC2)CC3)CC1] |
| 32 | 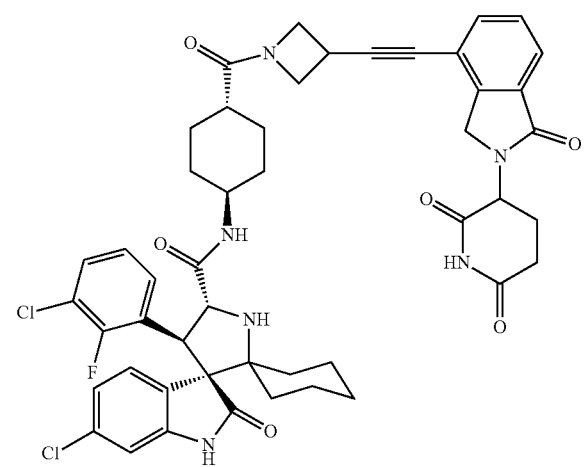 [SMILES: O=C1CCC(N2Cc3c(C#CC4CN(C(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)C4)cccc3C2=O)C(=O)N1] |

TABLE 1-continued

| Cpd. No. | Structure |
|---|---|
| 33 | 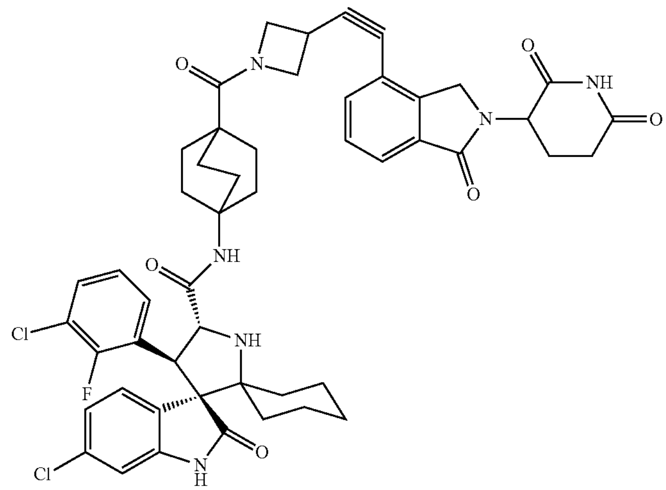 [SMILES: O=C1CCC(N2Cc3c(C#CC4CN(C(=O)C56CCC(NC(=O)[C@@H]7NC8(CCCCC8)[C@@]8(C(=O)Nc9cc(Cl)ccc98)[C@H]7c7cccc(Cl)c7F)(CC5)CC6)C4)cccc3C2=O)C(=O)N1] |
| 34 | 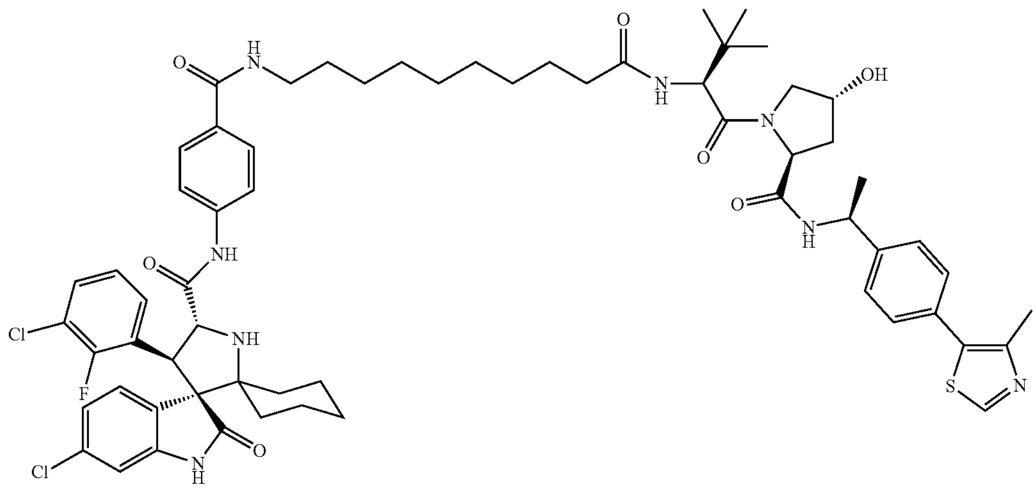 [SMILES: Cc1ncsc1-c1ccc([C@H](C)NC(=O)[C@@H]2C[C@@H](O)CN2C(=O)[C@@H](NC(=O)CCCCCCCCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| 35 | 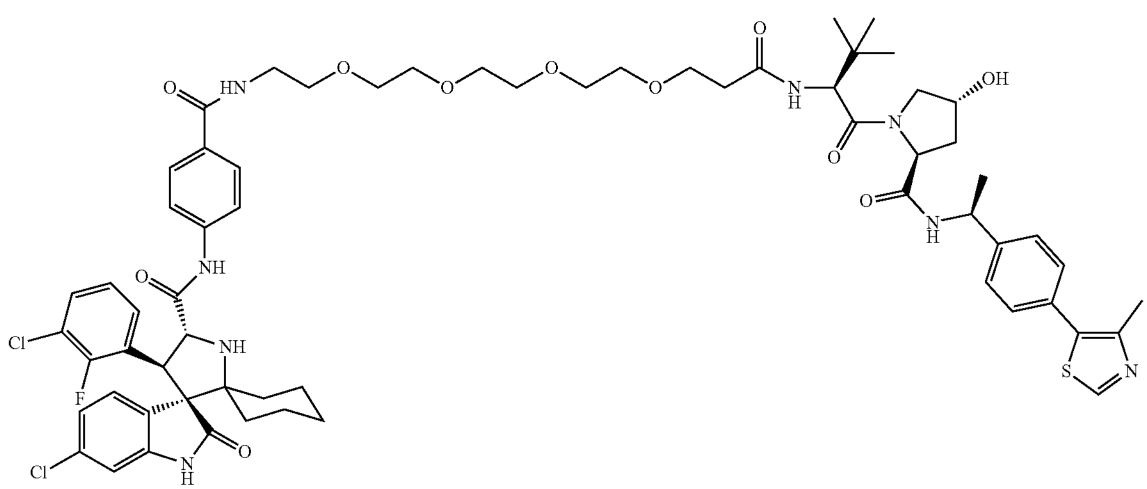 [SMILES: Cc1ncsc1-c1ccc([C@H](C)NC(=O)[C@@H]2C[C@@H](O)CN2C(=O)[C@@H](NC(=O)CCOCCOCCOCCOCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |

TABLE 1-continued
| Cpd. No. | Structure |
|---|---|
| 36 | 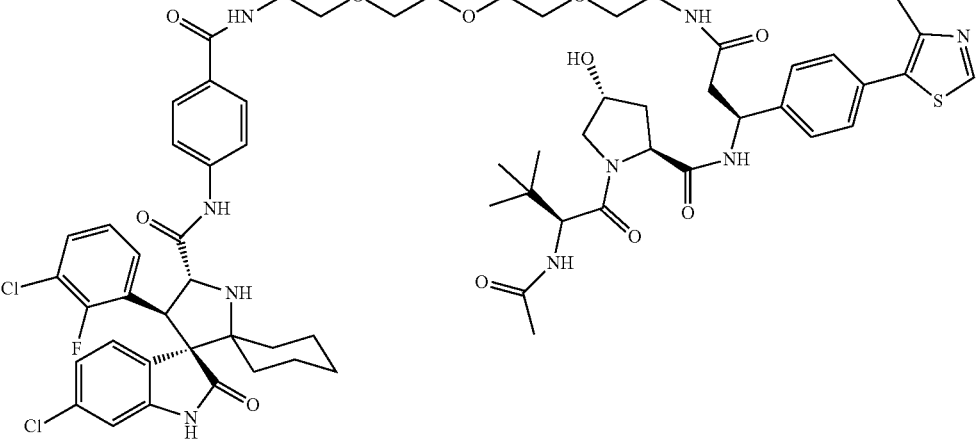 |
TABLE 1A
| Cpd. No. | Structure |
|---|---|
| 37 | 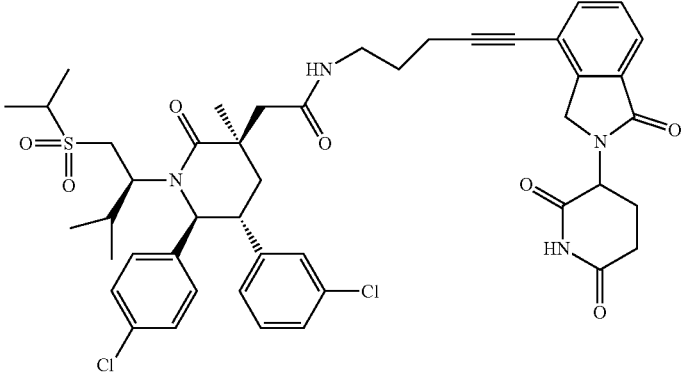 [SMILES: CC(C)[C@@H](CS(=O)(=O)C(C)C)N1C(=O)[C@@](C)(CC(=O)NCCCC#Cc2cccc3c2CN(C2CCC(=O)NC2=O)C3=O)C[C@H](c2cccc(Cl)c2)[C@H]1c1ccc(Cl)cc1] |
| 38 | 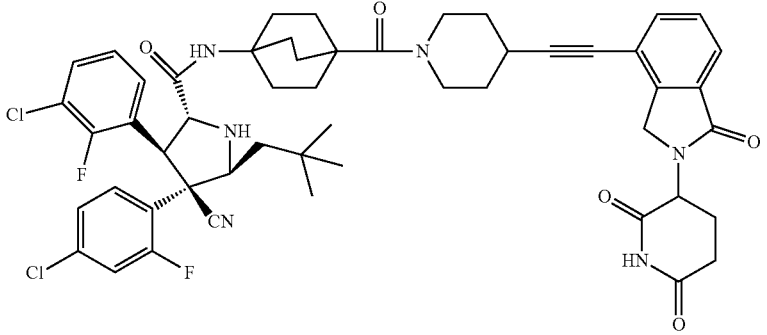 |

TABLE 1B

| Cpd. No. | Name |
|---|---|
| 1 | (3'R,4'S,5'R)-6"-chloro-4'-(3-chloro-2-fluorophenyl)-N-(4-((3-(4-((2-(2,6-dioxopiperidin-3-yl)-1-oxoisoindolin-4-yl)amino)piperidin-1-yl)propyl)carbamoyl)bicyclo[2.2.2]octan-1-yl)-2"-oxodispiro[cyclohexane-1,2'-pyrrolidine-3',3"-indoline]-5'-carboxamide |
| 2 | (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)bicyclo[2.2.2]octan-1-yl)-2"-oxodispiro[cyclohexane-1,2'-pyrrolidine-3',3"-indoline]-5'-carboxamide |
| 3 | (2'S,3R,4'S,5'R)-6-chloro-4'-(3-chloro-2-fluorophenyl)-N-((1r,4R)-4-((5-(2-(2,6-dioxopiperidin-3-yl)-1-oxoisoindolin-4-yl)pent-4-yn-1-yl)carbamoyl)cyclohexyl)-2'-neopentyl-2-oxospiro[indoline-3,3'-pyrrolidine]-5'-carboxamide |
| 4 | (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2"-oxodispiro[cyclohexane-1,2'-pyrrolidine-3',3"-indoline]-5'-carboxamide |
| 5 | (3'R,4'S,5'R)-6"-chloro-4'-(3-chloro-2-fluorophenyl)-N-(1-(2-(4-((2-(2,6-dioxopiperidin-3-yl)-1-oxoisoindolin-4-yl)ethynyl)piperidin-1-yl)-2-oxoethyl)piperidin-4-yl)-2"-oxodispiro[cyclohexane-1,2'-pyrrolidine-3',3"-indoline]-5'-carboxamide |
| 6 | (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2"-oxodispiro[cyclohexane-1,2'-pyrrolidine-3',3"-indoline]-5'-carboxamide |
| 7 | 3-(4-((1-(2-(4-((3'R,4'S,5'R)-6"-chloro-4'-(3-chloro-2-fluorophenyl)-2"-oxodispiro[cyclohexane-1,2'-pyrrolidine-3',3"-indoline]-5'-carbonyl)piperazin-1-yl)acetyl)piperidin-4-yl)ethynyl)-1-oxoisoindolin-2-yl)piperidine-2,6-dione |
| 8 | (3'R,4'S,5'R)-6"-chloro-4'-(3-chloro-2-fluorophenyl)-N-(1-(2-((5-(2-(2,6-dioxopiperidin-3-yl)-1-oxoisoindolin-4-yl)pent-4-yn-1-yl)amino)-2-oxoethyl)piperidin-4-yl)-4,4-dimethyl-2"-oxodispiro[cyclohexane-1,2'-pyrrolidine-3',3"-indoline]-5'-carboxamide |
| 9 | (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-1'-methyl-2"-oxodispiro[cyclohexane-1,2'-pyrrolidine-3',3"-indoline]-5'-carboxamide |
| 10 | (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-1'-methyl-2"-oxodispiro[cyclohexane-1,2'-pyrrolidine-3',3"-indoline]-5'-carboxamide |
| 11 | (3'R,4'S,5'R)-6"-chloro-4'-(3-chloro-2-fluorophenyl)-N-(3-(4-((2-(2,6-dioxopiperidin-3-yl)-1-oxoisoindolin-4-yl)ethynyl)piperidine-1-carbonyl)bicyclo[1.1.1]pentan-1-yl)-2"-oxodispiro[cyclohexane-1,2'-pyrrolidine-3',3"-indoline]-5'-carboxamide |
| 12 | (3'R,4'S,5'R)-6"-chloro-4'-(3-chloro-2-fluorophenyl)-N-((1r,3R)-3-(4-((2-(2,6-dioxopiperidin-3-yl)-1-oxoisoindolin-4-yl)ethynyl)piperidine-1-carbonyl)cyclobutyl)-2"-oxodispiro[cyclohexane-1,2'-pyrrolidine-3',3"-indoline]-5'-carboxamide |
| 13 | (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-4,4-dimethyl-2"-oxodispiro[cyclohexane-1,2'-pyrrolidine-3',3"-indoline]-5'-carboxamide |
| 14 | (3'R,4'S,5'R)-6"-chloro-4'-(2,3-difluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2"-oxodispiro[cyclohexane-1,2'-pyrrolidine-3',3"-indoline]-5'-carboxamide |
| 15 | (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-N-methyl-2"-oxodispiro[cyclohexane-1,2'-pyrrolidine-3',3"-indoline]-5'-carboxamide |
| 16 | (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-N,1'-dimethyl-2"-oxodispiro[cyclohexane-1,2'-pyrrolidine-3',3"-indoline]-5'-carboxamide |
| 17 | (3'R,4'S,5'R)-6"-chloro-4'-(2,3-difluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2"-oxodispiro[cyclohexane-1,2'-pyrrolidine-3',3"-indoline]-5'-carboxamide |
| 18 | (3'R,4'S,5'R)-4'-(2,3-difluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-6"-fluoro-2"-oxodispiro[cyclohexane-1,2'-pyrrolidine-3',3"-indoline]-5'-carboxamide |
| 19 | (3'R,4'S,5'R)-4'-(2,3-difluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-6"-fluoro-2"-oxodispiro[cyclohexane-1,2'-pyrrolidine-3',3"-indoline]-5'-carboxamide |

TABLE 1B-continued

| Cpd. No. | Name |
| --- | --- |
| 20 | (2'S,3R,4'S,5'R)-6-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2'-neopentyl-2-oxospiro[indoline-3,3'-pyrrolidine]-5'-carboxamide |
| 21 | (2'S,3R,4'S,5'R)-6-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2'-neopentyl-2-oxospiro[indoline-3,3'-pyrrolidine]-5'-carboxamide |
| 22 | 3-(4-((1-(1-((3'R,4'S,5'R)-6''-chloro-4'-(3-chloro-2-fluorophenyl)-1'-ethyl-2''-oxodispiro[cyclohexane-1,2'-pyrrolidine-3',3''-indoline]-5'-carbonyl)piperidine-4-carbonyl)piperidin-4-yl)ethynyl)-1-oxoisoindolin-2-yl)piperidine-2,6-dione |
| 23 | 3-(4-((1-(1-((3'R,4'S,5'R)-6''-chloro-4'-(3-chloro-2-fluorophenyl)-2''-oxodispiro[cyclohexane-1,2'-pyrrolidine-3',3''-indoline]-5'-carbonyl)piperidine-4-carbonyl)piperidin-4-yl)ethynyl)-1-oxoisoindolin-2-yl)piperidine-2,6-dione |
| 24 | (3'R,4'S,5'R)-6''-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)phenyl)-1'-ethyl-2''-oxodispiro[cyclohexane-1,2'-pyrrolidine-3',3''-indoline]-5'-carboxamide |
| 25 | (3'R,4'S,5'R)-6''-chloro-N-(4-((5-(2-(2,6-dioxopiperidin-3-yl)-1-oxoisoindolin-4-yl)pent-4-yn-1-yl)carbamoyl)cyclohexyl)-4'-(2-fluorophenyl)-2''-oxodispiro[cyclohexane-1,2'-pyrrolidine-3',3''-indoline]-5'-carboxamide |
| 26 | (3'R,4'R,5'R)-6''-chloro-4'-(3-chlorophenyl)-N-((1r,4R)-4-((5-(2-(2,6-dioxopiperidin-3-yl)-1-oxoisoindolin-4-yl)pent-4-yn-1-yl)carbamoyl)cyclohexyl)-2''-oxodispiro[cyclohexane-1,2'-pyrrolidine-3',3''-indoline]-5'-carboxamide |
| 27 | (3'R,4'R,5'R)-6''-chloro-N-((1r,4R)-4-((5-(2-(2,6-dioxopiperidin-3-yl)-1-oxoisoindolin-4-yl)pent-4-yn-1-yl)carbamoyl)cyclohexyl)-2''-oxo-4'-phenyldispiro[cyclohexane-1,2'-pyrrolidine-3',3''-indoline]-5'-carboxamide |
| 28 | (3'R,4'S,5'R)-6''-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)-2-methoxyphenyl)-2''-oxodispiro[cyclohexane-1,2'-pyrrolidine-3',3''-indoline]-5'-carboxamide |
| 29 | 3-(4-((1-(2-(1-((3'R,4'S,5'R)-6''-chloro-4'-(3-chloro-2-fluorophenyl)-2''-oxodispiro[cyclohexane-1,2'-pyrrolidine-3',3''-indoline]-5'-carbonyl)piperidin-4-yl)acetyl)piperidin-4-yl)ethynyl)-1-oxoisoindolin-2-yl)piperidine-2,6-dione |
| 30 | (3'R,4'S,5'R)-6''-chloro-4'-(3-chloro-2-fluorophenyl)-N-(4-(4-((2-(2,6-dioxopiperidin-3-yl)-1-oxoisoindolin-4-yl)ethynyl)-4-methylpiperidine-1-carbonyl)cyclohexyl)-2''-oxodispiro[cyclohexane-1,2'-pyrrolidine-3',3''-indoline]-5'-carboxamide |
| 31 | (3'R,4'S,5'R)-6''-chloro-4'-(3-chloro-2-fluorophenyl)-N-(4-(4-((2-(2,6-dioxopiperidin-3-yl)-1-oxoisoindolin-4-yl)ethynyl)-4-methylpiperidine-1-carbonyl)bicyclo[2.2.2]octan-1-yl)-2''-oxodispiro[cyclohexane-1,2'-pyrrolidine-3',3''-indoline]-5'-carboxamide |
| 32 | (3'R,4'S,5'R)-6''-chloro-4'-(3-chloro-2-fluorophenyl)-N-(4-(3-((2-(2,6-dioxopiperidin-3-yl)-1-oxoisoindolin-4-yl)ethynyl)azetidine-1-carbonyl)cyclohexyl)-2''-oxodispiro[cyclohexane-1,2'-pyrrolidine-3',3''-indoline]-5'-carboxamide |
| 33 | (3'R,4'S,5'R)-6''-chloro-4'-(3-chloro-2-fluorophenyl)-N-(4-(3-((2-(2,6-dioxopiperidin-3-yl)-1-oxoisoindolin-4-yl)ethynyl)azetidine-1-carbonyl)bicyclo[2.2.2]octan-1-yl)-2''-oxodispiro[cyclohexane-1,2'-pyrrolidine-3',3''-indoline]-5'-carboxamide |
| 34 | (3'R,4'S,5'R)-6''-chloro-4'-(3-chloro-2-fluorophenyl)-N-(4-((10-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-10-oxodecyl)carbamoyl)phenyl)-2''-oxodispiro[cyclohexane-1,2'-pyrrolidine-3',3''-indoline]-5'-carboxamide |
| 35 | (3'R,4'S,5'R)-6''-chloro-4'-(3-chloro-2-fluorophenyl)-N-(4-(((S)-17-((2S,4R)-4-hydroxy-2-(((S)-1-(4-(4-methylthiazol-5-yl)phenyl)ethyl)carbamoyl)pyrrolidine-1-carbonyl)-18,18-dimethyl-15-oxo-3,6,9,12-tetraoxa-16-azanonadecyl)carbamoyl)phenyl)-2''-oxodispiro[cyclohexane-1,2'-pyrrolidine-3',3''-indoline]-5'-carboxamide |
| 36 | (3'R,4'S,5'R)—N-(4-(((S)-1-((2S,4R)-1-((S)-2-acetamido-3,3-dimethylbutanoyl)-4-hydroxypyrrolidin-2-yl)-3-(4-(4-methylthiazol-5-yl)phenyl)-1,5-dioxo-9,12,15-trioxa-2,6-diazaheptadecan-17-yl)carbamoyl)phenyl)-6''-chloro-4'-(3-chloro-2-fluorophenyl)-2''-oxodispiro[cyclohexane-1,2'-pyrrolidine-3',3''-indoline]-5'-carboxamide |
| 37 | 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(5-(2-(2,6-dioxopiperidin-3-yl)-1-oxoisoindolin-4-yl)pent-4-yn-1-yl)acetamide |

TABLE 1B-continued

| Cpd. No. | Name |
|---|---|
| 38 | (2R,3S,4R,5S)-3-(3-chloro-2-fluorophenyl)-4-(4-chloro-2-fluorophenyl)-4-cyano-N-(4-(4-((2-(2,6-dioxopiperidin-3-yl)-1-oxoisoindolin-4-yl)ethynyl)piperidine-1-carbonyl)bicyclo[2.2.2]octan-1-yl)-5-neopentylpyrrolidine-2-carboxamide |

In another embodiment, the disclosure provides a pharmaceutical composition comprising a Compound of the Disclosure and a pharmaceutically acceptable carrier.

Compounds of the Disclosure are heterobifunctional molecules. In one embodiment, the spiro-oxindole portion of the molecule, i.e.,

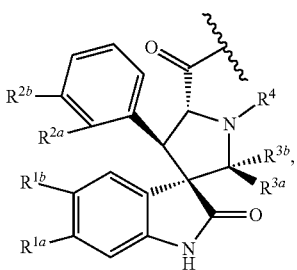

is enantiomerically enriched, e.g., the enantiomeric excess or "ee" of this part of the heterobifunctional compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

In another embodiment, the cereblon binding portion of the molecule, i.e., -A, is enantiomerically enriched. In another embodiment, the cereblon binding portion of the molecule is racemic. The present disclosure encompasses all possible stereoisomeric, e.g., diastereomeric, forms of Compounds of the Disclosure. For example, all possible stereoisomers of Compounds of the Disclosure are encompassed when the spiro-oxindole portion of the molecule is enantiomerically enriched and the cereblon binding portion of the molecule is racemic.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate (edisylate), benzene sulfonate, p-toluenesulfonate, and naphthalene-1,5-disulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

In one embodiment, salts of Compounds of the Disclosure are prepared from any of the following acids: HCl, $H_2SO_4$, p-toluenesulfonic acid, methanesulfonic acid, benzenesulfonic acid, L-aspartic acid, maleic acid, $H_3PO_4$, L-glutamic acid, malonic acid, L-tartaric acid, fumaric acid, citric acid, lactobionic acid, glycolic acid, L-malic acid, gluconic acid, DL-lactic acid, succinic acid, or acetic acid.

In another embodiment, salts of Compounds of the Disclosure are prepared from any of the following acids: hydrobromic acid, dichloroacetic acid, camphor sulfonic acid, ethane-1,2-disulfonic acid, naphthalene-1,5-disulfonic acid, naphthalene-2-sulfonic acid, or oxalic acid. In another embodiment, salts of Compounds of the Disclosure are prepared from ethane-1,2-disulfonic acid or naphthalene-1,5-disulfonic acid.

In another embodiment, the Compounds of the Disclosure are selected from the group consisting of:
(1) the ethane-1,2-disulfonic acid salt of (3'R,4'S,5'R)-6''-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2''-oxodispiro[cyclohexane-1,2'-pyrrolidine-3',3''-indoline]-5'-carboxamide;
(2) the ethane-1,2-disulfonic acid salt of (3'R,4'S,5'R)-6''-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2"-oxodispiro[cyclohexane-1,2'-pyrrolidine-3',3"-indoline]-5'-carboxamide;

(3) the naphthalene-1,5-disulfonic acid salt of (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2"-oxodispiro[cyclohexane-1,2'-pyrrolidine-3',3"-indoline]-5'-carboxamide; and (4) the naphthalene-1,5-disulfonic acid salt of (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2"-oxodispiro[cyclohexane-1,2'-pyrrolidine-3',3"-indoline]-5'-carboxamide.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof), e.g., at temperature above 20° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

II. Therapeutic Methods of the Disclosure

Compounds of the Disclosure degrade MDM2 proteins and are useful in the treatment of a variety of diseases and conditions. In particular, Compounds of the Disclosure are useful in methods of treating a disease or condition wherein degradation MDM2 proteins provides a benefit, for example, cancers and proliferative diseases. The therapeutic methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

The present disclosure provides Compounds of the Disclosure as MDM2 protein degraders for the treatment of a variety of diseases and conditions wherein degradation of MDM2 proteins has a beneficial effect. Compounds of the Disclosure typically have a binding affinity ($IC_{50}$) to MDM2 of less than 100 μM, e.g., less than 50 μM, less than 25 μM, and less than 5 μM, less than about 1 μM, less than about 0.5 μM, or less than about 0.1 μM. In one embodiment, the present disclosure relates to a method of treating an individual suffering from a disease or condition wherein degradation of MDM2 proteins provides a benefit comprising administering a therapeutically effective amount of a Compound of the Disclosure to an individual in need thereof.

Since Compounds of the Disclosure are degraders of MDM2 protein, a number of diseases and conditions mediated by MDM2 can be treated by employing these compounds. The present disclosure is thus directed generally to a method for treating a condition or disorder responsive to degradation of MDM2 in an animal, e.g., a human, suffering from, or at risk of suffering from, the condition or disorder, the method comprising administering to the animal an effective amount of one or more Compounds of the Disclosure.

The present disclosure is further directed to a method of degrading MDM2 protein in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein degradation of MDM2 protein provides a benefit, packaged separately or together, and an insert having instructions for using these active agents.

In one embodiment, a Compound of the Disclosure is administered in conjunction with a second therapeutic agent useful in the treatment of a disease or condition wherein degradation of MDM2 protein provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to degrade MDM2 protein in the patient.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by degrading MDM2 protein. Examples of treatable cancers include, but are not limited to, the cancers listed in Table 2.

TABLE 2

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |

TABLE 2-continued

| | | | |
|---|---|---|---|
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 3. In another embodiment, the hematological cancer is acute lymphocytic leukemia, chronic lymphocytic leukemia (including B-cell chronic lymphocytic leukemia), or acute myeloid leukemia.

TABLE 3

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the MDM2 protein degrader that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more.

The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

A Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Non-limiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Non-limiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary non-limiting alkylating agents include cyclophosphamide, ifosfamide, melphalan, and nitrosoureas, such as carmustine and lomustine.

Exemplary non-limiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary non-limiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary non-limiting mTOR inhibitors include compounds that inhibit the mammalian target of rapamycin (mTOR) and possess antiproliferative activity such as sirolimus, everolimus, CCI-779, and ABT578.

Exemplary non-limiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary non-limiting platin compounds include carboplatin, cis-platin, cisplatinum, and oxaliplatin.

Exemplary non-limiting methionine aminopeptidase inhibitors include bengamide or a derivative thereof and PPI-2458.

Exemplary non-limiting bisphosphonates include etridonic acid, clodronic acid, tiludronic acid, pamidronic acid, alendronic acid, ibandronic acid, risedronic acid, and zoledronic acid.

Exemplary non-limiting antiproliferative antibodies include trastuzumab, trastuzumab-DM1, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary non-limiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary non-limiting telomerase inhibitors include compounds that target, decrease, or inhibit the activity of telomerase, such as compounds that inhibit the telomerase receptor, such as telomestatin.

Exemplary non-limiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary non-limiting Flt-3 inhibitors include PKC412, midostaurin, a staurosporine derivative, SU11248, and MLN518.

Exemplary non-limiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl] amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present MDM2 degrader, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present MDM2 degrader also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate. Buffers and pH modifiers can also be added to stabilize the pharmaceutical composition.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

The disclosure provides the following particular embodiments in connection with treating a disease in a subject.

Embodiment 1

A method of treating a subject in need thereof, the method comprising administering to the subject a therapeutically effective amount a Compound of the Disclosure, wherein the subject has cancer.

Embodiment 2

The method of Embodiment 1, wherein the cancer is any one or more of the cancers of Table 2.

Embodiment 3

The method of Embodiment 2, wherein the cancer is a hematological cancer.

Embodiment 4

The method of Embodiment 3, wherein the hematological cancer is any one or more of the cancers of Table 3.

Embodiment 5

The method of any one of Embodiments 1-4 further comprising administering a therapeutically effective amount of a second therapeutic agent useful in the treatment of cancer.

Embodiment 6

A pharmaceutical composition comprising a Compound of the Disclosure and a pharmaceutically acceptable carrier for use in treating cancer.

Embodiment 7

The pharmaceutical composition of Embodiment 6, wherein the cancer is any one or more of the cancers of Table 2.

Embodiment 8

The pharmaceutical composition of Embodiment 7, wherein the cancer is a hematological cancer.

Embodiment 9

The pharmaceutical composition of Embodiment 8, wherein the hematological cancer is any one or more of the cancers of Table 3.

Embodiment 10

A Compound of the Disclosure for use in treatment of cancer.

Embodiment 11

The compound for use of Embodiment 10, wherein the cancer is any one or more of the cancers of Table 2.

Embodiment 12

The compound for use of Embodiment 11, wherein the cancer is a hematological cancer.

Embodiment 13

The compound for use of Embodiment 12, wherein the hematological cancer is any one or more of the cancers of Table 3.

Embodiment 14

Use of a Compound of the Disclosure for the manufacture of a medicament for treatment of cancer.

Embodiment 15

The use of Embodiment 14, wherein the cancer is any one or more of the cancers of Table 2.

Embodiment 16

The use of Embodiment 15, wherein the cancer is a hematological cancer.

Embodiment 17

The use of Embodiment 16, wherein the hematological cancer is any one or more of the cancers of Table 3.

III. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

IV. Biomarkers

In another embodiment, present disclosure provides methods of treating a subject having cancer, comprising (a) determining whether a biobarker is present or absent in a biological sample taken from the subject; and (b) administering a therapeutically effective amount of a Compound of the Disclosure to the subject if the biomarker is present in the biological sample. See, e.g., Goossens et al., *Transl Cancer Res.* 4:256-269 (2015); Kamel and Al-Amodi, *Genomics Proteomics Bioinformatics* 15:220-235 (2017); and Konikova and Kusenda, *Neoplasma* 50:31-40 (2003).

The term "biomarker" as used herein refers to any biological compound, such as a gene, a protein, a fragment of a protein, a peptide, a polypeptide, a nucleic acid, etc., that can be detected and/or quantified in a cancer patient in vivo or in a biological sample obtained from a cancer patient. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration, i.e., expression level, of the biomarker in a cancer patient, or biological sample obtained from the cancer patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

Biomarkers include, but are not limited to, MDM2, p53 and any one or more of the other biomarkers disclosed in US 2015/0301058. In one embodiment, the measurable aspect of the biomarker is its expression status. In one embodiment, the measurable aspect of the biomarker is its mutation status.

In one embodiment, the biomarker is MDM2 which is differentially present in a subject of one phenotypic status, e.g., a subject having a hematological cancer, as compared with another phenotypic status, e.g., a normal undiseased subject or a patient having cancer without overexpression MDM2. In one embodiment, the biomarker is overexpression of MDM2.

Biomarker standards can be predetermined, determined concurrently, or determined after a biological sample is obtained from the subject. Biomarker standards for use with the methods described herein can, for example, include data from samples from subjects without cancer; data from samples from subjects with cancer, e.g., breast cancer, that is not metastatic; and data from samples from subjects with cancer, e.g., breast cancer, that metastatic. Comparisons can be made to establish predetermined threshold biomarker standards for different classes of subjects, e.g., diseased vs. non-diseased subjects. The standards can be run in the same assay or can be known standards from a previous assay.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

In addition to individual biological compounds, e.g., MDM2, the term "biomarker" as used herein is meant to include groups, sets, or arrays of multiple biological compounds. For example, the combination of MDM2 and p53 may comprise a biomarker. The term "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting MDM2 expression, or the expression or mutation levels of any other biomarker in a patient or a biological sample may be used in the methods of the disclosure. Examples include, but are not limited to, PCR (polymerase chain reaction), or RT-PCR, flow cytometry, Northern blot, Western blot, ELISA (enzyme linked immunosorbent assay), RIA (radio-immunoassay), gene chip analysis of RNA expression, immunohistochemistry or immunofluorescence. See, e.g., Slagle et al. Cancer 83:1401 (1998). Certain embodiments of the disclosure include methods wherein biomarker RNA expression (transcription) is determined. Other embodiments of the disclosure include methods wherein protein expression in the biological sample is determined. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995); Kamel and Al-Amodi, Genomics Proteomics Bioinformatics 15:220-235 (2017). For northern blot or RT-PCR analysis, RNA is isolated from the tumor tissue sample using RNAse free techniques. Such techniques are commonly known in the art.

In one embodiment of the disclosure, a biological sample is obtained from the patient and the biological sample is assayed for determination of a biomarker, e.g., MDM2, expression or mutation status. In one embodiment, flow cytometry is used to determine MDM2 expression.

In another embodiment of the disclosure, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is pre-hybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabled probes and their use are well known in the art. The presence and or relative levels of expression of the biomarker being assayed can be quantified using, for example, densitometry.

In another embodiment, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used to determine the level of RNA encoding a biomarker of the disclosure in a tumor tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., Cold Spring Harbor Symp. Quant. Biol. 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligo-nucleotide that is hybridized to the target amplicon (biomarker gene). RT-PCR probes are oligonucleotides that have a fluorescent reporter dye attached to the 5' end and a quencher moiety coupled to the 3' end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In another embodiment of the disclosure, the expression of a biomarker is evaluated by use of a gene chip or microarray. Such techniques are within ordinary skill held in the art.

The disclosure provides the following particular embodiments in connection with biomarkers.

Embodiment I

A method of treating a subject having cancer, the method comprising:

(a) determining whether an overexpression of MDM2 is present or absent in a biological sample taken from the subject; and (b) administering a therapeutically effective amount of a Compound of the Disclosure to the subject if an overexpression of MDM2 is present in the biological sample.

Embodiment II

A method of identifying whether a subject having cancer as a candidate for treatment with a Compound of the Disclosure, the method comprising:
(a) determining whether an overexpression of MDM2 is present or absent in a biological sample taken from the subject; and
(b) identifying the subject as being a candidate for treatment if an overexpression of MDM2 is present; or
(c) identifying the subject as not being a candidate for treatment if an overexpression of MDM2 is absent.

Embodiment III

A method of predicting treatment outcome in a subject having cancer, the method comprising determining whether an overexpression of MDM2 is present or absent in a biological sample taken from the subject, wherein:
(a) the presence of an overexpression of MDM2 in the biological sample indicates that administering a Compound of the Disclosure to the subject will produce a therapeutic response in the subject; and
(b) the absence of an overexpression of MDM2 in the biological sample indicates that administering Compound of the Disclosure to the subject will not produce a therapeutic response in the subject.

Embodiment IV

A method, comprising administering a therapeutically effective amount of Compound of the Disclosure to a subject in need thereof, wherein:
(a) the subject has cancer; and
(b) the cancer is characterized as having an overexpression of MDM2.

Embodiment V

The method of any one of Embodiments I-IV, wherein the cancer is any one of more of the cancers of Table 2.

Embodiment VI

The method of Embodiment V, wherein the cancer is a hematological cancer.

Embodiment VII

The method of Embodiment VI, wherein the hematological cancer is any one or more of the hematological cancers of Table 3.

Embodiment VIII

The method of Embodiment VII, wherein the hematological cancer is acute lymphocytic leukemia, chronic lymphocytic leukemia, or acute myeloid leukemia.

V. Definitions

The term "biological sample" as used herein refers any tissue or fluid from a patient that is suitable for detecting a biomarker, such as MDM2 expression status. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the disclosure, the biological sample comprises blood cells and/or bone marrow cells.

The term "a disease or condition wherein degradation of MDM2 protein provides a benefit" pertains to a disease or condition in which MDM2 and/or an action of MDM2 is important or necessary, e.g., for the onset, progress, expression of that disease or condition, or a disease or a condition which is known to be treated by a MDM2 inhibitor or degrader. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by MDM2 for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated in the examples below, a Compound of the Disclosure is a degrader of MDM2 protein and can be used in treating diseases and conditions wherein degradation of MDM2 provides a benefit.

As used herein, the terms "treat," "treating," "treatment," refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce MDM2 signaling in the target cells; and/or relieve, to some extent, one or more of the symptoms associated with the cancer. To the extent the administered compound or composition prevents growth and/or kills existing cancer cells, it may be cytostatic and/or cytotoxic.

In one embodiment, with respect to the treatment of cancer, a therapeutically effective amount refers to the amount of a Compound of Disclosure that (a) decreases the (1) rate of tumor growth; (2) tumor mass; (3) buildup of abnormal cells in tissues and organs; or (4) the number of metastases, in a subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more; or (b) increases (1) the time to tumor progression; (2) tumor cell apoptosis; or (3) survival time, in a subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more.

Likewise, the term "therapeutic response in a subject" refers to (a) a decrease in the (1) rate of tumor growth; (2) tumor mass; (3) buildup of abnormal cells in tissues and organs; or (4) the number of metastases, in that subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more; or (b) an increase in (1) the time to tumor progression; (2) tumor cell apoptosis; or (3) survival time, in that subject by 5% or more, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

The present disclosure encompasses any of the Compounds of the Disclosure being isotopically-labeled, i.e., radiolabeled, by having one or more atoms replaced by an atom having a different atomic mass or mass number. Examples of isotopes that can be incorporated into Compounds of the Disclosure include isotopes of hydrogen, carbon, nitrogen, sulfur, oxygen, fluorine, and chlorine, such as $^{2}H$ (or deuterium (D)), $^{3}H$, $^{11}C$, $^{13}C$, $^{14}C$, $^{15}N$, $^{18}O$, $^{17}O$, $^{35}S$, $^{18}F$, and $^{36}Cl$, e.g., $^{2}H$, $^{3}H$, and $^{13}C$. In one embodiment, a portion of the atoms at a position within a Compound of the Disclosure are replaced, i.e., the Compound of the Disclosure is enriched at a position with an atom having a different atomic mass or mass number. In one embodiment, at least about 1% of the atoms are replaced with atoms having a different atomic mass or mass number. In another embodiment, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the atoms are replaced with atoms having a different atomic mass or mass number.

Compounds of the Disclosure have asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_m$ is the optical rotation of the pure enantiomer. Determination of enantiomeric excess is possible using a variety of analytical techniques, including NMR spectroscopy, chiral column chromatography or optical polarimetry.

The term "diastereomeric excess" or "de" refers to a measure for how much of one diastereomer is present compared to another, and is defined by analogy to enantiomeric excess. Determination of diastereomeric excess is possible using a variety of analytical techniques, including NMR spectroscopy and column chromatography.

General Synthesis of Compounds

Compounds of the Disclosure are prepared using methods known to those skilled in the art in view of this disclosure, or by the illustrative methods shown in the General Schemes below. Suitable protecting can be employed in the synthesis, if needed. See Wuts, P. G. M.; Greene, T. W., "Greene's Protective Groups in Organic Synthesis", 5th Ed., J. Wiley & Sons, N Y, 2014.

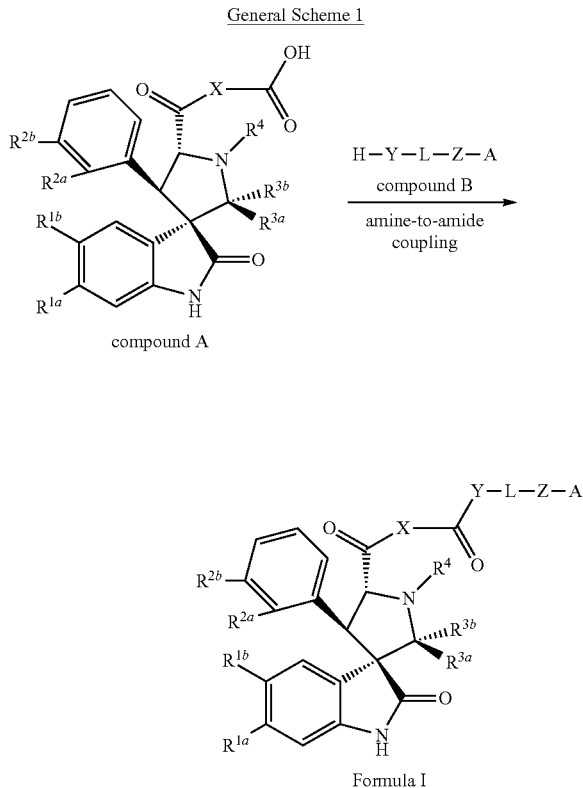

General Scheme 1

In General Scheme 1, compound A is reacted with a compound of Formula B in an organic solvent to give a compound of Formula I. Suitable amine-to-amide coupling reagents and conditions, e.g., HATU/base, HBTU/base, or EDCl/HOBt/base, are well known in the art. See Montalbetti and Falque, *Tetrahedron* 61:10827-10852 (2005).

In General Scheme 2, a compound of Formula C is reacted with compound of Formula D in an organic solvent to give a compound of Formula I.

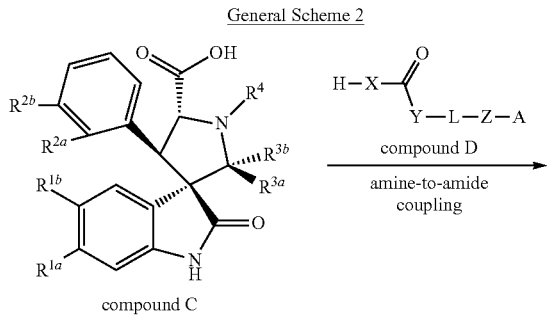

General Scheme 2

-continued

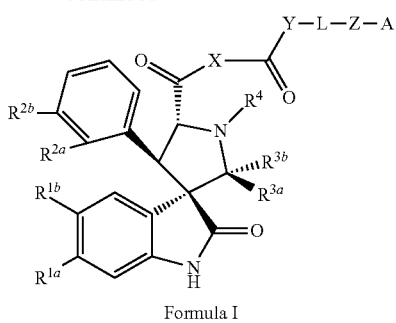

Formula I

In one embodiment, the disclosure provides a compound of Formula D, wherein X, Y, L, Z, and A are as defined in connection with Formula I as synthetic intermediates that are useful to prepare Compounds of the Disclosure.

In another embodiment, the disclosure provides:

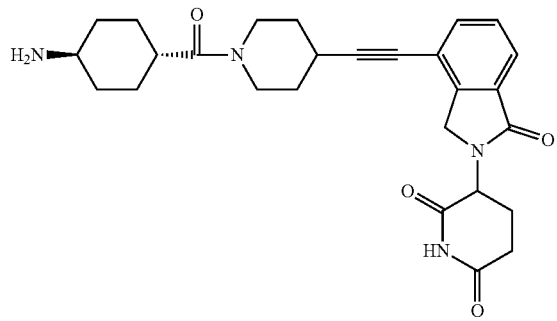 [SMILES: N[C@H]1CC[C@H](C(=O)N2CCC(C#Cc3cccc4c3CN(C3CCC(=O)NC3=O)C4=O)CC2)CC1]

(3-(4-((1-((1r,4r)-4-aminocyclohexane-1-carbonyl)piperidin-4-yl)ethynyl)-1-oxoisoindolin-2-yl)piperidine-2,6-dione) as a synthetic intermediate used to prepare Compounds of the Disclosure.

EXAMPLES

Example 1

Synthesis of (3'R,4'S,5'R)-6"-Chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2"-oxodispiro[cyclohexane-1,2'-pyrrolidine-3',3"-indoline]-5'-carboxamide (Cpd. No. 4)

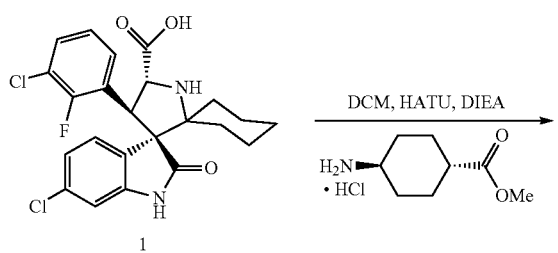

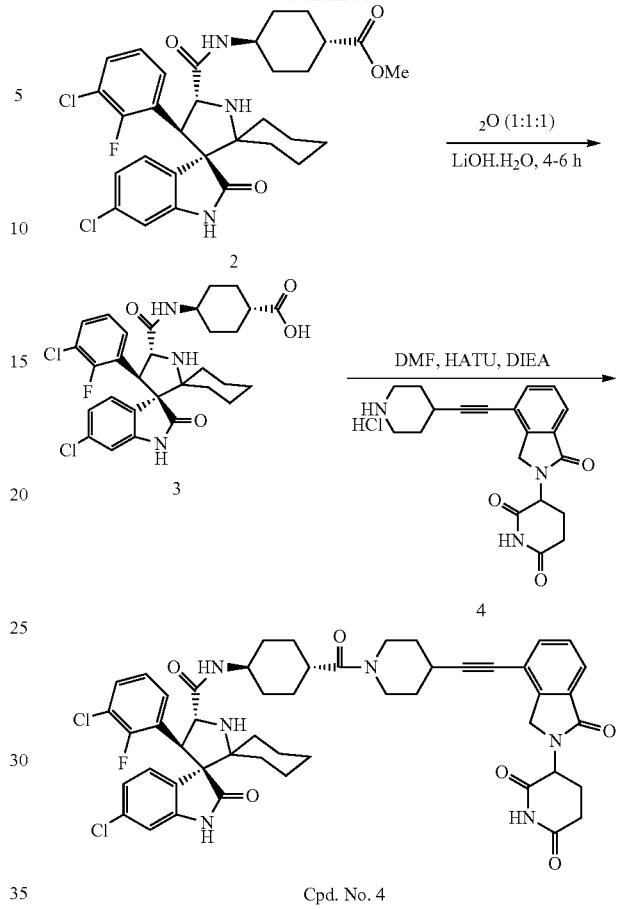

Cpd. No. 4

To a solution of Intermediate 1 (19 g, 1.0 equiv) and methyl 4-aminocyclohexane-1-carboxylate (1.1 equiv) in DCM (500 mL), was added DIPEA (1.2 equiv) and HATU (1.2 equiv). Then the mixture was stirred at r.t. for 2 h. The mixture was quenched with aq. $NaHCO_3$ and extracted with ethyl acetate three times. The organic layer was washed with brine, dried with $Na_2SO_4$, filtered, and concentrated to give the crude product which was purified by column chromatography to produce pure Intermediate 2 (82% yield, purity >95%). MS(ESI) m/z (M+H)$^+$=602.36; calcd: 602.53; $R_t$=4.98 min; $^1$H NMR (400 MHz, methanol-$d_4$) δ 7.62 (ddd, J=8.0, 6.3, 1.6 Hz, 1H), 7.40 (dd, J=8.2, 2.5 Hz, 1H), 7.21 (ddd, J=8.4, 7.0, 1.6 Hz, 1H), 7.06-6.99 (m, 2H), 6.72 (d, J=1.9 Hz, 1H), 4.66 (d, J=9.4 Hz, 1H), 4.50 (d, J=9.4 Hz, 1H), 3.66 (s, 3H), 3.66-3.52 (m, 4H), 2.34 (tt, J=12.1, 3.5 Hz, 1H), 2.09-1.77 (m, 6H), 1.77-1.43 (m, 8H), 1.43-1.24 (m, 2H), 1.14-0.99 (m, 1H), 0.94 (td, J=13.2, 4.5 Hz, 1H).

To a solution of Intermediate 3 (30 g), and amine 4 (HCl salt) (1 equiv) in DMF (450 mL) was added DIPEA (2 equiv). After stirring for 5-10 minute at r.t., HATU (1.1 eq) was added. Then the mixture was stirred for 30 mins. The reaction was quenched with $H_2O$ (1100 mL). The resulting precipitate was filtered, washed with water to give the crude product (purity=93-94%). The solid was further purified by prep-HPLC to give Cpd. No. 4 as a TFA salt. MS(ESI) m/z (M+H)$^+$=921.56; calcd: 921.89; $R_t$=5.09 min; $^1$H NMR (400 MHz, methanol-$d_4$) δ 8.22 (d, J=7.7 Hz, 1H), 7.76 (dd, J=7.6, 1.1 Hz, 1H), 7.69-7.58 (m, 2H), 7.54-7.46 (m, 2H), 7.39 (ddd, J=8.6, 7.2, 1.5 Hz, 1H), 7.17 (td, J=8.0, 1.1 Hz, 1H), 7.10 (dd, J=8.2, 2.0 Hz, 1H), 6.79 (d, J=1.9 Hz, 1H), 5.17 (dd, J=13.3, 5.2 Hz, 1H), 5.10 (d, J=11.1 Hz, 1H), 4.79 (d, J=11.2 Hz, 1H), 4.56-4.41 (m, 2H), 4.03-3.90 (m, 1H), 3.87-3.75 (m, 1H), 3.74-3.57 (m, 1H), 3.46-3.35 (m, 1H), 3.06-2.73 (m, 5H), 2.62-2.44 (m, 2H), 2.25-2.11 (m, 2H), 2.04-1.85 (m, 6H), 1.82-1.44 (m, 10H), 1.33-1.16 (m, 3H), 1.03-0.87 (m, 1H).

Example 2

Synthesis of 3-(1-oxo-4-(piperidin-4-ylethynyl) isoindolin-2-yl)piperidine-2,6-dione (Intermediate 4)

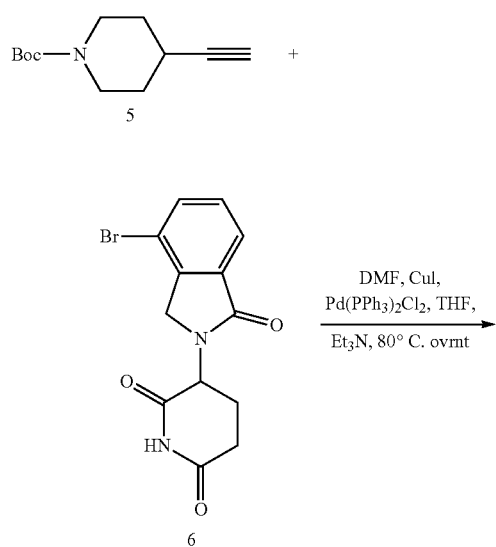

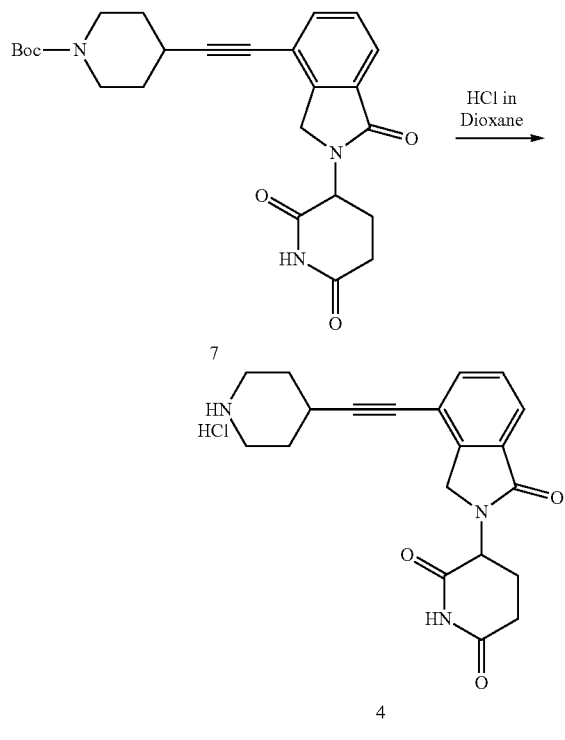

To the mixture of the Intermediate 6 (50 g, 155 mmol), 1-Boc-4-ethynylpiperidine 5 (43 g), Pd(PPh$_3$)$_2$Cl$_2$ (8.7 g, 12.4 mmol), and CuI (4.72 g, 24.8 mmol), 750 mL of DMF and 750 mL of TEA were added. The solution was purged and refilled with Ar three times under sonication. The solution was stirred at 80° C. overnight. Then to the reaction was added water and extracted with ethyl acetate. The combined ethyl acetate (about 5) layers were washed with brine three times. Then the resulting precipitate was filtered, washed with hexane to give Intermediate 7. For further purification, methanol was added to the product and the mixture was stirred for 10 min. Then the precipitate was filtered, and washed with hexane to give the pure Intermediate 7 (70-80% yield, purity >95%).

3-(1-oxo-4-(piperidin-4-ylethynyl)isoindolin-2-yl)piperidine-2,6-dione (Intermediate 4): The above obtained Intermediate 7 (30 g) was suspended in HCl in dioxane (150 mL). The solution was stirred at room temperature for 30 min. Then the resulting precipitate was filtered, washed with hexane to give the pure Intermediate 4 (90% yield, purity >95%). MS(ESI) m/z (M+H)$^+$=352.31; calcd: 351.41; R$_f$=1.04 min; $^1$H NMR (400 MHz, methanol-d$_4$) δ 7.79 (dd, J=7.6, 1.0 Hz, 1H), 7.67 (dd, J=7.7, 1.0 Hz, 1H), 7.53 (t, J=7.7 Hz, 1H), 5.19 (dd, J=13.3, 5.1 Hz, 1H), 4.59-4.41 (m, 2H), 3.47-3.36 (m, 2H), 3.24-3.09 (m, 3H), 3.00-2.85 (m, 1H), 2.84-2.73 (m, 1H), 2.53 (qd, J=13.2, 4.6 Hz, 1H), 2.26-2.13 (m, 3H), 2.04-1.90 (m, 2H).

Example 3

Synthesis of tert-butyl 4-ethynylpiperidine-1-carboxylate (Intermediate 5)

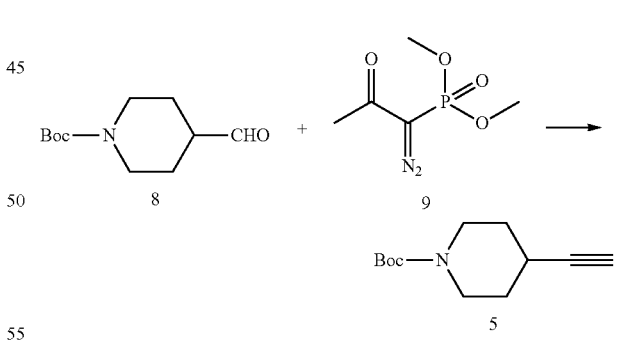

K$_2$CO$_3$ (260 g) was added to a solution of N-Boc-piperidine-4-aldehyde (100 g) in MeOH (500 mL) at 0° C. Then dimethyl 1-diazoacetonylphosphonate (108 g) was slowly added at 0° C. After stirring at room temperature for 4 h, the mixture was quenched with water, then most of the MeOH was removed by rotary evaporation. The residue was extracted with ethyl acetate, and the organic layer washed with brine, dried with Na$_2$SO$_4$, and concentrated to give Intermediate 5 which was used in next step without further purification.

Example 4

Synthesis of 3-(4-bromo-1-oxoisoindolin-2-yl)piperidine-2,6-dione (Intermediate 6)

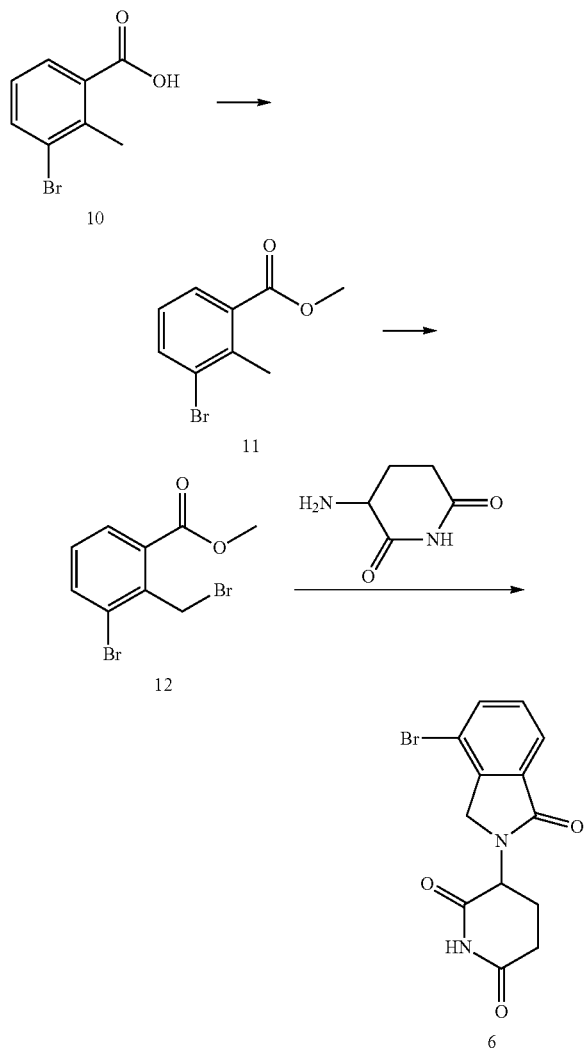

To a solution of Intermediate 10 (150 g) in MeOH (1500 mL) was added conc. $H_2SO_4$ (80 mL) dropwise. The reaction mixture was stirred overnight at reflux. After cooling to room temperature, the MeOH was removed by rotary evaporation. Then water was added, and the mixture was extracted with $Et_2O$ three times. The organic layer was washed with brine, dried with $Na_2SO_4$, filtered and concentrated to give the crude product Intermediate 11 which was used in next step without further purification.

To a solution of Intermediate 11 (160 g) in benzene (1300 mL) was added N-bromosuccinamide (149 g) and benzoyl peroxide (16 g). The reaction mixture was stirred overnight at reflux. After cooling to room temperature, aqueous $Na_2S_2O_3$ was added and the mixture was stirred for 10-20 min at room temperature. The mixture was extracted with benzene two times. The organic layer was washed with brine, dried with $Na_2SO_4$, filtered and concentrated to give the crude product. Then ethyl acetate was added and the mixture was stirred for several minutes. The resulting precipitate was filtered, and the filtrate was concentrated to give the product Intermediate 12 which was used in the next step without further purification.

To a solution of Intermediate 12 (183 g) in $CH_3CN$ (1000 mL) was added 3-aminopiperidine-2,6-dione (1.2 eq) and triethylamine (80 g) and the reaction mixture was stirred at 80° C. After complete consumption of Intermediate 12 as detected by TLC, the mixture was cooled to room temperature then ethyl acetate (1000 mL) and water (1000 mL) were added. The mixture was stirred for 10-20 min, and the resulting precipitate was filtered, and washed with hexane. The solid was then dried in a desiccator under vacuum (overnight) to produce Intermediate 6 (142 g) as a solid, which was used in next step without further purification.

Example 5

The following Compounds of the Disclosure were prepare using the procedures described in Examples 1-4 and WO 2017/176957, and methods known in the art.

Cpd No. 1: LC-MS(ESI) m/z (M+H)$^+$=996.00; calcd: 996.02; $R_t$=4.00 min.

Cpd. No. 2: LC-MS(ESI) m/z (M+H)$^+$=921.46; calcd: 921.89; $R_t$=5.16 min.

Cpd. No. 3: LC-MS(ESI) m/z (M+H)$^+$=897.53; calcd: 897.87; $R_t$=4.98 min; $^1$H NMR (400 MHz, methanol-d$_4$) δ 7.74 (dd, J=7.7, 1.1 Hz, 1H), 7.63-7.54 (m, 3H), 7.49 (t, J=7.6 Hz, 1H), 7.41 (t, J=7.2 Hz, 1H), 7.21-7.12 (m, 2H), 6.80 (d, J=1.8 Hz, 1H), 5.24-5.11 (m, 2H), 4.62-4.42 (m, 4H), 3.69-3.55 (m, 1H), 3.01-2.85 (m, 2H), 2.85-2.74 (m, 1H), 2.67-2.54 (m, 1H), 2.51 (t, J=6.8 Hz, 2H), 2.24-2.13 (m, 1H), 2.10-1.98 (m, 1H), 1.98-1.67 (m, 7H), 1.64-1.40 (m, 4H), 1.25-1.10 (m, 2H), 0.88 (s, 9H).

Cpd. No. 5: LC-MS(ESI) m/z (M+H)$^+$=936.54; calcd: 936.91; $R_t$=4.06 min.

Cpd. No. 6: LC-MS(ESI) m/z (M+H)$^+$=947.54; calcd: 947.93; $R_t$=5.44 min; $^1$H NMR (400 MHz, methanol-d$_4$) δ 7.76 (dd, J=7.6, 1.1 Hz, 1H), 7.71-7.58 (m, 3H), 7.55-7.44 (m, 2H), 7.40 (ddd, J=8.6, 7.3, 1.6 Hz, 1H), 7.16 (td, J=8.0, 1.2 Hz, 1H), 7.10 (dd, J=8.2, 2.0 Hz, 1H), 6.78 (d, J=2.0 Hz, 1H), 5.17 (dd, J=13.3, 5.2 Hz, 1H), 5.11 (d, J=11.2 Hz, 1H), 4.72 (d, J=11.2 Hz, 1H), 4.55-4.40 (m, 2H), 4.06-3.91 (m, 2H), 3.40 (t, J=10.3 Hz, 2H), 3.05-2.85 (m, 2H), 2.85-2.72 (m, 2H), 2.53 (qd, J=13.3, 4.7 Hz, 1H), 2.25-2.12 (m, 2H), 2.02-1.71 (m, 19H), 1.71-1.59 (m, 2H), 1.59-1.44 (m, 1H), 1.31-1.13 (m, 2H).

Cpd. No. 7: LC-MS(ESI) m/z (M+H)$^+$=922.52; calcd: 922.88; $R_t$=4.24 min.

Cpd. No. 8: LC-MS(ESI) m/z (M+H)$^+$=938.54; calcd: 938.92; $R_t$=4.38 min.

Cpd. No. 9: LC-MS(ESI) m/z (M+H)$^+$=935.52; calcd: 935.92; $R_t$=5.47 min.

Cpd. No. 10: LC-MS(ESI) m/z (M+H)$^+$=961.54; calcd: 961.96; $R_t$=5.92 min.

Cpd. No. 11: LC-MS(ESI) m/z (M+H)$^+$=905.50; calcd: 905.85; $R_t$=5.07 min; $^1$H NMR (400 MHz, methanol-d$_4$) δ 7.76 (dd, J=7.7, 1.0 Hz, 1H), 7.66-7.58 (m, 2H), 7.54-7.46 (m, 2H), 7.39 (ddd, J=8.5, 7.3, 1.5 Hz, 1H), 7.16 (td, J=8.1, 1.2 Hz, 1H), 7.11 (dd, J=8.2, 2.0 Hz, 1H), 6.78 (d, J=1.9 Hz, 1H), 5.17 (dd, J=13.3, 5.2 Hz, 1H), 5.00 (d, J=11.0 Hz, 1H), 4.79 (d, J=11.0 Hz, 1H), 4.58-4.41 (m, 2H), 4.00-3.84 (m, 2H), 3.55-3.44 (m, 1H), 3.42-3.33 (m, 1H), 3.08-2.96 (m, 1H), 2.97-2.86 (m, 1H), 2.86-2.73 (m, 2H), 2.53 (qd, J=13.2, 4.7 Hz, 1H), 2.37 (s, 6H), 2.24-2.08 (m, 2H), 2.03-1.81 (m, 5H), 1.81-1.60 (m, 4H), 1.58-1.42 (m, 1H), 1.29-1.13 (m, 2H).

Cpd. No. 12: LC-MS(ESI) m/z (M+H)$^+$=893.48; calcd: 893.84; $R_t$=4.85 min; $^1$H NMR (400 MHz, methanol-$d_4$) δ 7.76 (dd, J=7.6, 1.1 Hz, 1H), 7.69-7.60 (m, 2H), 7.55-7.46 (m, 2H), 7.40 (ddd, J=8.5, 7.2, 1.5 Hz, 1H), 7.19 (td, J=8.1, 1.2 Hz, 1H), 7.10 (dd, J=8.2, 2.0 Hz, 1H), 6.79 (d, J=1.9 Hz, 1H), 5.18 (dd, J=13.3, 5.2 Hz, 1H), 5.07 (d, J=11.0 Hz, 1H), 4.80 (dd, J=11.1, 2.1 Hz, 1H), 4.57-4.41 (m, 2H), 4.30 (p, J=7.6 Hz, 1H), 4.04-3.87 (m, 1H), 3.61-3.50 (m, 1H), 3.46-3.35 (m, 1H), 3.29-3.15 (m, 2H), 3.05-2.85 (m, 2H), 2.85-2.73 (m, 2H), 2.65-2.40 (m, 3H), 2.24-2.11 (m, 3H), 2.06-1.80 (m, 6H), 1.76 (d, J=12.6 Hz, 2H), 1.73-1.58 (m, 2H), 1.51 (q, J=13.8 Hz, 1H), 1.27-1.13 (m, 2H).

Cpd. No. 13: LC-MS(ESI) m/z (M+H)$^+$=945.55; calcd: 975.98; $R_t$=6.01 min; $^1$H NMR (400 MHz, methanol-$d_4$) δ 7.76 (dd, J=7.7, 1.1 Hz, 1H), 7.70 (s, 1H), 7.67-7.60 (m, 2H), 7.55-7.46 (m, 2H), 7.40 (ddd, J=8.5, 7.2, 1.5 Hz, 1H), 7.16 (td, J=8.1, 1.2 Hz, 1H), 7.11 (dd, J=8.3, 2.0 Hz, 1H), 6.80 (d, J=1.9 Hz, 1H), 5.17 (dd, J=13.3, 5.2 Hz, 1H), 5.09 (d, J=11.1 Hz, 1H), 4.72 (d, J=11.1 Hz, 1H), 4.56-4.40 (m, 2H), 4.06-3.92 (m, 2H), 3.40 (t, J=10.8 Hz, 2H), 3.06-2.84 (m, 2H), 2.84-2.73 (m, 1H), 2.68 (d, J=14.1 Hz, 1H), 2.53 (qd, J=13.2, 4.7 Hz, 1H), 2.24-2.12 (m, 1H), 2.13-2.00 (m, 2H), 2.00-1.87 (m, 8H), 1.85 (d, J=3.4 Hz, 1H), 1.84-1.72 (m, 6H), 1.71-1.56 (m, 3H), 1.50-1.28 (m, 3H), 1.01 (s, 3H), 0.76 (s, 3H).

Cpd. No. 14: LC-MS(ESI) m/z (M+H)$^+$=931.58; calcd: 931.48; $R_t$=5.27 min; $^1$H NMR (400 MHz, methanol-$d_4$) δ 7.76 (dd, J=7.7, 1.1 Hz, 1H), 7.68 (s, 1H), 7.62 (dd, J=7.7, 1.1 Hz, 1H), 7.55-7.44 (m, 3H), 7.25-7.11 (m, 2H), 7.10 (dd, J=8.2, 2.0 Hz, 1H), 6.78 (d, J=2.0 Hz, 1H), 5.17 (dd, J=13.3, 5.2 Hz, 1H), 5.11 (d, J=11.2 Hz, 1H), 4.70 (d, J=11.2 Hz, 1H), 4.56-4.41 (m, 2H), 4.05-3.91 (m, 2H), 3.40 (t, J=11.1 Hz, 2H), 3.05-2.85 (m, 2H), 2.85-2.74 (m, 2H), 2.53 (qd, J=13.2, 4.7 Hz, 1H), 2.23-2.13 (m, 2H), 2.02-1.84 (m, 11H), 1.86-1.71 (m, 8H), 1.72-1.58 (m, 2H), 1.52 (q, J=13.7 Hz, 1H), 1.30-1.13 (m, 2H).

Cpd. No. 15: LC-MS(ESI) m/z (M+H)$^+$=935.52; calcd: 935.92; $R_t$=4.81 min.

Cpd. No. 16: LC-MS(ESI) m/z (M+H)$^+$=949.54; calcd: 949.95; $R_t$=4.86 min.

Cpd. No. 17: LC-MS(ESI) m/z (M+H)$^+$=905.54; calcd: 905.44; $R_t$=4.83 min; $^1$H NMR (400 MHz, methanol-$d_4$) δ 8.18 (d, J=7.8 Hz, 1H), 7.76 (dd, J=7.7, 1.1 Hz, 1H), 7.62 (dd, J=7.7, 1.1 Hz, 1H), 7.55-7.45 (m, 3H), 7.24-7.11 (m, 3H), 7.10 (dd, J=8.2, 2.0 Hz, 1H), 6.78 (d, J=1.9 Hz, 1H), 5.16 (dd, J=13.3, 5.2 Hz, 1H), 5.12 (d, J=11.1 Hz, 1H), 4.78 (d, J=11.2 Hz, 1H), 4.56-4.40 (m, 2H), 4.02-3.90 (m, 1H), 3.86-3.75 (m, 1H), 3.73-3.59 (m, 1H), 3.46-3.34 (m, 2H), 3.05-2.82 (m, 3H), 2.84-2.73 (m, 1H), 2.63-2.44 (m, 2H), 2.25-2.12 (m, 2H), 2.05-1.83 (m, 7H), 1.83-1.43 (m, 11H), 1.34-1.16 (m, 3H), 1.03-0.88 (m, 1H).

Cpd. No. 22: LC-MS(ESI) m/z (M+H)$^+$=935.48; calcd: 935.92; $R_t$=4.73 min.

Cpd. No. 23: LC-MS(ESI) m/z (M+H)$^+$=907.48; calcd: 907.87; $R_t$=4.60 min.

Cpd. No. 24: LC-MS(ESI) m/z (M+H)$^+$=943.47; calcd: 943.90; $R_t$=6.42 min.

Cpd. No. 25: LC-MS(ESI) m/z (M+H)$^+$=861.56; calcd: 861.41; $R_t$=4.36 min.

Cpd. No. 26: LC-MS(ESI) m/z (M+H)$^+$=877.53; calcd: 877.86; $R_t$=4.60 min.

Cpd. No. 27: LC-MS(ESI) m/z (M+H)$^+$=843.55; calcd: 843.42; $R_t$=4.18 min.

Cpd. No. 28: LC-MS(ESI) m/z (M+H)$^+$=945.48; calcd: 945.87; $R_t$=6.24 min.

Cpd. No. 29: LC-MS(ESI) m/z (M+H)$^+$=921.57; calcd: 921.89; $R_t$=4.70 min.

Cpd. No. 30: LC-MS(ESI) m/z (M+H)$^+$=935.56; calcd: 935.92; $R_t$=5.27 min.

Cpd. No. 31: LC-MS(ESI) m/z (M+H)$^+$=961.59; calcd: 961.96; $R_t$=5.81 min.

Cpd. No. 32: LC-MS(ESI) m/z (M+H)$^+$=893.53; calcd: 893.84; $R_t$=4.62 min.

Cpd. No. 33: LC-MS(ESI) m/z (M+H)$^+$=919.54; calcd: 919.88; $R_t$=4.93 min.

Cpd. No. 34: LC-MS(ESI) m/z (M+H)$^+$=1178.07; calcd: 1178.30; $R_t$=6.72 min.

Cpd. No. 35: LC-MS(ESI) m/z (M+2H)$^+$=629.12; calcd: 629.16; $R_t$=5.63 min.

Cpd. No. 36: LC-MS(ESI) m/z (M+2H)$^+$=635.46; calcd: 635.66; $R_t$=5.05 min.

Cpd. No. 37: LC-MS(ESI) m/z (M+H)$^+$=875.45; calcd: 875.90; $R_t$=6.11 min.

Cpd. No. 38 LC-MS(ESI) m/z (M+H)$^+$=951.52; calcd: 951.94; $R_t$=7.33 min; $^1$H NMR (400 MHz, methanol-$d_4$) δ 7.90 (s, 1H), 7.76 (dd, J=7.6, 1.0 Hz, 1H), 7.67-7.60 (m, 2H), 7.51 (t, J=7.6 Hz, 1H), 7.41-7.35 (m, 2H), 7.32 (t, J=8.4 Hz, 1H), 7.27-7.16 (m, 2H), 5.17 (dd, J=13.3, 5.2 Hz, 1H), 4.70 (d, J=7.8 Hz, 1H), 4.57-4.42 (m, 2H), 4.31 (d, J=7.7 Hz, 1H), 4.10-3.99 (m, 2H), 3.94 (d, J=9.3 Hz, 1H), 3.48-3.38 (m, 2H), 3.07-2.97 (m, 1H), 2.98-2.84 (m, 2H), 2.84-2.72 (m, 2H), 2.54 (qd, J=13.3, 4.7 Hz, 2H), 2.19 (ddq, J=10.4, 5.3, 2.6 Hz, 1H), 2.06-1.91 (m, 10H), 1.75-1.57 (m, 3H), 1.35-1.26 (m, 2H), 0.93 (s, 9H).

Example 6

Cell Growth Inhibition

The effect of representative Compounds of the Disclosure on cell viability was determined in a 4-day proliferation assay. See Tables 4. Cells were maintained in the appropriate culture medium with 10% FBS at 37° C. and an atmosphere of 5% CO$_2$. Also, the effect of a MDM2 inhibitor (Cpd. A; see Compound Example No. 22 of U.S. Pat. No. 8,629,141) and a known MDM2 degrader (Cpd. D, see Cpd. No. 175 of WO 2017/0176957) on cell viability in various cell lines is also included in Table 5. Cpd. Nos. 4 and 6 of the instant disclosure are surprisingly more potent in all cell lines tested as compared to Cpds. A and D. The structure of Cpd. A is:

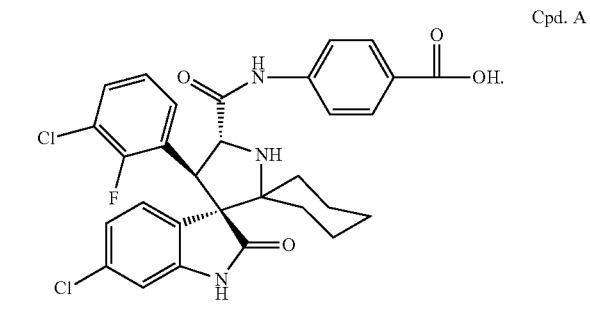 [SMILES: O=C(O)c1ccc(NC(=O)[C@@H]2NC3(CCCCC3)[C@@]3(C(=O)Nc4cc(Cl)ccc43)[C@H]2c2cccc(Cl)c2F)cc1]

The structure of Cpd. D is:

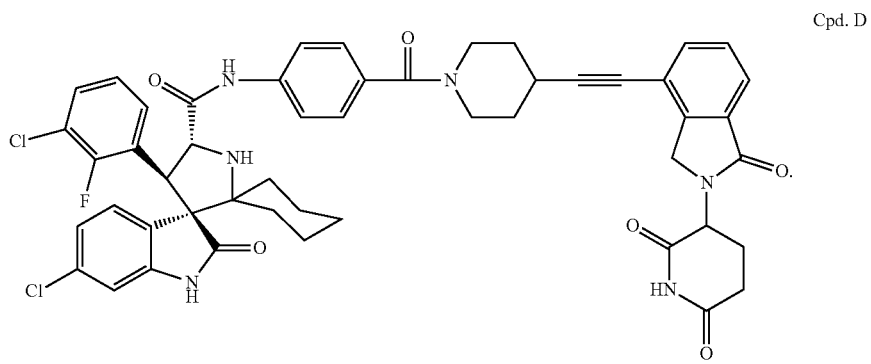 [SMILES: O=C1CCC(N2Cc3c(C#CC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1]

Cpd. D

Cells were seeded in 96-well flat bottom (Corning COSTAR, Corning, N.Y., cat #3595) at a density of 2,000-3,000 cells/well in 100 μL of culture medium. Compounds were serially diluted in the appropriate medium, and 100 μL of the diluted compounds were added to the appropriate wells of the cell plate. After the addition of compounds, the cells were incubated at 37° C. in an atmosphere of 5% $CO_2$ for 4 days. Cell viability was determined using the WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) according to the manufacturers' instructions.

WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration ($IC_{50}$) was calculated by nonlinear regression (four parameters sigmoid fitted with variable slope, least squares fit, and no constraint) analysis using the GraphPad Prism 5 software (GraphPad Software, La Jolla, Calif.).

TABLE 4

| Cpd. No. | RS4; 11 Cells $IC_{50}$ (nM) |
|---|---|
| 1 | 2.4 |
| 2 | 4.7 |
| 3 | 0.62 |
| 5 | 3.1 |
| 7 | >100 |
| 8 | 4.5 |
| 9 | 2.8 |
| 10 | 8.0 |
| 11 | 0.3 |
| 12 | 1.4 |
| 13 | 6 |
| 14 | 11 |
| 15 | 60 |
| 16 | >100 |
| 22 | >100 |
| 23 | >100 |
| 24 | 6.6 |
| 25 | >100 |
| 26 | 0.7 |
| 27 | >100 |
| 28 | >100 |
| 29 | >100 |
| 30 | 1.2 |
| 31 | 2.9 |
| 32 | 1.3 |
| 33 | 1.2 |
| 37 | >100 |
| 38 | 56 |

TABLE 5

| Cell line | Cell Type | $IC_{50}$ (μM) Cpd. A | Cpd. D | Cpd. No. 4 | Cpd. No. 6 |
|---|---|---|---|---|---|
| RS4; 11 | Precursor cell lymphoblastic leukemia | 0.138 | 0.0029 | 0.00072 | 0.0024 |
| MV-4; 11 | Acute biphenotypic B myelomonocytic leukemia | | 0.01 | 0.0023 | 0.0064 |
| OCI-AML-2 | Acute myeloid leukemia | | 0.11 | 0.021 | 0.069 |
| OCI-AML-5 | Acute myeloid leukemia | | 0.15 | 0.023 | 0.071 |
| MOLM-13 | Acute myeloid leukemia | | 0.034 | 0.0051 | 0.018 |
| MOLM-14 | Acute myeloid leukemia | | 0.078 | 0.0078 | 0.025 |
| ML-2 | Acute myeloid leukemia | | 0.011 | 0.0012 | 0.0049 |
| SIG-M5 | Acute myeloid leukemia | | 0.11 | 0.021 | 0.063 |
| LNCaP | Prostate carcinoma | | 0.033 | 0.0032 | 0.013 |
| 22RV1 | Prostate carcinoma | 1.327 | 0.045 | 0.014 | 0.042 |
| HCT116 | Colorectal carcinoma | | 0.4 | 0.086 | 0.31 |

Example 7

In Vivo Efficacy Studies in the LNCaP and 22Rv1 Human Prostate Xenograft Models

LNCaP (human prostate) tumor cells were harvested with Trypsin (0.25%)-EDTA (0.53 mM) (GIBCO™, Invitrogen Corp.), growth medium added and cells placed on ice. A cell sample was mixed 1:1 with Trypan Blue (GIBCO™ Invitrogen Corp.) and counted on a hemocytometer to determine the number of live/dead cells. Cells were washed twice with 1×PBS (GIBCO™, Invitrogen Corp.) and resuspended in an ice cold mixture of 1:1 PBS and Matrigel (BD Biosciences, Invitrogen Corp.) for a final Matrigel protein concentration of 5 mg/ml. LNCaP tumors were inoculated into male C.B-17 SCID mice at 5×10⁶ cells in 0.1 ml with Matrigel. Cells were injected s.c. into the flank region of each mouse. The size of tumors growing in the mice was measured in two dimensions using calipers. Tumor volume $(mm^3)=(A \times B^2)/2$ where A and B are the tumor length and width (in mm), respectively. During treatment, tumor volume and body weight was measured two or three times a week. After the treatment was stopped, tumor volume and body weight was measured at least once a week. Before treatment began, tumors were allowed to grow to 100-200 mm³ in volume. Mice with tumors within acceptable size range were randomized into treatment groups of 7 mice per group. Experimental compounds were given intravenously, in a solution of 25% PEG 400: 9% Cremophor EL: 66% PBS), once per week for 5 weeks. Using similar protocols, the antitumor activity of Cpd. No. 4 and Cpd. No. 6 was evaluated in the 22Rv1 human prostate cancer model in mice. See FIG. 1 and FIG. 2.

Example 8

In Vivo Efficacy Studies in the RS4;11 Human ALL Xenograft Model

RS4;11 tumors were grown in suspension. A cell sample was mixed 1:1 with Trypan Blue (GIBCO™, Invitrogen Corp.) and counted on a hemocytometer to determine the number of live/dead cells. Cells were washed twice with 1×PBS (GIBCO™, Invitrogen Corp.) and resuspended in an ice cold mixture of 1:1 PBS and Matrigel (BD Biosciences, Invitrogen Corp.) for a final Matrigel protein concentration of 5 mg/mL. RS4;11 tumors were inoculated into female C.B-17 SCID mice at 5×10⁶ cells in 0.1 mL with Matrigel. Cells were injected s.c. into the flank region of each mouse. The size of tumors growing in the mice was measured in two dimensions using calipers. Tumor volume $(mm^3)=(A \times B^2)/2$ where A and B are the tumor length and width (in mm), respectively. During treatment, tumor volume and body weight was measured two or three times a week. After the treatment was stopped, tumor volume and body weight was measured at least once a week. Before treatment began, tumors were allowed to grow to 60-140 mm³ in volume. Mice with tumors within acceptable size range were randomized into treatment groups of 5 mice per group. Cpd. No. 4 and Cpd. No. 6 were given intravenously, in a solution of 25% PEG 400: 9% Cremophor EL: 66% PBS, three times per week for 2 weeks and orally in a solution of PEG 200, 5 times per week for 2 weeks. See FIG. 3.

Example 9

Survival Studies

Conditioning

Female NOD SCID (NOD.CB17-Prkdc$^{scid}$/NCrHsd) mice were obtained from Envigo, USA. At 8-10 weeks old, the mice were pretreated with 150 mg/kg cyclophosphamide (CPM) (NDC 10019-956-01 Baxter Healthcare Corporation, Deerfield, Ill.) obtained from the UM Hospital Pharmacy and dissolved to a concentration of 15 mg/mL with sterile saline (0.9% sodium chloride NDC 0409-4888-06). The mice were injected IP, with a volume of 10 ul/g body weight, on two days 24 hours apart. At the start of conditioning, diet gel was provided in each cage to mitigate the effects of treatment and subsequently supplied throughout the experiment.

Cell Inoculation

On the following day, 24 hours after the second dose of CPM, each animal was injected with 5×10⁶ RS4;11 cells in 0.15 mL via the lateral tail vein. RS4;11 cells were obtained from ATCC (certified free of mouse and human virus), grown in RPMI medium supplemented with penicillin/streptomycin (Lifetech) and 10% fetal bovine serum (Sigma) in a 5% $CO_2$ incubator. For injection, cells were washed twice in PBS and resuspended in sterile saline at a concentration of 3.3×10⁷ RS4;11 cells per mL.

Treatment

Thirteen days after cell injection, mice were randomized into treatment groups of 9-10 mice and allowed to acclimate to their cage mates. The following day, two weeks following cell injection (treatment day 1, tumor day 15) treatment was started. Cpd. No. 4 and Cpd. No. 6 were given intravenously, in a solution of 25% PEG 400: 9% Cremophor EL: 66% PBS, and orally in a solution of PEG 200.

Assessment

Mice were checked daily and weighed 3 times per week. When the first signs of illness appeared all mice were weighed daily thereafter. Signs of impending illness were weight loss, hunched and scruffy or pale appearance, decreased mobility, partial paralysis in hind limbs, distended abdomen, eye problems, respiratory problems. An animal was euthanized when there was either >20% weight loss, full hind limb paralysis, or the presence of several symptoms in one individual. Mice were euthanized with $CO_2$ overdose. The spleen was removed, photographed with a ruler, weighed and divided into 3 portions for 1) formalin fixation for paraffin sections 2) embedding in a mold in OCT medium for frozen sections 3) liquid nitrogen snap freezing pieces in a microfuge tube for later analysis. The sternum was removed and fixed in formalin for bone marrow paraffin sections. See FIG. 4 and FIG. 5.

Example 10

Western Blot Analysis

RS4;11 cells were treated with Cpd. No. 4 and Cpd. No. 6 (MDM2 degraders) or with Cpd. B and Cpd. C (MDM2 inhibitors) for 2 hr. MDM2 and p53 proteins were probed using specific antibodies. GAPDH was used as the loading control. Western blot analysis in shows that Cpd. No. 4 and Cpd. No. 6 reduce MDM2 protein and increase p53 protein level, and that Cpd. B and Cpd. C increase MDM2 and p53 protein levels in RS4;11 cells. See FIG. 6. The structures of Cpd. B (see Compound Example No. 24 of U.S. Pat. No. 8,629,141) and Cpd. C are:

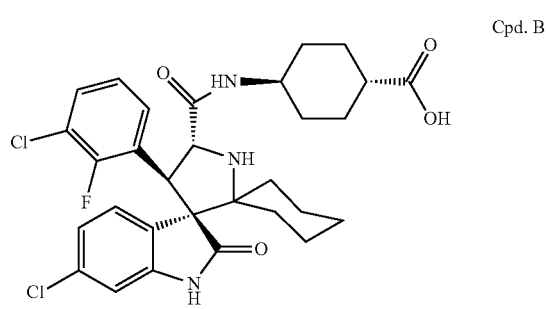

Cpd. B

-continued

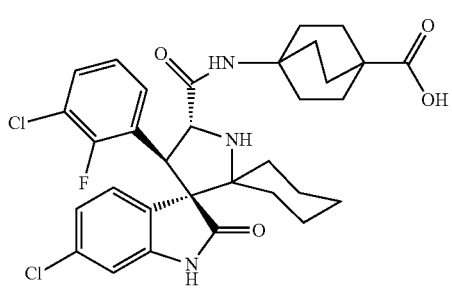

Cpd. C

22RV1 cells were treated with Cpd. No. 4 and Cpd. D (MDM2 degraders) or with Cpd. A (MDM2 inhibitor) for 2 hr. MDM2 and p53 proteins were probed using specific antibodies. GAPDH was used as the loading control. Western blot analysis in shows that Cpd. No. 4 and Cpd. D reduce MDM2 protein and increase p53 protein level, and that Cpd. A increases MDM2 and p53 protein levels in 22RV1 cells. See FIG. 7.

Example 11

Pharmacokinetics

The pharmacokinetics of Cpd. Nos. 4 and 6, and Cpd. D were evaluated in mice. The oral and IV dose amounts and relevant pharmacokinetic parameters are provided in Table 6.

TABLE 6

| Compound | Route | DOSE (mg/kg) | AUC (h * ng/mL) | F (%) |
|---|---|---|---|---|
| Cpd. D | IV | 10 | 193480 | |
| | PO | 50 | 12277 | 1.27 |
| Cpd No. 4 | IV | 10 | 155561 | |
| | PO | 50 | 7248 | 0.93 |
| Cpd No. 6 | IV | 10 | 153758 | |
| | PO | 50 | 43544 | 5.7 |

In a separate PK experiment, the plasma concentrations of Cpd. D, and Cpd Nos. 4, 6, and 14 were evaluated in mice following an oral dose of 50 mg/kg at the time points indicated in Tables 7-10, respectively.

TABLE 7

| | Plasma PO 50 mg/kg | | |
|---|---|---|---|
| | Mouse 1 | Mouse 2 | Average |
| | | Cpd. D | |
| Time (h) | Concentration (ng/mL) | | |
| 1 | 78.0 | 77.8 | 77.9 |
| 3 | 510 | 738 | 624 |
| 6 | 234 | 594 | 414 |

TABLE 8

| | Plasma PO 50 mg/kg | | | |
|---|---|---|---|---|
| | Mouse 1 | Mouse 2 | Mean | SD |
| | | | Cpd. No. 4 | |
| Time (h) | Concentration (ng/mL) | | | |
| 1 | 0.231 | 1.01 | 0.62 | 0.55 |
| 3 | 902 | 1730 | 1316.00 | 585.48 |
| 6 | 231 | 446 | 338.50 | 152.03 |

TABLE 9

| | Plasma PO 50 mg/kg | | | |
|---|---|---|---|---|
| | Mouse 1 | Mouse 2 | Mean | SD |
| | | | Cpd. No. 6 | |
| Time (h) | Concentration (ng/mL) | | | |
| 1 | 0.576 | 0.257 | 0.42 | 0.23 |
| 3 | 3110 | 3330 | 3220.00 | 155.56 |
| 6 | 2320 | 2430 | 2375.00 | 77.78 |

TABLE 10

| | Plasma PO 50 mg/kg | | |
|---|---|---|---|
| | Mouse 1 | Mouse 2 | Average |
| | | Cpd. No. 14 | |
| Time (h) | Concentration (ng/mL) | | |
| 1 | 4060 | 2550 | 3305 |
| 3 | 6880 | 8050 | 7465 |
| 6 | 7660 | 8810 | 8235 |

It is to be understood that the foregoing embodiments and exemplifications are not intended to be limiting in any respect to the scope of the disclosure, and that the claims presented herein are intended to encompass all embodiments and exemplifications whether or not explicitly presented herein.

All patents and publications cited herein are fully incorporated by reference in their entirety.

What is claimed is:

1. A compound of Formula I:

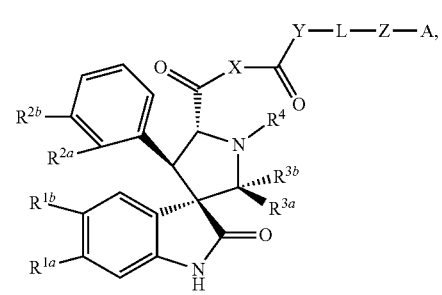

wherein:

$R^{1a}$ and $R^{1b}$ are independently selected from the group consisting of hydrogen, fluoro, and chloro;

$R^{2a}$ and $R^{2b}$ are independently selected from the group consisting of hydrogen, fluoro, and chloro;

$R^{3a}$ is —$CH_2C(CH_3)_3$;

$R^{3b}$ is hydrogen; or $R^{3a}$ and $R^{3b}$ taken together with the carbon atom to which they are attached form a cyclobutyl, cyclopentyl, or cyclohexyl group that is unsubstituted or substituted with one or two methyl groups;

$R^4$ is selected from the group consisting of hydrogen, methyl, and ethyl;

X is selected from the group consisting of:

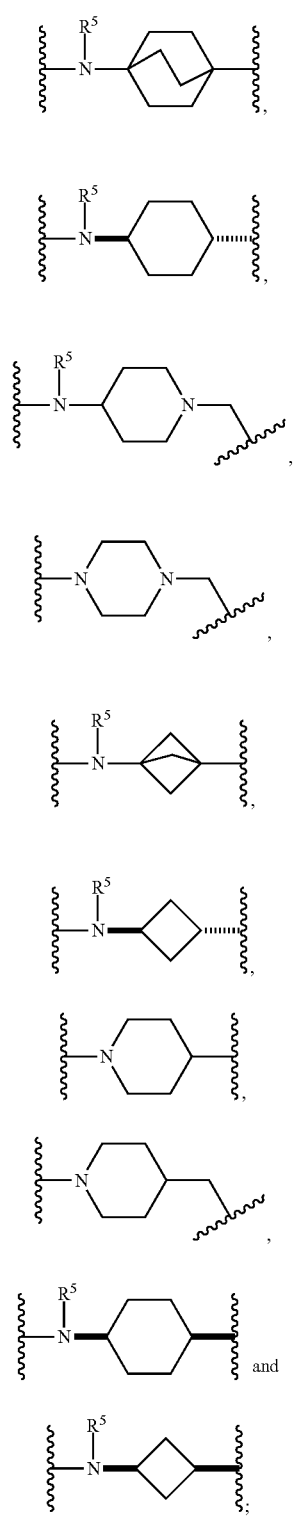

wherein the bond projecting to the right is attached to —C(=O)—Y—L-Z-A;

each R⁵ is independently selected from the group consisting of hydrogen and methyl;

Y is selected from the group consisting of:

—N(H)—,

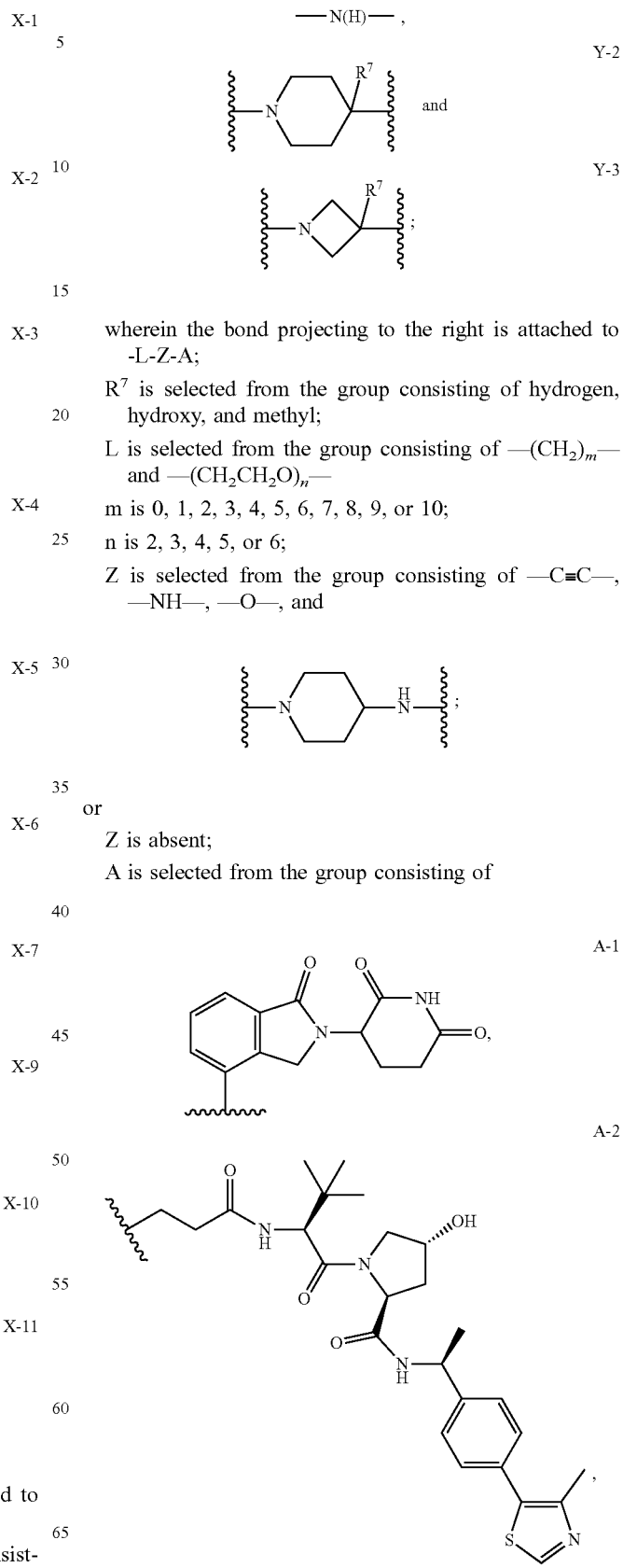

wherein the bond projecting to the right is attached to -L-Z-A;

$R^7$ is selected from the group consisting of hydrogen, hydroxy, and methyl;

L is selected from the group consisting of —(CH$_2$)$_m$— and —(CH$_2$CH$_2$O)$_n$— m is 0, 1, 2, 3, 4, 5, 6, 7, 8, 9, or 10;

n is 2, 3, 4, 5, or 6;

Z is selected from the group consisting of —C≡C—, —NH—, —O—, and or

Z is absent;

A is selected from the group consisting of

A-3
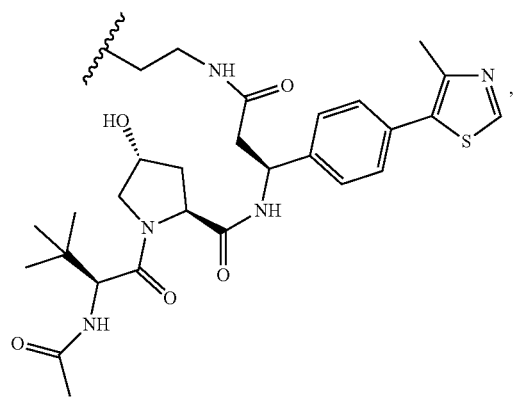
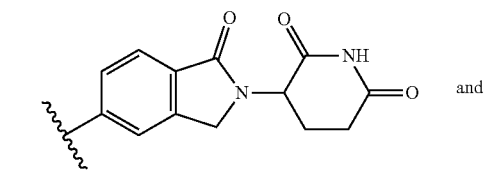
and
A-5
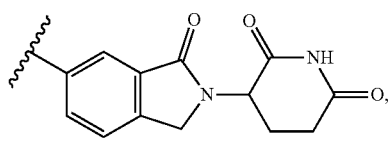
or a pharmaceutically acceptable salt or solvate thereof.
2. The compound of claim 1 of Formula II:
II
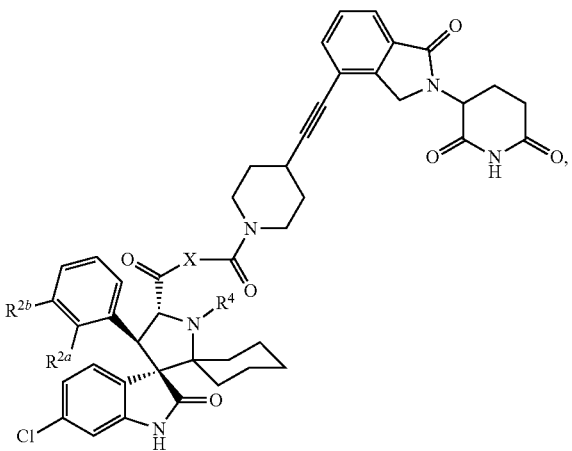
or a pharmaceutically acceptable salt or solvate thereof.
3. The compound of claim 1 selected from the group consisting of
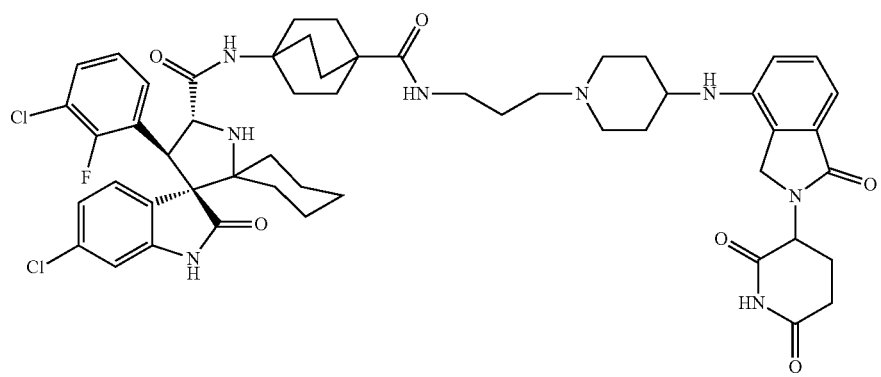
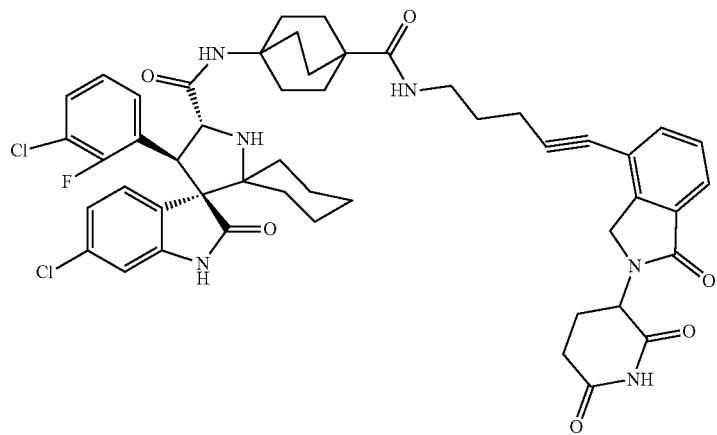

-continued
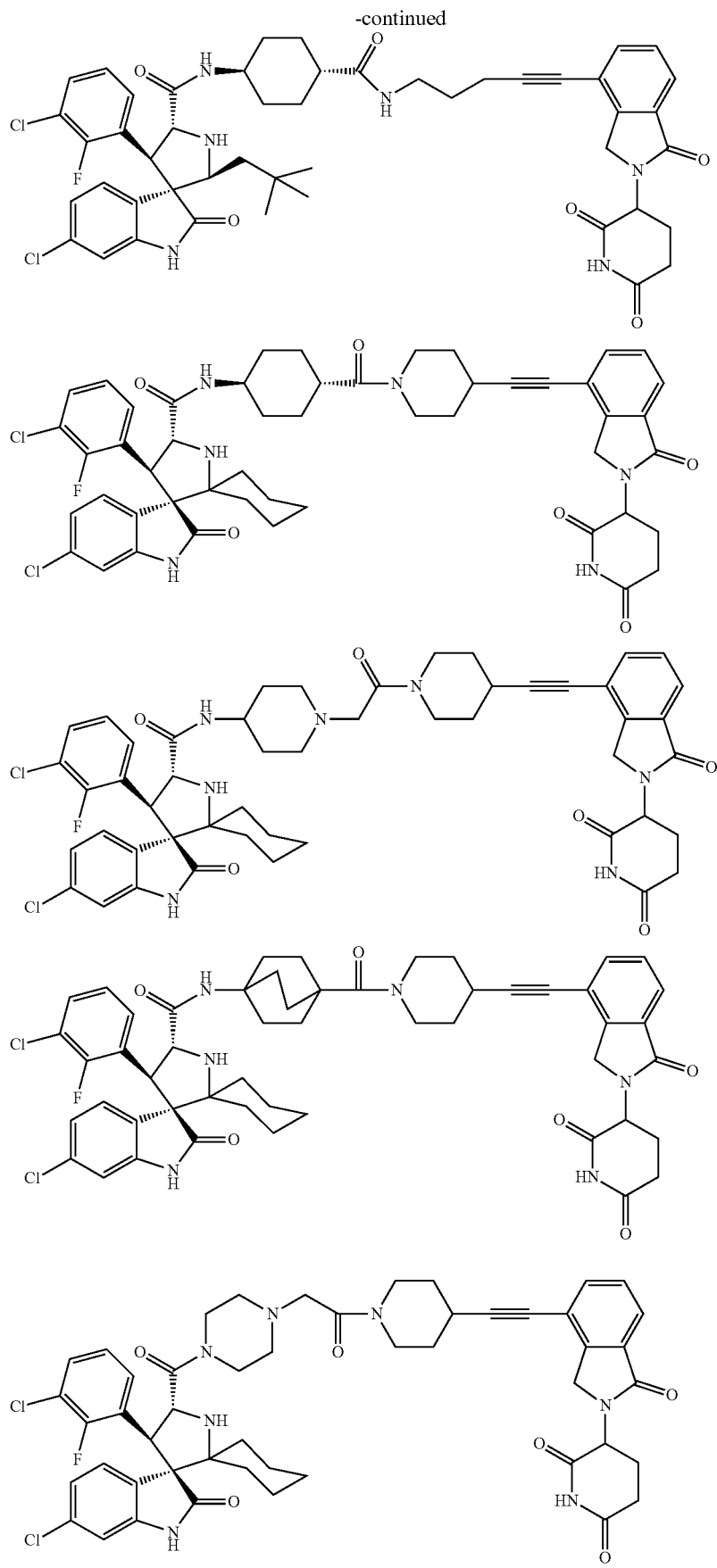

-continued
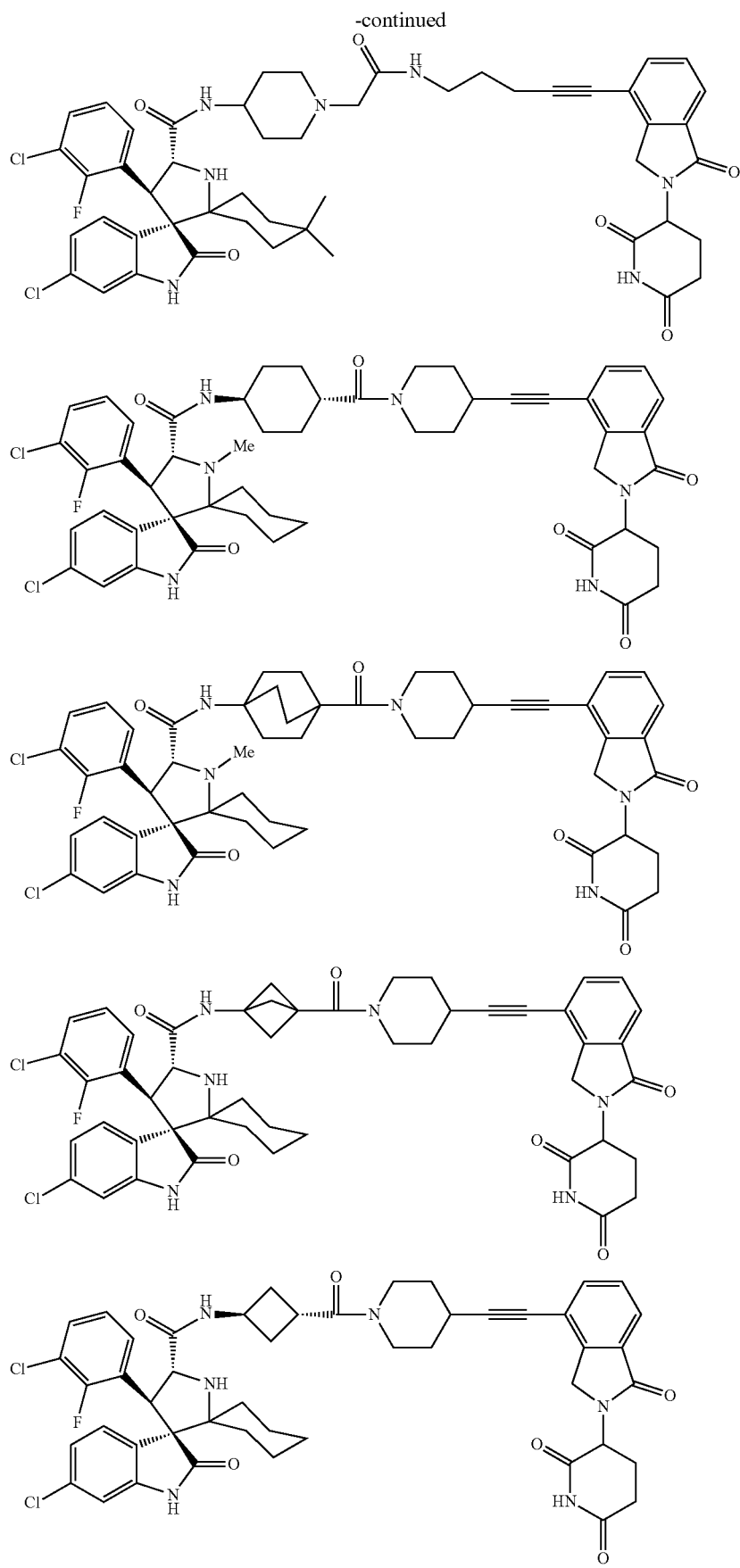

-continued
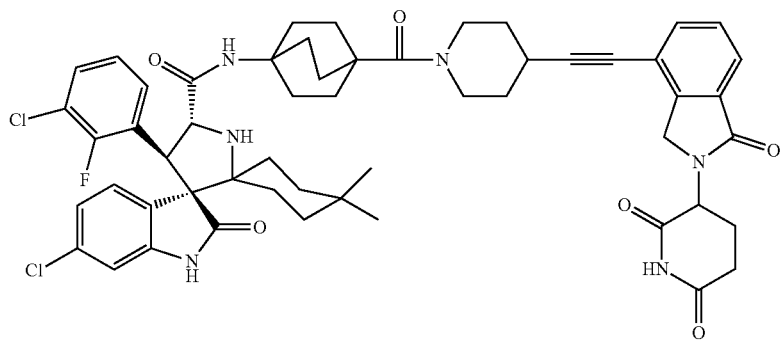
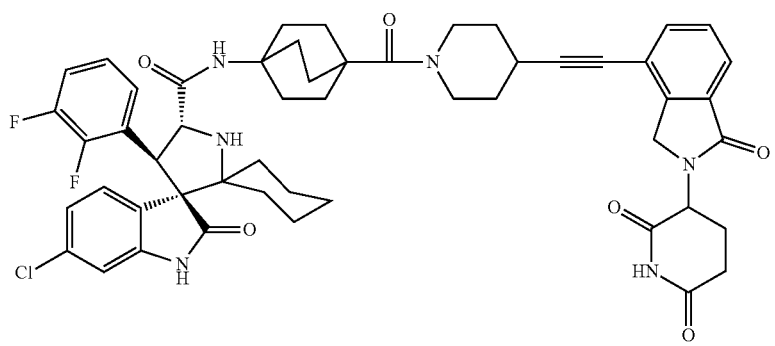
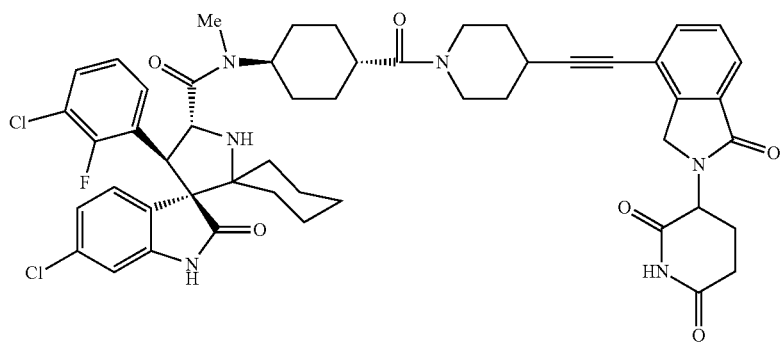
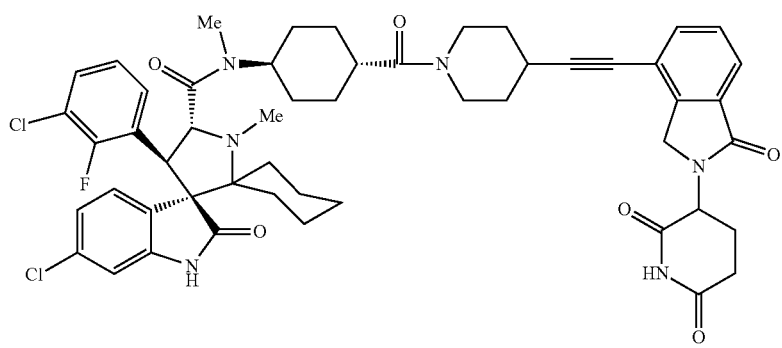
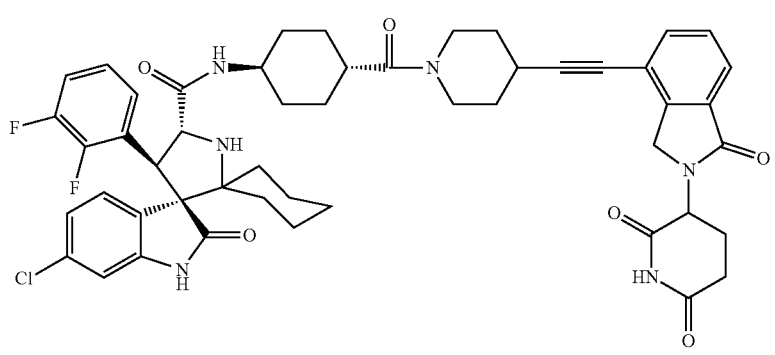

-continued
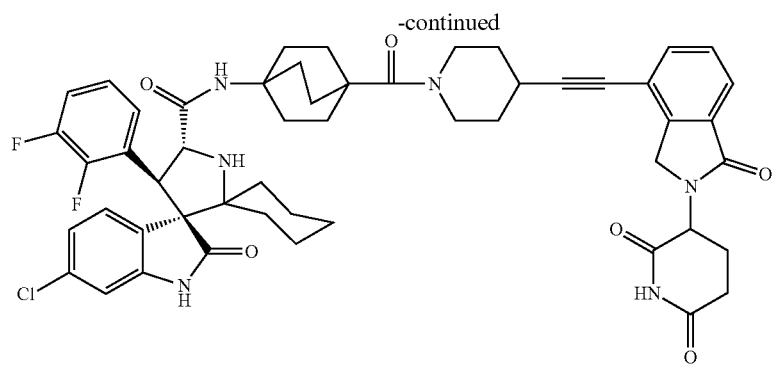
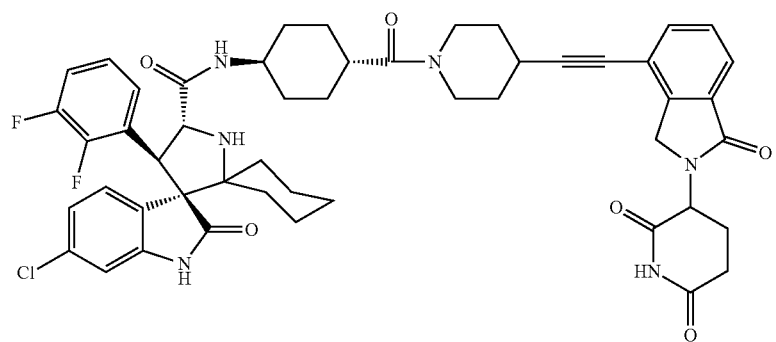
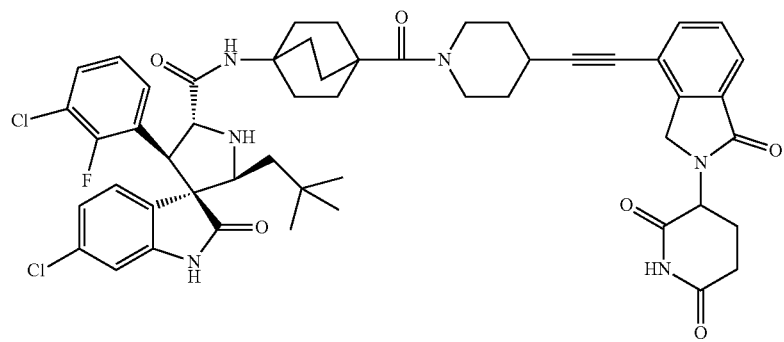
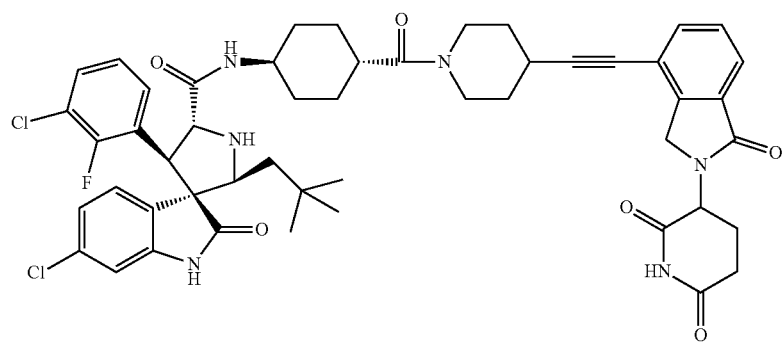

-continued
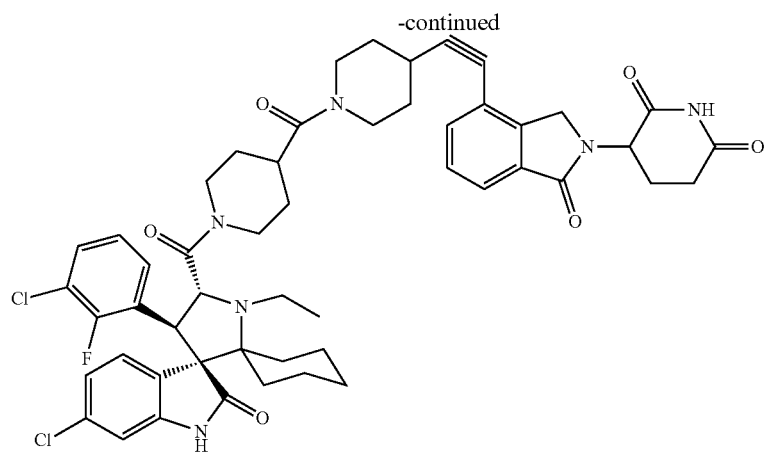
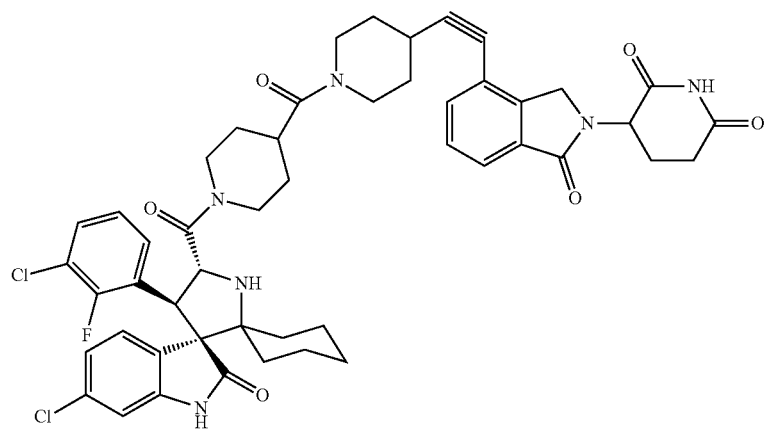
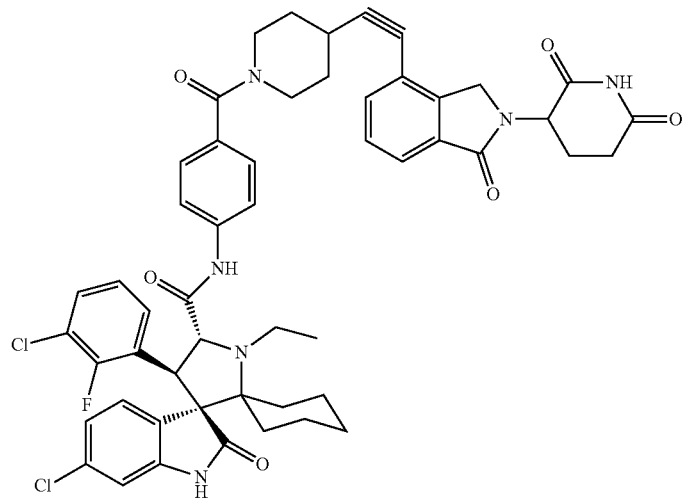

-continued
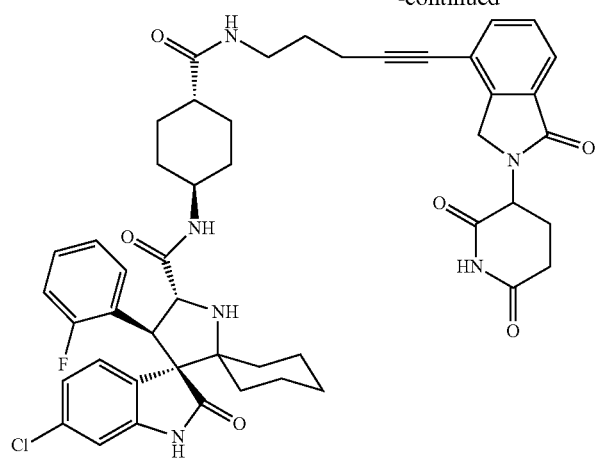
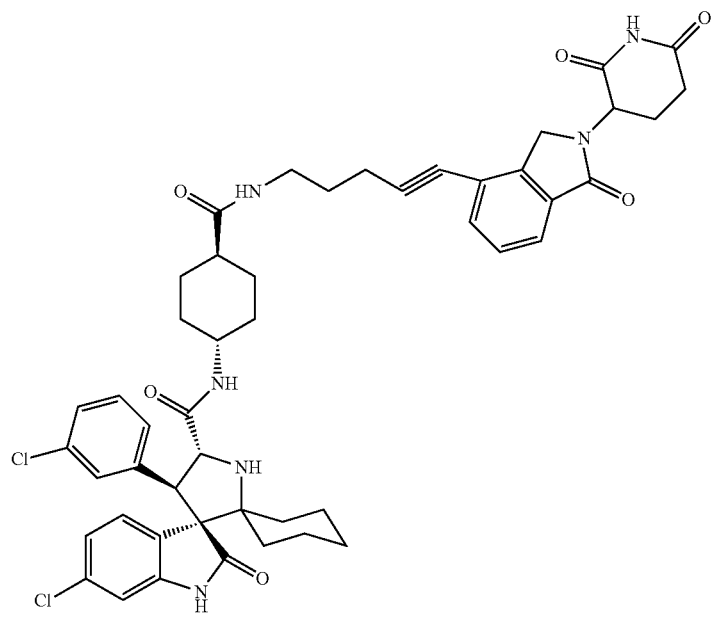
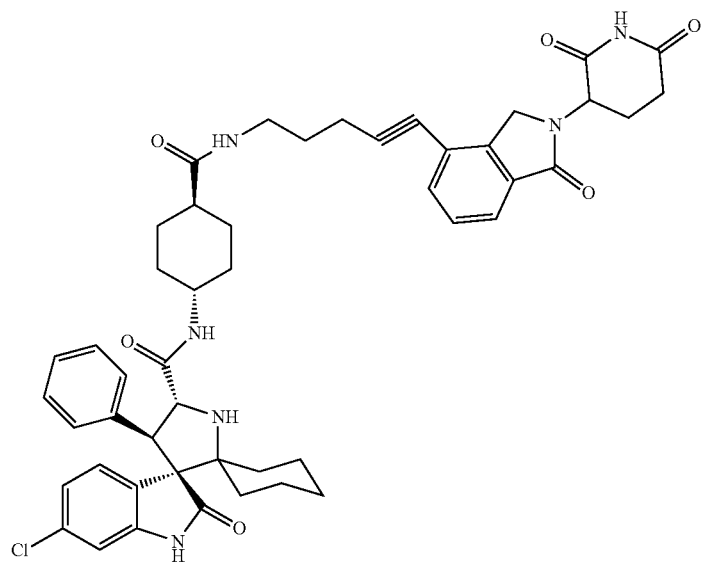

-continued
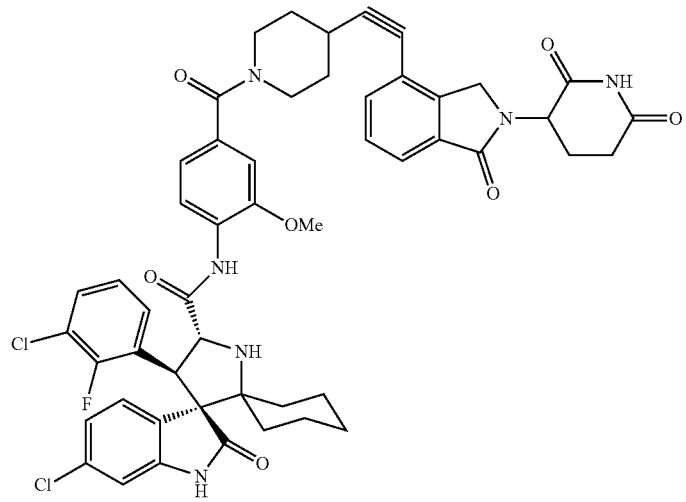
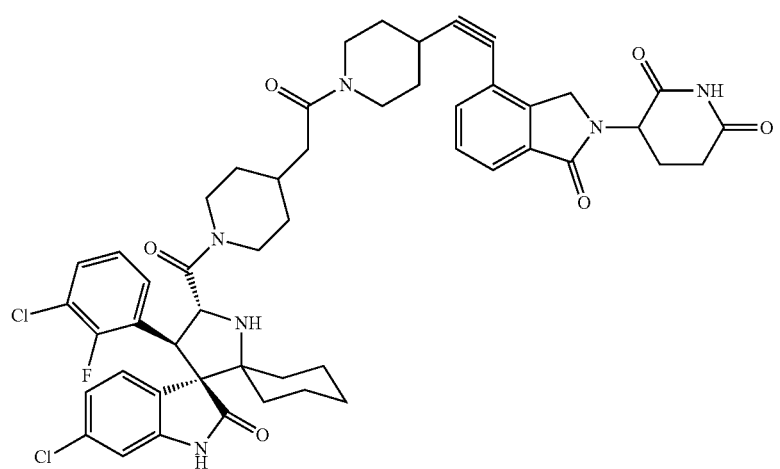
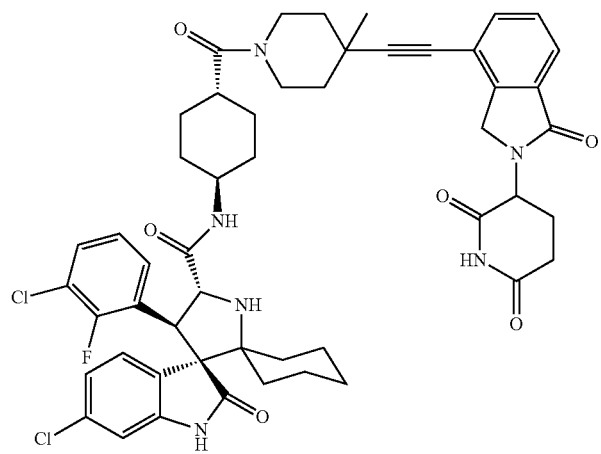

-continued
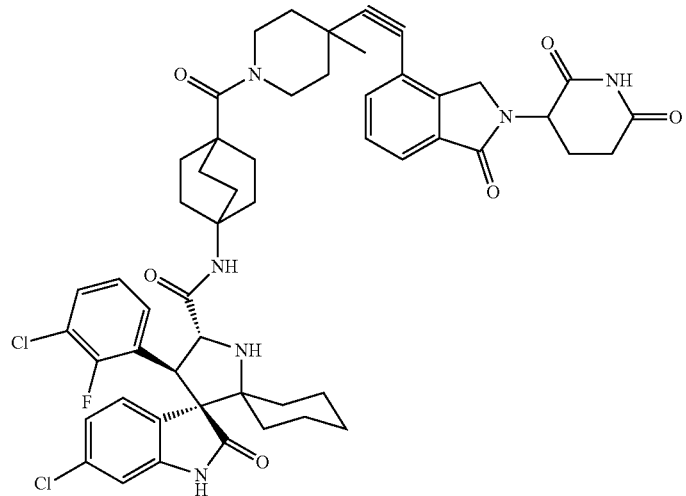
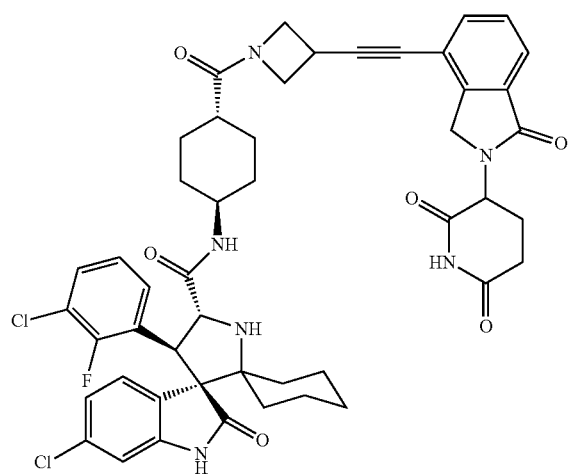
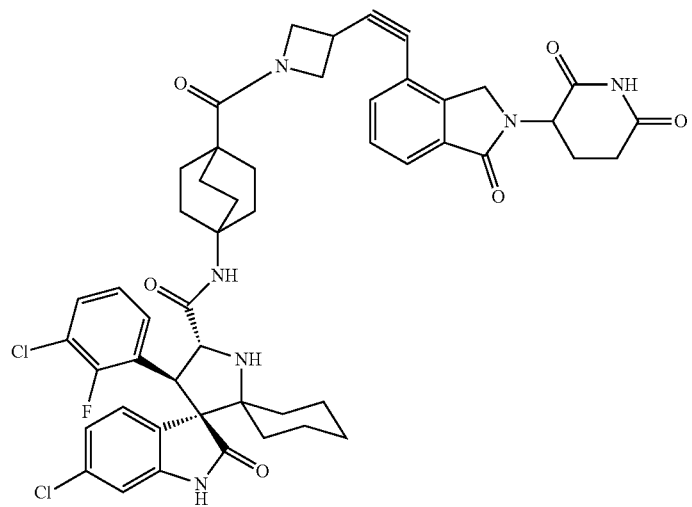

-continued

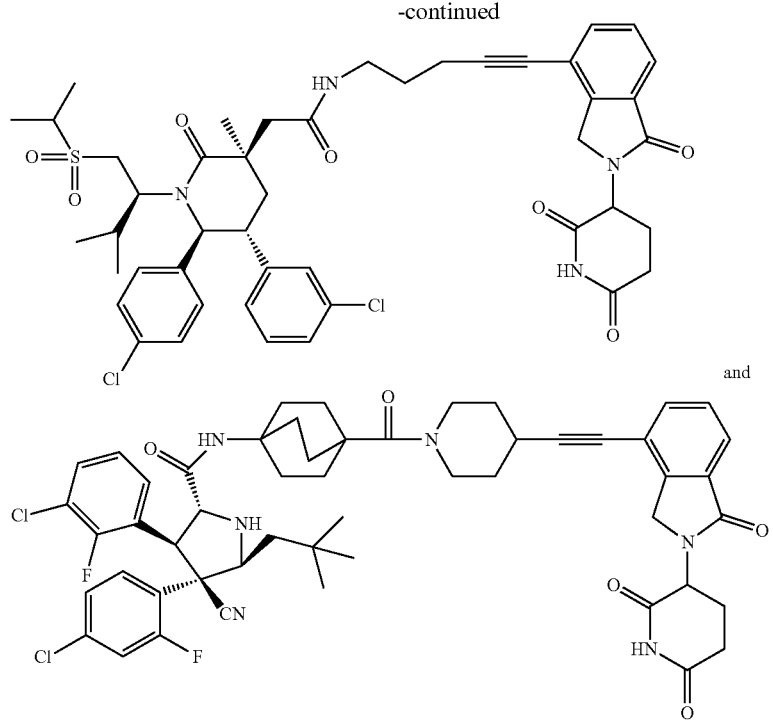

and or a pharmaceutically acceptable salt or solvate thereof.

4. The compound of claim 3 that is (3'R,4'S,5'R)-6"-chloro-4'-(3-chloro-2-fluorophenyl)-N-((1r,4R)-4-(4-((2-(2,6-dioxopiperidin-3-yl)-1-oxoisoindolin-4-yl)ethynyl)piperidine-1-carbonyl)cyclohexyl)-2"-oxodispiro[cyclohexane-1,2'-pyrrolidine-3',3"-indoline]-5'-carboxamide, or a pharmaceutically acceptable salt or solvate thereof.

5. The compound of claim 3 that is (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)bicyclo[2.2.2]octan-1-yl)-2"-oxodispiro[cyclohexane-1,2'-pyrrolidine-3',3"-indoline]-5'-carboxamide, or a pharmaceutically acceptable salt or solvate thereof.

6. A compound that is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(5-(2-(2,6-dioxopiperidin-3-yl)-1-oxoisoindolin-4-yl)pent-4-yn-1-yl)acetamide, or a pharmaceutically acceptable salt or solvate thereof.

7. A compound that is (2R,3S,4R,5S)-3-(3-chloro-2-fluorophenyl)-4-(4-chloro-2-fluorophenyl)-4-cyano-N-(4-(4-((2-(2,6-dioxopiperidin-3-yl)-1-oxoisoindolin-4-yl)ethynyl)piperidine-1-carbonyl)bicyclo[2.2.2]octan-1-yl)-5-neopentylpyrrolidine-2-carboxamide, or a pharmaceutically acceptable salt or solvate thereof.

8. The compound of claim 1, wherein the pharmaceutically acceptable salt is the ethane-1,2-disulfonic acid salt or the naphthalene-1,5-disulfonic acid salt.

9. A compound that is 3-(4-((1-((1r,4r)-4-aminocyclohexane-1-carbonyl)piperidin-4-yl)ethynyl)-1-oxoisoindolin-2-yl)piperidine-2,6-dione.

10. A pharmaceutical composition comprising the compound of claim 1, or a pharmaceutically acceptable salt or solvate thereof, and a pharmaceutically acceptable carrier.

11. A kit comprising the compound of claim 1, or a pharmaceutically acceptable salt or solvate thereof, and instructions for administering the compound, or a pharmaceutically acceptable salt or solvate thereof, to a subject having cancer.

12. A method of treating a subject in need thereof comprising administering to the subject a therapeutically effective amount of the compound of claim 1, or a pharmaceutically acceptable salt or solvate thereof, wherein the subject has a cancer.

13. The method of claim 12, wherein the cancer is any one or more cancer selected from the group consisting of adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological cancer, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

14. The method of claim 12, wherein the cancer is a hematological cancer.

15. The method of claim 14, wherein the hematological cancer is any one or more of the cancers of acute lymphocytic leukemia (ALL), acute eosinophilic leukemia, acute myeloid leukemia (AML), acute erythroid leukemia, chronic lymphocytic leukemia (CLL), acute lymphoblastic leukemia, small lymphocytic lymphoma (SLL), acute megakaryoblastic leukemia, multiple myeloma (MM), acute monocytic leukemia, Hodgkins lymphoma (HL), acute promyelocytic leukemia, non-Hodgkin's lymphoma (NHL), acute myelogeous leukemia, mantle cell lymphoma (MCL), B-cell prolymphocytic leukemia, marginal zone B-cell lymphoma, B-cell lymphoma, splenic marginal zone lymphoma, MALT lymphoma, follicular lymphoma (FL), precursor T-lymphoblastic lymphoma, Waldenstrom's macroglobulinemia (WM), T-cell lymphoma, diffuse large B-cell lymphoma (DLBCL), mast cell leukemia, marginal zone lymphoma (MZL), adult T cell leukemia/lymphoma, hairy cell leukemia (HCL), aggressive NK-cell leukemia, Burkitt's lymphoma (BL), angioimmunoblastic T-cell lymphoma, and Richter's transformation.

16. A method of treating a subject having cancer comprising:
    (a) determining whether an overexpression of MDM2 is present or absent in a biological sample taken from the subject; and
    (b) administering a therapeutically effective amount of a compound of claim 1, or a pharmaceutically acceptable salt thereof, to the subject if an overexpression of MDM2 is present in the biological sample.

17. A method, comprising administering a therapeutically effective amount of a compound of claim 1, or a pharmaceutically acceptable salt or solvate thereof, to a subject in need thereof, wherein:
    (a) the subject has cancer; and
    (b) the cancer is characterized as having an overexpression of MDM2.

18. The method of claim 14, wherein the hematological cancer is acute lymphocytic leukemia, chronic lymphocytic leukemia, or acute myeloid leukemia.

* * * * *